(12) United States Patent
Hendricksen et al.

(10) Patent No.: US 9,539,000 B2
(45) Date of Patent: Jan. 10, 2017

(54) KNOTLESS SUTURE ANCHOR AND METHODS OF USE

(71) Applicant: The Foundry, LLC, Menlo Park, CA (US)

(72) Inventors: Michael Hendricksen, Redwood City, CA (US); Mark Hirotsuka, San Jose, CA (US)

(73) Assignee: The Foundry, LLC, Menlo Park, CA (US)

( * ) Notice: Subject to any disclaimer, the term of this patent is extended or adjusted under 35 U.S.C. 154(b) by 570 days.

(21) Appl. No.: 13/855,445

(22) Filed: Apr. 2, 2013

(65) Prior Publication Data
US 2014/0142627 A1    May 22, 2014

Related U.S. Application Data

(63) Continuation of application No. 12/776,225, filed on May 7, 2010, now abandoned.
(Continued)

(51) Int. Cl.
*A61B 17/04* (2006.01)
*B29C 45/00* (2006.01)
*A61B 17/06* (2006.01)

(52) U.S. Cl.
CPC ..... *A61B 17/0401* (2013.01); *A61B 17/06166* (2013.01); *A61B 90/92* (2016.02); *B29C 45/00* (2013.01); *A61B 17/0482* (2013.01); *A61B 2017/044* (2013.01); *A61B 2017/045* (2013.01); *A61B 2017/0409* (2013.01); *A61B 2017/0412* (2013.01); *A61B 2017/0414* (2013.01); *A61B 2017/0416* (2013.01); *A61B 2017/0432* (2013.01); *A61B 2017/0433* (2013.01); *A61B 2017/0438* (2013.01);
(Continued)

(58) Field of Classification Search
CPC .................. A61B 17/0401; A61B 2017/0427; A61B 2017/0446–2017/0462; A61B 2017/0496
See application file for complete search history.

(56) References Cited

U.S. PATENT DOCUMENTS 3,939,969 A    2/1976   Miller et al.
3,981,307 A    9/1976   Borysko
(Continued)

FOREIGN PATENT DOCUMENTS

EP    1013229 A2    6/2000
EP    1588666 A2    10/2005
(Continued)

OTHER PUBLICATIONS

US 6,238,418, 05/2001, Schwartz et al. (withdrawn)
(Continued)

*Primary Examiner* — Julian W Woo
*Assistant Examiner* — Shaun L David
(74) *Attorney, Agent, or Firm* — Wilson Sonsini Goodrich & Rosati

(57) ABSTRACT

Various devices, systems and methods for knotless suturing of tissue are disclosed. These devices allow sutures to be anchored to bone, and more specifically provide a suture anchor which eliminates the need for knotting the suture. Thus, damaged tissue may be re-attached to a substrate tissue. The anchors have a minimum of moving parts may be suited to being a single molded polymer construction. The anchors will find particular utility in hip and shoulder arthroscopy, e.g. labral re-attachment and similar procedures.

47 Claims, 53 Drawing Sheets

Related U.S. Application Data

(60) Provisional application No. 61/177,602, filed on May 12, 2009, provisional application No. 61/219,290, filed on Jun. 22, 2009, provisional application No. 61/263,728, filed on Nov. 23, 2009, provisional application No. 61/263,751, filed on Nov. 23, 2009, provisional application No. 61/298,780, filed on Jan. 27, 2010, provisional application No. 61/304,352, filed on Feb. 12, 2010.

(52) U.S. Cl.
CPC ............... *A61B 2017/0441* (2013.01); *A61B 2017/0445* (2013.01); *A61B 2017/0448* (2013.01); *A61B 2017/0451* (2013.01); *A61B 2017/0453* (2013.01); *A61B 2017/0454* (2013.01); *A61B 2017/0461* (2013.01); *A61B 2017/0496* (2013.01); *A61B 2017/06142* (2013.01); *A61B 2090/0807* (2016.02)

(56) References Cited

U.S. PATENT DOCUMENTS

| | | |
|---|---|---|
| 4,249,656 A | 2/1981 | Cerwin et al. |
| 4,253,563 A | 3/1981 | Komarnycky |
| 4,406,363 A | 9/1983 | Aday |
| 4,412,614 A | 11/1983 | Ivanov |
| 4,413,727 A | 11/1983 | Cerwin et al. |
| 4,427,109 A | 1/1984 | Roshdy |
| 4,483,437 A | 11/1984 | Cerwin et al. |
| 4,491,218 A | 1/1985 | Aday |
| 4,533,041 A | 8/1985 | Aday et al. |
| 4,555,016 A | 11/1985 | Aday et al. |
| 4,572,363 A | 2/1986 | Alpern |
| 4,608,019 A | 8/1986 | Kumabe et al. |
| 4,615,435 A | 10/1986 | Alpern et al. |
| 4,750,492 A | 6/1988 | Jacobs |
| 4,884,681 A | 12/1989 | Roshdy et al. |
| 4,887,710 A | 12/1989 | Roshdy et al. |
| 4,898,156 A | 2/1990 | Gatturna et al. |
| 4,899,743 A | 2/1990 | Nicholson et al. |
| 4,904,272 A | 2/1990 | Middleton et al. |
| 4,946,043 A | 8/1990 | Roshdy et al. |
| 4,946,468 A | 8/1990 | Li |
| 4,968,315 A | 11/1990 | Gatturna |
| 4,969,892 A | 11/1990 | Burton et al. |
| 4,979,956 A | 12/1990 | Silvestrini |
| 5,002,550 A | 3/1991 | Li |
| 5,019,083 A | 5/1991 | Klapper et al. |
| 5,046,513 A | 9/1991 | Gatturna et al. |
| 5,057,112 A | 10/1991 | Sherman et al. |
| 5,061,283 A | 10/1991 | Silvestrini |
| 5,078,730 A | 1/1992 | Li et al. |
| 5,108,400 A | 4/1992 | Appel et al. |
| 5,152,790 A | 10/1992 | Rosenberg et al. |
| 5,171,251 A | 12/1992 | Bregen et al. |
| 5,174,087 A | 12/1992 | Bruno |
| 5,178,629 A | 1/1993 | Kammerer |
| 5,188,636 A | 2/1993 | Fedotov |
| 5,192,303 A | 3/1993 | Gatturna et al. |
| 5,201,656 A | 4/1993 | Sicurelli, Jr. |
| 5,207,679 A | 5/1993 | Li |
| 5,217,092 A | 6/1993 | Potter |
| 5,217,486 A | 6/1993 | Rice et al. |
| 5,242,457 A | 9/1993 | Akopov et al. |
| 5,258,016 A | 11/1993 | DiPoto et al. |
| 5,259,398 A | 11/1993 | Vrespa |
| 5,268,001 A | 12/1993 | Nicholson et al. |
| 5,282,809 A | 2/1994 | Kammerer et al. |
| 5,318,570 A | 6/1994 | Hood et al. |
| 5,336,240 A | 8/1994 | Metzler et al. |
| 5,352,230 A | 10/1994 | Hood |
| 5,358,511 A | 10/1994 | Gatturna et al. |
| 5,370,662 A | 12/1994 | Stone et al. |
| 5,380,334 A | 1/1995 | Torrie et al. |
| 5,383,905 A | 1/1995 | Golds et al. |
| 5,397,357 A | 3/1995 | Schmieding et al. |
| 5,407,420 A | 4/1995 | Bastyr et al. |
| 5,411,506 A | 5/1995 | Goble et al. |
| 5,411,523 A | 5/1995 | Goble |
| 5,415,651 A | 5/1995 | Schmieding |
| 5,417,691 A | 5/1995 | Hayhurst |
| 5,441,502 A | 8/1995 | Bartlett |
| 5,443,482 A | 8/1995 | Stone et al. |
| 5,454,815 A | 10/1995 | Geisser et al. |
| 5,464,425 A | 11/1995 | Skiba |
| 5,464,427 A | 11/1995 | Curtis et al. |
| 5,466,243 A | 11/1995 | Schmieding et al. |
| 5,480,403 A | 1/1996 | Lee et al. |
| 5,484,451 A | 1/1996 | Akopov et al. |
| 5,486,197 A | 1/1996 | Le et al. |
| 5,520,700 A | 5/1996 | Beyer et al. |
| 5,522,817 A | 6/1996 | Sander et al. |
| 5,522,843 A | 6/1996 | Zang |
| 5,522,844 A | 6/1996 | Johnson et al. |
| 5,527,342 A | 6/1996 | Pietrzak et al. |
| 5,540,718 A | 7/1996 | Bartlett |
| 5,545,180 A | 8/1996 | Le et al. |
| 5,554,171 A | 9/1996 | Gatturna et al. |
| 5,569,306 A | 10/1996 | Thal |
| 5,571,139 A | 11/1996 | Jenkins, Jr. |
| 5,573,543 A | 11/1996 | Akopov et al. |
| 5,573,548 A | 11/1996 | Nazre et al. |
| 5,575,801 A | 11/1996 | Habermeyer et al. |
| 5,578,057 A | 11/1996 | Wenstrom, Jr. |
| 5,584,835 A | 12/1996 | Greenfield |
| 5,584,836 A | 12/1996 | Ballintyn et al. |
| 5,584,860 A | 12/1996 | Goble et al. |
| 5,591,207 A | 1/1997 | Coleman |
| 5,601,557 A | 2/1997 | Hayhurst |
| 5,618,314 A | 4/1997 | Harwin et al. |
| 5,626,587 A | 5/1997 | Bishop et al. |
| 5,626,612 A | 5/1997 | Barlett |
| 5,626,613 A | 5/1997 | Schmieding |
| 5,630,824 A | 5/1997 | Hart |
| 5,643,320 A | 7/1997 | Lower et al. |
| 5,643,321 A | 7/1997 | McDevitt |
| 5,647,874 A | 7/1997 | Hayhurst |
| 5,649,963 A | 7/1997 | McDevitt |
| 5,658,313 A | 8/1997 | Thal |
| 5,662,662 A | 9/1997 | Bishop et al. |
| 5,681,333 A | 10/1997 | Burkhart et al. |
| 5,683,401 A | 11/1997 | Schmieding et al. |
| 5,683,418 A | 11/1997 | Luscombe et al. |
| 5,683,419 A | 11/1997 | Thal |
| 5,690,676 A | 11/1997 | DiPoto et al. |
| 5,690,677 A | 11/1997 | Schmieding et al. |
| 5,702,397 A | 12/1997 | Goble et al. |
| 5,713,903 A | 2/1998 | Sander et al. |
| 5,720,753 A | 2/1998 | Sander et al. |
| 5,720,766 A | 2/1998 | Zang et al. |
| 5,725,529 A | 3/1998 | Nicholson et al. |
| 5,725,557 A | 3/1998 | Gatturna et al. |
| 5,728,100 A | 3/1998 | Skiba |
| 5,728,135 A | 3/1998 | Bregen et al. |
| 5,728,136 A | 3/1998 | Thal |
| 5,733,307 A | 3/1998 | Dinsdale |
| 5,769,894 A | 6/1998 | Ferragamo |
| 5,782,863 A | 7/1998 | Bartlett |
| 5,782,864 A | 7/1998 | Lizardi |
| 5,782,865 A | 7/1998 | Grotz |
| 5,782,866 A | 7/1998 | Wenstrom, Jr. |
| 5,788,063 A | 8/1998 | Van Ness |
| 5,792,142 A | 8/1998 | Galitzer |
| 5,797,963 A | 8/1998 | McDevitt |
| 5,800,447 A | 9/1998 | Wenstrom, Jr. |
| 5,807,403 A | 9/1998 | Beyar et al. |
| 5,810,848 A | 9/1998 | Hayhurst |
| 5,814,051 A | 9/1998 | Wenstrom, Jr. |
| 5,814,070 A | 9/1998 | Borzone et al. |
| 5,814,071 A | 9/1998 | McDevitt et al. |
| 5,817,095 A | 10/1998 | Smith |
| 5,824,011 A | 10/1998 | Stone et al. |

(56) References Cited

U.S. PATENT DOCUMENTS

| | | |
|---|---|---|
| 5,842,478 A | 12/1998 | Benderev et al. |
| 5,843,087 A | 12/1998 | Jensen et al. |
| 5,851,219 A | 12/1998 | Goble et al. |
| 5,885,294 A | 3/1999 | Pedlick et al. |
| 5,894,921 A | 4/1999 | Le et al. |
| 5,899,920 A | 5/1999 | DeSatnick et al. |
| 5,904,704 A | 5/1999 | Goble et al. |
| 5,906,624 A | 5/1999 | Wenstrom, Jr. |
| RE36,289 E | 8/1999 | Le et al. |
| 5,935,129 A | 8/1999 | McDevitt et al. |
| 5,935,134 A | 8/1999 | Pedlick et al. |
| 5,938,686 A | 8/1999 | Benderev et al. |
| 5,941,882 A | 8/1999 | Jammet et al. |
| 5,944,724 A | 8/1999 | Lizardi |
| 5,944,739 A | 8/1999 | Zlock et al. |
| 5,948,000 A | 9/1999 | Larsen et al. |
| 5,948,001 A | 9/1999 | Larsen |
| 5,950,633 A | 9/1999 | Lynch et al. |
| 5,951,559 A | 9/1999 | Burkhart |
| 5,957,924 A | 9/1999 | Tormala et al. |
| 5,957,953 A | 9/1999 | DiPoto et al. |
| 5,961,538 A | 10/1999 | Pedlick et al. |
| 5,964,783 A | 10/1999 | Grafton et al. |
| 5,972,000 A | 10/1999 | Beyar et al. |
| 5,980,558 A | 11/1999 | Wiley |
| 5,993,451 A | 11/1999 | Burkhart |
| 5,993,458 A | 11/1999 | Vaitekunas et al. |
| 5,993,477 A | 11/1999 | Vaitekunas et al. |
| 6,007,566 A | 12/1999 | Wenstrom, Jr. |
| 6,019,768 A | 2/2000 | Wenstrom, Jr. et al. |
| 6,027,523 A | 2/2000 | Schmieding |
| 6,029,805 A | 2/2000 | Alpern et al. |
| 6,045,573 A | 4/2000 | Wenstrom, Jr. et al. |
| 6,045,574 A | 4/2000 | Thal |
| 6,066,160 A | 5/2000 | Colvin et al. |
| 6,080,154 A | 6/2000 | Reay-Young et al. |
| 6,086,608 A | 7/2000 | Ek et al. |
| 6,093,201 A | 7/2000 | Cooper et al. |
| 6,117,162 A | 9/2000 | Schmieding et al. |
| 6,146,406 A | 11/2000 | Shluzas et al. |
| 6,179,840 B1 | 1/2001 | Bowman |
| 6,183,479 B1 | 2/2001 | Tormala et al. |
| 6,190,401 B1 | 2/2001 | Green et al. |
| 6,214,031 B1 | 4/2001 | Schmieding et al. |
| 6,241,736 B1 | 6/2001 | Sater et al. |
| 6,264,676 B1 | 7/2001 | Gellman et al. |
| 6,267,718 B1 | 7/2001 | Vitali et al. |
| 6,270,518 B1 | 8/2001 | Pedlick et al. |
| 6,287,324 B1 | 9/2001 | Yarnitsky et al. |
| 6,293,961 B2 | 9/2001 | Schwartz et al. |
| 6,306,159 B1 | 10/2001 | Schwartz et al. |
| 6,319,252 B1 | 11/2001 | McDevitt et al. |
| 6,319,270 B1 | 11/2001 | Grafton et al. |
| 6,319,271 B1 | 11/2001 | Schwartz et al. |
| 6,319,272 B1 | 11/2001 | Brenneman et al. |
| 6,334,446 B1 | 1/2002 | Beyar |
| 6,338,765 B1 | 1/2002 | Statnikov |
| 6,368,350 B1 | 4/2002 | Erickson et al. |
| 6,387,113 B1 | 5/2002 | Hawkins et al. |
| 6,406,480 B1 | 6/2002 | Beyar et al. |
| 6,423,072 B1 | 7/2002 | Zappala |
| 6,461,373 B2 | 10/2002 | Wyman et al. |
| 6,500,169 B1 | 12/2002 | Deng |
| 6,511,499 B2 | 1/2003 | Schmieding et al. |
| 6,514,274 B1 | 2/2003 | Boucher et al. |
| 6,517,542 B1 | 2/2003 | Papay et al. |
| 6,520,980 B1 | 2/2003 | Foerster |
| 6,524,317 B1 | 2/2003 | Ritchart et al. |
| 6,527,794 B1 | 3/2003 | McDevitt et al. |
| 6,527,795 B1 | 3/2003 | Lizardi |
| 6,533,795 B1 | 3/2003 | Tran et al. |
| 6,544,281 B2 | 4/2003 | ElAttrache et al. |
| 6,551,330 B1 | 4/2003 | Bain et al. |
| 6,554,852 B1 | 4/2003 | Oberlander |
| 6,569,186 B1 | 5/2003 | Winters et al. |
| 6,569,188 B2 | 5/2003 | Grafton et al. |
| 6,575,984 B2 | 6/2003 | Beyar |
| 6,582,453 B1 | 6/2003 | Tran et al. |
| 6,585,730 B1 | 7/2003 | Foerster |
| 6,616,674 B2 | 9/2003 | Schmieding |
| 6,616,694 B1 | 9/2003 | Hart |
| 6,641,596 B1 | 11/2003 | Lizardi |
| 6,641,597 B2 | 11/2003 | Burkhart et al. |
| 6,645,227 B2 | 11/2003 | Fallin et al. |
| 6,652,561 B1 | 11/2003 | Tran |
| 6,652,562 B2 | 11/2003 | Collier et al. |
| 6,652,563 B2 | 11/2003 | Dreyfuss |
| 6,656,183 B2 | 12/2003 | Colleran et al. |
| 6,660,008 B1 | 12/2003 | Foerster et al. |
| 6,660,023 B2 | 12/2003 | McDevitt et al. |
| 6,673,094 B1 | 1/2004 | McDevitt et al. |
| 6,685,728 B2 | 2/2004 | Sinnott et al. |
| 6,689,153 B1 | 2/2004 | Skiba |
| 6,692,516 B2 | 2/2004 | West, Jr. et al. |
| 6,716,234 B2 | 4/2004 | Grafton et al. |
| 6,726,707 B2 | 4/2004 | Pedlick et al. |
| 6,743,233 B1 | 6/2004 | Baldwin et al. |
| 6,746,483 B1 | 6/2004 | Bojarski et al. |
| 6,767,037 B2 | 7/2004 | Wenstrom, Jr. |
| 6,770,073 B2 | 8/2004 | McDevitt et al. |
| 6,770,076 B2 | 8/2004 | Foerster |
| 6,773,436 B2 | 8/2004 | Donnelly et al. |
| 6,780,198 B1 | 8/2004 | Gregoire et al. |
| 6,830,572 B2 | 12/2004 | McDevitt et al. |
| 6,855,157 B2 | 2/2005 | Foerster et al. |
| 6,887,259 B2 | 5/2005 | Lizardi |
| 6,916,333 B2 | 7/2005 | Schmieding et al. |
| 6,932,834 B2 | 8/2005 | Lizardi et al. |
| 6,942,666 B2 | 9/2005 | Overaker et al. |
| 6,972,027 B2 | 12/2005 | Fallin et al. |
| 6,984,237 B2 | 1/2006 | Hatch et al. |
| 6,986,781 B2 | 1/2006 | Smith |
| 6,989,034 B2 | 1/2006 | Hamme et al. |
| 6,991,636 B2 | 1/2006 | Rose |
| 6,994,719 B2 | 2/2006 | Grafton |
| 7,022,129 B2 | 4/2006 | Overaker et al. |
| 7,029,490 B2 | 4/2006 | Grafton et al. |
| 7,033,380 B2 | 4/2006 | Schwartz et al. |
| 7,037,324 B2 | 5/2006 | Martinek |
| 7,052,499 B2 | 5/2006 | Steger et al. |
| 7,063,717 B2 | 6/2006 | St. Pierre et al. |
| 7,081,126 B2 | 7/2006 | McDevitt et al. |
| 7,083,638 B2 | 8/2006 | Foerster |
| 7,090,690 B2 | 8/2006 | Foerster et al. |
| 7,104,999 B2 | 9/2006 | Overaker |
| 7,131,973 B2 | 11/2006 | Hoffman |
| 7,144,414 B2 | 12/2006 | Harvie et al. |
| 7,144,415 B2 | 12/2006 | Del Rio et al. |
| 7,150,757 B2 | 12/2006 | Fallin et al. |
| 7,153,312 B1 | 12/2006 | Torrie et al. |
| 7,163,563 B2 | 1/2007 | Schwartz et al. |
| 7,195,634 B2 | 3/2007 | Schmieding et al. |
| 7,204,839 B2 | 4/2007 | Dreyfuss et al. |
| 7,217,279 B2 | 5/2007 | Reese |
| 7,226,469 B2 | 6/2007 | Benavitz et al. |
| 7,232,455 B2 | 6/2007 | Pedlick et al. |
| 7,235,100 B2 | 6/2007 | Martinek |
| 7,247,164 B1 | 7/2007 | Ritchart et al. |
| 7,250,057 B2 | 7/2007 | Forsberg et al. |
| 7,279,008 B2 | 10/2007 | Brown et al. |
| 7,300,451 B2 | 11/2007 | Crombie et al. |
| 7,309,337 B2 | 12/2007 | Colleran et al. |
| 7,309,346 B2 | 12/2007 | Martinek |
| 7,320,701 B2 | 1/2008 | Haut et al. |
| 7,329,272 B2 | 2/2008 | Burkhart et al. |
| 7,331,982 B1 | 2/2008 | Kaiser et al. |
| 7,335,221 B2 | 2/2008 | Collier et al. |
| RE40,237 E | 4/2008 | Bilotti et al. |
| 7,357,810 B2 | 4/2008 | Koyfman et al. |
| 7,361,195 B2 | 4/2008 | Schwartz et al. |
| 7,371,244 B2 | 5/2008 | Chatlynne et al. |
| 7,381,213 B2 | 6/2008 | Lizardi |
| 7,390,329 B2 | 6/2008 | Westra et al. |
| 7,390,332 B2 | 6/2008 | Selvitelli et al. |

(56) References Cited

U.S. PATENT DOCUMENTS

| | | |
|---|---|---|
| 7,407,512 B2 | 8/2008 | Bojarski et al. |
| 7,442,202 B2 | 10/2008 | Dreyfuss |
| 7,455,674 B2 | 11/2008 | Rose |
| 7,455,683 B2 | 11/2008 | Geissler et al. |
| 7,468,074 B2 | 12/2008 | Caborn et al. |
| 7,556,638 B2 | 7/2009 | Morgan et al. |
| 7,556,640 B2 | 7/2009 | Foerster |
| 7,566,339 B2 | 7/2009 | Fallin et al. |
| 7,572,275 B2 | 8/2009 | Fallin et al. |
| 7,572,283 B1 | 8/2009 | Meridew |
| 7,585,311 B2 | 9/2009 | Green et al. |
| 7,591,850 B2 | 9/2009 | Cavazzoni |
| 7,601,165 B2 | 10/2009 | Stone |
| 7,780,701 B1 | 8/2010 | Meridew et al. |
| 7,874,839 B2 | 1/2011 | Bouneff |
| 8,545,535 B2 | 10/2013 | Hirotsuka et al. |
| 2001/0027321 A1 | 10/2001 | Gellman et al. |
| 2002/0026187 A1 | 2/2002 | Swanson |
| 2002/0111653 A1 | 8/2002 | Foerster |
| 2002/0183762 A1 | 12/2002 | Anderson et al. |
| 2003/0060835 A1 | 3/2003 | Wenstrom, Jr. |
| 2003/0088272 A1 | 5/2003 | Smith |
| 2003/0105474 A1 | 6/2003 | Bonutti |
| 2003/0120309 A1 | 6/2003 | Colleran et al. |
| 2003/0130694 A1 | 7/2003 | Bojarski et al. |
| 2003/0135151 A1 | 7/2003 | Deng |
| 2003/0195563 A1 | 10/2003 | Foerster et al. |
| 2004/0002734 A1 | 1/2004 | Fallin et al. |
| 2004/0030341 A1 | 2/2004 | Aeschlimann et al. |
| 2004/0138706 A1 | 7/2004 | Abrams et al. |
| 2004/0236373 A1 | 11/2004 | Anspach, III et al. |
| 2005/0149122 A1 | 7/2005 | McDevitt et al. |
| 2005/0240199 A1 | 10/2005 | Martinek et al. |
| 2005/0245932 A1 | 11/2005 | Fanton et al. |
| 2005/0251208 A1 | 11/2005 | Elmer et al. |
| 2005/0283192 A1 | 12/2005 | Torrie et al. |
| 2006/0100630 A1 | 5/2006 | West, Jr. |
| 2006/0106422 A1 | 5/2006 | Del Rio et al. |
| 2006/0106423 A1 | 5/2006 | Weisel et al. |
| 2006/0149286 A1 | 7/2006 | Hoffman |
| 2006/0282083 A1 | 12/2006 | Fanton et al. |
| 2006/0293710 A1 | 12/2006 | Foerster et al. |
| 2007/0088391 A1 | 4/2007 | McAlexander et al. |
| 2007/0088412 A1 | 4/2007 | Ashman et al. |
| 2007/0162022 A1 | 7/2007 | Zhang et al. |
| 2007/0219557 A1 | 9/2007 | Bourque et al. |
| 2007/0225719 A1 | 9/2007 | Stone et al. |
| 2007/0255317 A1 | 11/2007 | Fanton et al. |
| 2007/0260259 A1 | 11/2007 | Fanton et al. |
| 2008/0009904 A1 | 1/2008 | Bourque et al. |
| 2008/0021474 A1 | 1/2008 | Bonutti et al. |
| 2008/0027444 A1 | 1/2008 | Malek |
| 2008/0054814 A1 | 3/2008 | Deppe et al. |
| 2008/0058816 A1 | 3/2008 | Philippon et al. |
| 2008/0086072 A1 | 4/2008 | Bonutti et al. |
| 2008/0103528 A1 | 5/2008 | Zirps et al. |
| 2008/0109080 A1 | 5/2008 | Aeschlimann et al. |
| 2008/0147119 A1 | 6/2008 | Cauldwell et al. |
| 2008/0188854 A1 | 8/2008 | Moser |
| 2008/0275469 A1 | 11/2008 | Fanton et al. |
| 2008/0306510 A1 | 12/2008 | Stchur |
| 2009/0012617 A1 | 1/2009 | White et al. |
| 2009/0069845 A1 | 3/2009 | Frushell et al. |
| 2009/0088798 A1 | 4/2009 | Snyder et al. |
| 2009/0099598 A1 | 4/2009 | McDevitt et al. |
| 2010/0016892 A1 | 1/2010 | Kaiser et al. |
| 2010/0121355 A1 | 5/2010 | Gittings et al. |
| 2010/0292731 A1 | 11/2010 | Gittings et al. |
| 2010/0292732 A1 | 11/2010 | Hirotsuka et al. |
| 2010/0292733 A1 | 11/2010 | Hendricksen et al. |
| 2013/0345746 A1 | 12/2013 | Gittings et al. |
| 2014/0005720 A1 | 1/2014 | Hirotsuka et al. |
| 2014/0031863 A1 | 1/2014 | Gittings et al. |
| 2015/0112384 A1 | 4/2015 | Hirotsuka et al. |
| 2015/0320413 A1 | 11/2015 | Gittings et al. |

FOREIGN PATENT DOCUMENTS

| | | |
|---|---|---|
| GB | 2084468 A | 4/1982 |
| WO | WO95/29637 A1 | 11/1995 |
| WO | WO97/30649 A1 | 8/1997 |
| WO | WO 03/096908 A2 | 11/2003 |
| WO | WO 03/096908 A3 | 4/2004 |
| WO | WO2006/037131 A2 | 4/2006 |
| WO | WO2006/039296 A2 | 4/2006 |
| WO | WO-2007078281 A2 | 7/2007 |
| WO | WO 2008/054814 A2 | 5/2008 |
| WO | WO 2008/054814 A3 | 6/2008 |
| WO | WO2008/109087 A1 | 9/2008 |
| WO | WO 2008/124206 A2 | 10/2008 |
| WO | WO 2008/124463 A2 | 10/2008 |
| WO | WO 2008/124206 A3 | 12/2008 |
| WO | WO 2009/023034 A1 | 2/2009 |
| WO | WO 2009/039513 A1 | 3/2009 |

OTHER PUBLICATIONS

U.S. Appl. No. 14/015,934, filed Aug. 30, 2013, Hirotsuka et al.
Notice of allowance dated Aug. 2, 2013 for U.S. Appl. No. 12/776,208.
Office action dated Jun. 5, 2012 for U.S. Appl. No. 12/605,065.
Office action dated Jun. 18, 2013 for U.S. Appl. No. 12/776,208.
Office action dated Oct. 23, 2014 for U.S. Appl. No. 14/015,934.
European search report and search opinion dated Apr. 2, 2015 for EP Application No. 10775303.0.
European search report and search opinion dated Apr. 20, 2015 for EP Application No. 10775304.8.
Office action dated Apr. 20, 2015 for U.S. Appl. No. 13/692,596.
Co-pending U.S. Appl. No. 14/804,178, filed Jul. 20, 2015.
Office action dated Sep. 11, 2015 for U.S. Appl. No. 13/749,038.
U.S. Appl. No. 13/692,596, filed Dec. 3, 2012, Gittings et al.
U.S. Appl. No. 13/749,038, filed Jan. 24, 2013, Gittings et al.
Ambrose et al., "Bioabsorbable Implants: Review of Clinical Experience in Orthopedic Surgery," Annals of Biomedical Engineering, Jan. 2004; 32(1):171-177.
Arthrex, Inc., 2.5 mm PushLock® Knotless Suture Anchor [brochure], 2007, 2 pages total.
Arthrex, Inc., "4.5 mm/6.7 mm Low Profile Screw System Surgical Technique" [brochure], 2009, 6 pages total.
Arthrex, Inc., "Acetabular Labral Repair Using the Bio-SutureTak® Suture Anchor System Surgical Technique" [brochure], 2007, 6 pages total.
Arthrex, Inc., "Achilles SutureBridgeTM Surgical Technique" [brochure], 2009, 6 pages total.
Arthrex, Inc., "ACL Graft Tensioning using the Suture Tensioner with Tensionmeter Surgical Technique" [brochure], 2009, 6 pages total.
Arthrex, Inc., "AdapteurTM Power System II" [brochure], 2008, 12 pages total.
Arthrex, Inc., "Advanced Technology" [brochure], 2008, 15 pages total.
Arthrex, Inc., "All-Inside BTB ACL RetroConstructionTM with Bone-Tendon-Bone Grafts Surgical Technique" [brochure], 2007, 8 pages total.
Arthrex, Inc., "Arthrex 300 Power System—Small Bone" [brochure], undated, 2 pages total.
Arthrex, Inc., "Arthrex 600 Power System—Small Bone" [brochure], undated, 2 pages total.
Arthrex, Inc., "Arthrex ACPTM Double Syringe System" [brochure], 2009, 6 pages total.
Arthrex, Inc., "Arthrex Bio-Composite Suture Anchors", p. 9 of 510(k) Summary, FDA Approval Letter and Indications of Use for 510(k) No. K082810, Jan. 2009, 6 pages total.
Arthrex, Inc., "Arthrex Flatfoot Solutions"[brochure], 2008, 2 pages total.
Arthrex, Inc., "Arthrex Hallux Valgus Solutions"[brochure], 2008, 2 pages total.
Arthrex, Inc., "Arthrex PushLock, Tak, and Corkscrew Products", p. 12 of 510(k) Summary, FDA Approval Letter and Indications of Use for 510(k) No. K061863, Oct. 2006, 6 pages total.

(56) References Cited

OTHER PUBLICATIONS

Arthrex, Inc., "Arthroscopic Meniscal Repair: Arthroscopic All-Inside Meniscal Repair with the Meniscal ViperTM and DarkstickTM Surgical Technique" [brochure], 2006, 6 pages total.
Arthrex, Inc., "Arthroscopic Rotator Cuff Repair: Bio-Corkscrew® Suture Anchor Rotator Cuff Repair Surgical Technique" [brochure], 2007, 6 pages total.
Arthrex, Inc., "Arthroscopy Instruments" [brochure], 2008, 12 pages total.
Arthrex, Inc., "Beach Chair Lateral Traction Device Assembly Instructions" [instructions for use], 2006, 2 pages total.
Arthrex, Inc., "BioComposite SutureTak, BioComposite Corkscrew FT and BioComposite PushLock: An In Vitro Degradation Study" [white paper], Arthrex Research and Development, 2009, 1 page.
Arthrex, Inc., "BioCompositeTM Interference Screws for ACL and PCL Reconstruction," Arthrex Research and Development, 2008, 5 pages total.
Arthrex, Inc., "BioCompositeTM Interference Screws: A Stronger Turn in ACL/PCL Reconstruction," 2008, 56 pages total.
Arthrex, Inc., "Bio-Compression Screw System" [brochure], 2008, 6 pages total.
Arthrex, Inc., "Bio-FASTak® Bankart Repair Surgical Technique" [brochure], 2007, 6 pages total.
Arthrex, Inc., "Biomechanical Testing Comparison of Cayenne Medical and Arthrex, Inc. Repair Products" [white paper], Arthrex Research and Development, 2009, 1 page total.
Arthrex, Inc., "Bio-PostTM and Washer System" [brochure], 2001, 2 pages total.
Arthrex, Inc., "Bio-SutureTak Suture Anchor" [brochure], 2006, 2 pages total.
Arthrex, Inc., "Bio-TenodesisTM Screw System" [brochure], 2008, 6 pages total.
Arthrex, Inc., "Bone, Tendon or Ligament Repair?" [brochure], 2004, 1 page total.
Arthrex, Inc., "ClearCut Burrs" [brochure], 2006, 2 pages total.
Arthrex, Inc., "Comprehensive Solutions for Forefoot and Midfoot Surgery using the Mini TightRope® System—Five Surgical Techniques" [brochure], 2008, 13 pages total.
Arthrex, Inc., "CoolCut Series: Shaver Blades and Burrs" [brochure], 2009, 4 pages total.
Arthrex, Inc., "Double Row Rotator Cuff Repair using the Bio-Corkscrew® FT Surgical Technique" [brochure], 2007, 6 pages total.
Arthrex, Inc., "Elbow/Ankle Arthroscopy Instrument Set" [brochure], 2007, 8 pages total.
Arthrex, Inc., "Endoscopic Carpal Tunnel Release System" [brochure], 2000 ,2 pages total.
Arthrex, Inc., "FiberWire® Braided Composite Suture" [brochure], 2008, 8 pages total.
Arthrex, Inc., "FiberWire® Collective Summary of Strength and Biocompatibility Testing Data Comparisons of Polyester and Polyblend Sutures" [white paper], 2006, 4 pages total.
Arthrex, Inc., "FiberWire® Confidence After Closure" [brochure], 2008, 6 pages total.
Arthrex, Inc., "FiberWire® Orthopaedic Composite Suture" [sell sheet], 2007, 2 pages total.
Arthrex, Inc., "FlipCutter ACL Reconstruction™: ACL Reconstruction using the FlipCutterTM and the Constant Femoral Guide Surgical Technique" [brochure], 2008, 6 pages total.
Arthrex, Inc., "FlipCutterTM" [brochure], 2009, 2 pages total.
Arthrex, Inc., "Freedom in Anatomic Femoral Socket Placement" [brochure], 2009, 2 pages total.
Arthrex, Inc., "Fulfilling the Need for Precision and Speed Rotator Cuff Repair" [brochure], 2009, 12 pages total.
Arthrex, Inc., "Innovative Solutions for Hip Arthroscopy" [brochure], 2008, 16 pages total.
Arthrex, Inc., "Knotless Rotator Cuff Repair: SpeedBridgeTM and SpeedFixTM Knotless Rotator Cuff Repair using the SwiveLockTM C and FiberTape® Surgical Technique" [brochure], 2008, 8 pages total.
Arthrex, Inc., "Knotless SingleRow Rotator Cuff Repair using the PushLockTM and FiberTape® Surgical Technique" [brochure], 2007, 4 pages total.
Arthrex, Inc., "MultiFire Scorpion™ Independently Pass Two FiberWire® Suture Tails Through Tissue Without Scorpion Removal" [brochure], 2009, 4 pages total.
Arthrex, Inc., "Next Generation in Knee Ligament Reconstruction & Repair Technology" [brochure], 2009, 42 pages total.
Arthrex, Inc., "Orthopaedic Procedure Electrosurgical System (ORES®)" [brochure], 2008, 11 pages total.
Arthrex, Inc., "OSferion: Porous Trapezoid 6-TCP Synthetic Grafting of BTB Autograft Harvest Sites" [brochure], 2008, 18 pages total.
Arthrex, Inc., "OSferion: Porous Trapezoid 6-TCP Synthetic Wedge Grafting of Tibial and Femoral Opening Wedge Osteotomy Sites" [brochure], 2009, 6 pages total.
Arthrex, Inc., "Percutaneous Glenohumeral Repair with SutureTak® Implants" [brochure], 2009, 2 pages total.
Arthrex, Inc., "ProStop® and ProStop® Plus for Correction of Posterior Tibial Tendon Dysfunction," [brochure], 2009, 6 pages total.
Arthrex, Inc., "ProWickTM Knee Postoperative and Cold Therapy Dressing System" [brochure], 2009, 4 pages total.
Arthrex, Inc., "ProWickTM Shoulder Postoperative and Cold Therapy Dressing System" [brochure], 2009, 4 pages total.
Arthrex, Inc., "Pull Out Strength of a 3.5 mm Bio-PushLock (AR-1926B)" [white paper], Arthrex Research and Development Nov. 10, 2005, 1 page total.
Arthrex, Inc., "PushLock® Bankart & SLAP Repair: PushLock® Knotless Anchor for Bankart & SLAP Repair Surgical Technique" [brochure], 2009, 8 pages total.
Arthrex, Inc., "PushLock® Knotless Instability Repair" [brochure], 2009, 12 pages total.
Arthrex, Inc., "PushLock®" [advertisement], 2008, 1 page total.
Arthrex, Inc., PushLockTM [directions for use], DFU-0099, Revision 8, 2 page total.
Arthrex, Inc., "Raising the Bar in Arthroscopic Imaging and Resection Technology" [brochure], 2009, 8 pages total.
Arthrex, Inc., "RetroConstruction™ Minimally Invasive Options for Anatomic ACL/PCL Reconstruction" [brochure], 2009, 11 pages total.
Arthrex, Inc., "Scorpion—Fulfilling the Need for Precision and Speed in Arthroscopic Rotator Cuff Repair" [brochure], 2008, 6 pages total.
Arthrex, Inc., "Shaver Blades and Burrs" [brochure], 2005, 1 page total.
Arthrex, Inc., "Single Use Disposable Shaver Blades and Burrs" [brochure], 2008, 2 pages total.
Arthrex, Inc., "Small Joint: Fracture—Fusion—Osteotomy Fixation Options" [brochure], 2007, 2 pages total.
Arthrex, Inc., "SutureLass™ SD Products Reference Guide" [brochure], 2007, 1 page total.
Arthrex, Inc., "SutureTakTm Suture Anchors" [directions for use], DFU-0069, Revision 10, 2 pages total.
Arthrex, Inc., "SwiveLockTM & FiberChain™ Knotless Rotator Cuff Repair Surgical Technique" [brochure], 2007, 8 pages total.
Arthrex, Inc., "Thumb UCL Repair/Reconstruction: 2.5 mm PushLock®/3 mm × 8 mm BioTenodesisTM Thumb Collateral Ligament Repair/Reconstruction" [brochure], 2008, 8 pagest total.
Arthrex, Inc., "Transtibial ACL Reconstruction with Soft Tissue Grafts Surgical Technique" [brochure], 2007, 5 pages total.
Arthrex, Inc., "Trim-It Drill Pin™ The Need to Remove Hardware is Disappearing" [brochure], 2009, 2 pages total.
Arthrex, Inc., "Trim-It Drill Ping Osteotomy Fixation Kit" [brochure], 2009, 6 pages total.
Arthrex, Inc., "Trim-ItTm Screw System" [brochure], 2006, 6 pages total.
Arthrex, Inc., "V-TakTm Soft Tissue Anchor" [brochure], 2006, 6 pages total.
Arthrex, Inc., "Wishbone™ Series Arthroscopy Instruments" [brochure], 2008, 8 pages total.
Arthrex, Inc., In Arthroscopic Surgery, You Can't Treat it If You Can't Reach It[brochure], 2007, 12 pages total.

(56) References Cited

OTHER PUBLICATIONS

Arthrex, Inc., New Materials in Sports Medicine [white paper], 2006, 7 pages total.
Arthrex, Inc., The Arthrex Chondral DartTM [brochure], 2006, 4 pages total.
Arthrex, Inc., The Continuous Wave III Arthroscopy Pump: Clear Vision in Arthroscopic Fluid Management [brochure], 2006, 12 pages total.
Arthrex, Inc., The Fully Threaded Family of Soft Tissue Repair Anchors: Cortical Cancellous Fixation with Fiberwire® Composite Suture for Superior Repair Strength [brochure], 2008, 6 pages total.
Arthrex, Inc., The Next Generation in Foot and Ankle Repair Technology [brochure], 2009, 44 pages total.
Arthrex, Inc., The Next Generation in Hand, Wrist and Elbow Repair Technology [brochure], 2009, 28 pages total.
Arthrex, Inc., The Next Generation in Shoulder Repair Technology [brochure], 2008, 24 pages total.
Arthrex, Inc., The Next Generation in Shoulder Repair Technology [brochure], 2009, 26 pages total.
Arthrex, Inc., The OATS® Sterile, Single Use Kit [brochure], 2007, 2 pages total.
Arthrex. Acetabular Labral Repair [brochure], Arthrex, Inc., 2007, 6 pages total; retrieved from the Internet: <http://arthromed.org/pdf/hip/Surgical%20Techniques/Acetabular%20Labral%20Repair%2Ou sing%20the%20PushLock%20Knotless%20Anchor%20System.pdf>.
Arthrex. Bio-Corkscrew Anchor FT and Corkscrew FT II Suture Anchors [brochure], Arthrex, Inc., 2005, 6 pages total; retrieved from the Internet: <http://www.resed.ac.uk/fellows/Ivanrensburg/classification/surgtech/arthrex/arthrex% 20man uals/biocorkscrew.pdf>.
Arthrex. Bio-SutureTak Bankart & SLAP Repair [brochure], Arthrex, Inc., 2007, 6 pages total; retrieved from the Internet: <http://depts.washington.edu/shoulder/Surgery/ArthroseopicTechniques/Arthrex/Bio-SutureTak-SLAP-Bankart-Repair.pdf>.
ArthroCare Corporation, "LabraLock P Knotless Implant w/Inserter Handle" [website], 1 page; retrieved: <http://www.arthrocaresportsmedicine.com/products/view/430>.
ArthroCare Corporation, "Magnum® MP Suture Implant" [brochure], 2009, 2 pages total.
ArthroCare Corporation, "Mini Magnum Knotless Implant w/Inserter Handle" [website], 1 page; retrieved: <http://www.arthrocaresportsmedicine.com/products/view/429>.
ArthroCare Corporation, "Mini Magnum® Knotless Fixation Implant" [brochure], 2009, 2 pages total.
ArthroCare Corporation, "SpeedScrewTM Fully Threaded OPUS® Knotless Fixation Implant" [brochure], 2009, 2 pages total.
ArthroCare Corporation, The OPUS® AutoCuff System Featuring SpeedScrew for Rotator Cuff Repair Technical Guide [brochure], 2009, 8 pages total.
ArthroCare Corporation, The OPUS® AutoCuff System for Rotator Cuff Repair Technical Guide [brochure], 2008, 8 pages total.
ArthroCare. Opus LabraFix Knotless System [brochure], ArthroCare Corporation, 2008, A1027 Rev D, 6 pages total; retrieved: <http://www.arthrocaresportsmedicine.com/files/datasheets/A1027D.pdf>.
Arthrotek®. Charlotte™ Shoulder System: Arthroscopic Bankart Lesion Repair Using the 3.5 mm LactoScrew Suture Anchor [brochure], a Biomet Company. 2006, 4 pages total.
Arthrotek® MicroMax™fly Resorbable Suture Anchor [brochure], a Biomet Company. 2006, 8 pages total.
Arthrotek®. Charlotte™ Shoulder System [brochure], a Biomet Company. 2006, 16 pages total.
Arthrotek®. CharlotteTM Shoulder System: SLAP Lesion Repair Using the 3.5 mm LactoScrew Suture Anchor [brochure], a Biomet Company. 2002, 4 pages total.
Arthrotek®. MaxBraidTM PE Suture [brochure], a Biomet Company. 2004, 2 pages total.

Barber et al., "Suture Anchor—Update 1999," Arthroscopy, Oct. 1999; 15(7):719-725.
Bardana et al, The Effect of Suture Anchor Design and Orientation on Suture Abrasion: An In Vitro Study, Arthroscopy, Mar. 2003; 19(3,):274-281.
Benthien et al., "Cyclic Loading Achilles Tendon Repairs: A Comparison of Polyester and Polyblend Suture," Foot Ankle Int. Jul. 2006;27(7):512-518.
Biomet Sports Medicine, Hitch Suture Anchor [brochure], 2008, 2 pages total.
Biomet Sports Medicine, MicroMax™ Flex Suture Anchor MicroMaxTM Resorbable Suture Anchor [brochure], 2009, 20 pages total.
Biomet Sports Medicine, MicroMaxTm Flex Suture Anchor [advertisement], 2009, 2 pages total.
Biomet Sports Medicine, The Material Difference: Options for Rotator Cuff Repair, Labral Repair and Suture Management [brochure], 2008, 12 pages total.
Biomet, Inc., MicroMax-rm Resorbable Suture Anchor [website], 1 page; retrieved from the Internet: <http://www.biomet.com/sportsMedicine/productDetail.cfm?category=23& subCategory=33& product=108.
Blokhuis et al., "Properties of Calcium Phosphate Ceramics in Relation to Their In Vivo Behavior," J Trauma. Jan. 2000;48(1):179-86.
Brady et al., "Arthroscopic Rotator Cuff Repair: Establishing the Footprint," Techniques in Shoulder & Elbow Surgery, Dec. 2005; 6(4):242-251.
Burkhart et al., "Loop Security as a Determinant of Tissue Fixation Security," Arthroscopy, Oct. 1998;14(7):773-776.
Burkhart et al., "SLAP Lesions in the Overhead Athlete," Operative Techniques in Sports Medicine, Jul. 2000; 8(3):213-220.
Burkhart, "Arthroscopic Repair of Retracted Adhesed Rotator Cuff Tears and Subscapularis Tears: The Effective Use of Interval Slide Releases," Int J Shoulder Surg 2007; 1(1):39-44; retrieved from the internet: <http://www.internationalshoulderjournal.org/text.asp?2007/1/1/39/30677>.
Burkhart, "Arthroscopic Rotator Cuff Repair: Indications and Technique," Operative Techniques in Sports Medicine, Oct. 1997; 5(4):204-214.
Burkhart, "Knotless Self-Reinforcing Rotator Coff Repair with FiberChain-SwiveLock System" [video recording], ArthroCologne, 2nd International Symposium on Operative and Biologic Treatments in Sports Medicine, Cologne, Germany, Jun. 15-16, 2007; retrieved from thet Internet: <http://www.arthrocologne.com/SwiveLock-Rotator-Cuff-Repair.16361.html.
Burkhart, New Thoughts on SLAP Lesions, Arthroscopy and Arthroplasty of the Shoulder 15th Annual San Diego, 1998; pp. 351-355.
Bynum et al., "Failure Mode of Suture Anchors as a Function of Insertion Depth," Am J Sports Med Jul. 2005; 33(7):1030-1034.
C2M Medical, Inc., "CinchTM Knotless Fixation Implant System", pp. 63-65 of 510(k) Summary, FDA Approval Letter and Indications of Use for 510(k) No. K073226, Dec. 2007, 5 pages total.
Caborn et al., "A Biomechanical Comparison of Initial Soft Tissue Tibial Fixation Devices: The Intrafix Versus a Tapered 35-mm Bioabsorbable Interference Screw," Am J Sports Med, Jun. 2004; 32(4):956-961.
Chang et al., "Biomechanical Evaluation of Meniscal Repair Systems: A Comparison of the Meniscal Viper Repair System, the Vertical Mattress FasT-Fix Device, and Vertical Mattress Ethibond Sutures," Am J Sports Med, Dec. 2005; 33(12):1846-1852.
Chokshi et al., The effect of arthroscopic suture passing instruments on rotator cuff damage and repair strength, Bulletin of the NYU Hospital for Joint Diseases, Winter-Spring, 2006; 63(3/4):123-125; retrieved from the Internet: <http://www.nyuhjdbulletin.org/Mod/BulletinA/63N3-4/DocsA/63N3-4_11.pdf>.
Conmed Corporation, "Bio Mini-Revo® Anchor" [website], 1 page; retrieved from the Internet: <http://www.conmed.com/products_shoulder_biominirevo.php>.
Conmed Corporation,, "Bio Mini-Revo Suture Anchor", 510(k) Summary, FDA Approval Letter, FDA Approval Letter, and Indications of Use for 510(k) No. K073226, Jul. 2008, 5 pages total.

(56) References Cited

OTHER PUBLICATIONS

Conmed Linvatec, "Arthroscopy Product Catalog" [catalog], 2009, 194 pages total.
Conmed Linvatec, "Bio Mini-Rev™ Surgical Technique" [brochure] 2006, 12 pages total.
Conmed Linvatec, "Bio-Anchor® Shoulder Instability Repair System" [website], 2006, 1 page; retrieved from the Internet: <http://www.conmed.com/products_shoulder_bioanch.php>.
Conmed Linvatec, "Course: Bio Mini-Revo TM Surgical Technique—Designed in conjunction with Stephen J. Snyder, MD" [Slideshow] 2006, 26 pages; retrieved from the Internet: <http://www.conmed.com/SurgicalTechniques/BioMiniRevo.swf>.
Conmed Linvatec, "DuetTM Suture Anchor" [brochure], 2008, 4 pages total.
Conmed Linvatec, "Linvatec SRS Shoulder Restoration System: Simple Solutions for Complex Procedures" [website], 2009, 2 pages; retrieved from the Internet: <http://www.conmed.com/products_shoulder_srs_system.php?SelectCountry=0THER+COUNTRY.>.
Conmed Linvatec, "Paladin ™ Rotator Cuff Anchor" [brochure], 2009, 2 pages total.
Conmed Linvatec, "Shoulder Restoration System" [brochure], 2009, 4 pages total.
Conmed Linvatec, "Shoulder Restoration System" [website], 2009, 1 page; retrieved from the Internet: <http://srs.linvatec.com/>.
Conmed Linvatec, "Shoulder Restoration System: PopLokTM Deployment Stages" [brochure], 2009, 2 pages total.
Conmed Linvatec, "Spectrum® II Soft Tissue Repair System" [brochure], 2006, 4 pages total.
Conmed Linvatec, "Spectrum® MVPTM" [brochure], 2008, 4 pages total.
Conmed Linvatec, "Super Shuttle™" [brochure], 2009, 2 pages total.
Covidien AG, "HerculonTM Soft Tissue Fixation System—Bringing greater pull-out strength to rotator cuff repair" [brochure], 2008, 4 pages total.
Daculsi et al., "Current State of the Art of Biphasic Calcium Phosphate Bioceramics," Journal of Materials Science, Mar. 2003; 14(3):195-200.
Depuy Mitek, Inc, a Johnson & Johnson Company, "Biocryl Rapide—TCP/PLGA Composite" [brochure], 2007, 4 pages total.
Depuy Mitek, Inc, a Johnson & Johnson Company, "BioKnotlessTM RC Suture Anchor: Rotator Cuff Repair Surgical Technique" [brochure], 2006, 6 pages total.
Depuy Mitek, Inc, a Johnson & Johnson Company, "Dual Threaded Suture Anchor Healix PEEKTM" [brochure], 2009, 2 pages total.
Depuy Mitek, Inc, a Johnson & Johnson Company, "ExpresSewTM Flexible Suture Passer" [instructions for use], Aug. 2007, 124 pages total.
Depuy Mitek, Inc, a Johnson & Johnson Company, "ExpresSewTM II Flexible Suture Passer" [instructions for use], Oct. 2006, 105 pages total.
Depuy Mitek, Inc, a Johnson & Johnson Company, "ExpresSewTM II: Surgical Technique" [brochure], 2007, 8 pages total.
Depuy Mitek, Inc, a Johnson & Johnson Company, "ExpresSewTM Surgical Technique" [brochure], 2005, 2 pages total.
Depuy Mitek, Inc, a Johnson & Johnson Company, "ExpresSewTM: A Single-Step Passer Under 5 mm" [brochure], 2005, 2 pages total.
Depuy Mitek, Inc, a Johnson & Johnson Company, "Healix BRTM" [brochure], 2009, 2 pages total.
Depuy Mitek, Inc, a Johnson & Johnson Company, "Healix PEEKTM—Dual Threaded Suture Anchor" [brochure], 2009, 2 pages total.
Depuy Mitek, Inc, a Johnson & Johnson Company, Lupine ™ BR & BioknotlessTM BR Anchors . . . Now with Biocryl Rapide—Biocryl Rapide has refined our Suture Anchors as "Bio-Replaceable" [brochure], 2007, 4 pages total.
Depuy Mitek, Inc, a Johnson & Johnson Company, "Mitek Suture Grasper" [instructions for use], 2007, 60 pages total.
Depuy Mitek, Inc, a Johnson & Johnson Company, "Palenlok® RC—Quick Anchor Plus® Absorbable" [brochure] 2006, 2 paages total.
Depuy Mitek, Inc, a Johnson & Johnson Company, PathSeekerTM Flexible Suture Grasper [brochure], 2005, 2 pages total.
Depuy Mitek, Inc, a Johnson & Johnson Company, "PathSeekerTM Suture Passer" [instructions for use], 2007, 174 pages total.
Depuy Mitek, Inc, a Johnson & Johnson Company, Procedural Solutions in Shoulder Repair [advertorial and detail],2005; retrieved from the Internet: <http://issuu.com/valmaass/docs/mitek_advertorial?mode=a_p.
Depuy Mitek, Inc, a Johnson & Johnson Company, "Quick Anchor® Plus Family" [brochure], 2005, 2 pages total.
Depuy Mitek, Inc, a Johnson & Johnson Company, SpiraLokTM Absorbably Dual-Eyelet Theaded Suture Anchor [brochure], 2005, 2 pages total.
Depuy Mitek, Inc, a Johnson & Johnson Company, VersalokTM Anchor [instructions for use], Aug. 2007, 92 pages total.
Dines et al., "Horizontal Mattress With a Knotless Anchor to Better Recreate the Normal Superior Labrum Anatomy," Arthroscopy, Dec. 2008;24(12):1422-1425.
Esch, "Arthroscopic Rotator Cuff Repair with the Elite™ Shoulder System," A Smith & Nephew Techique Plus ™ Illustrated Guide, 2001, 16 pages total.
Ethicon, Inc., a Johnson & Johnson Company, Mitek® Products BioknotlessTM Anchors: The First Absorbable Knotless Suture Anchor [brochure], 2007, 2 pages total.
Ethicon, Inc., a Johnson & Johnson Company, Mitek® Products, "Absorbable Soft Anchor PANALOK®" [brochure] 2001, 2 pages; can be retrieved from the Internet: <www.shoulderdoc.co.uk/documents/mitek_panalok.pdf >.
Fox et al., "Update on Articular Cartilage Restoration," Techniques in Knee Surgery, Mar. 2003; 2(1):2-17.
Gartsman et al., "Arthroscopic Rotator Cuff Repair," Techniques in Shoulder and Elbow Surgery, 1999, pp. 1-7.
Gartsman, "Arthroscopic Repair of Full-Thickness Tears of the Rotator Cuff," The Journal of Bone and Joint Surgery, 1998; 80:832-840.
Gartsman, Shoulder Series Technique Guide: Bankart Repair Using the Smith & Nephew Bioraptor 2.9 Suture Anchor [brochure], Smith & Nephew, Inc., Sep. 2004, Rev. A, 7 pages total; retrieved from the Internet: <http://global.smith-nephew.com/cps/rde/xber/smithnephewls/V1-1061563A_bioraptorpdf.
Gill, The Treatment of Articular Cartilage Defects Using Microfracture and Debridement, Am J Knee Surg 2000;13(1):33-40.
Green et al., "Arthroscopic versus open Bankart procedures: a comparison of early morbidity and complications," Arthroscopy, 1993; 9(4):371-374.
Guanche et al., "Labral Repair" [video recording], A young track athlete with a pincer lesion in her hip undergoes an arthroscopic labral takedown and repair by Carlos Guanche, MD at Southern California Orthopedic institute in Van Nuys, CA. Dr. Guanche performs complex hip arthroscopic procedures including resection of cam lesions, labral repairs, psoas releases and abductor repairs, posted on the Internet: <http://www.youtube.com/watch?v=onCIESDRVZM&feature=channel_page> on Jun. 18, 2008.
Guanche, "Large Hip Labral Repair Using PushLockTM Anchor" [video recording], Arthroscopic surgery of a hip labral repair with a knotless anchor performed by Dr. Carlos Guanche in Van Nuys, CA, posted on the Internet: <http://www.youtube.com/watch?v=t04fj2TcXv0>on Mar. 25, 2008.
Halbrecht, "Versalok: A New technique for Arthroscopic Knotless Rotator Cuff Repair" [presentation], Mitek Sponsored Dinner Meeting. Tuscon AZ. Jun. 5, 2007; retrieved from the Internet: <http://www.iasm.com/pdfs/KnotlessArthroscopicRotatorCuffRepairUsingVersalok.pdf>, 44 pages total.
Hughes, The Kinematics and Kinetics of Slipknots for Arthroscopic Bankart Repair, Am J Sports Med, Nov. 2001; 29( 6):738-745.
International search report and written opinion dated Jul. 2, 2010 for PCT/US2010/034118.
International search report and written opinion dated Jul. 2, 2010 for PCT/US2010/034104.

(56) References Cited

OTHER PUBLICATIONS

International search report and written opinion dated Jul. 9, 2010 for PCT/US2010/034115.
Jeys et al., "Bone Anchors or Interference Screws? A Biomechanical Evaluation for Autograft Ankle Stabilization," Am J Sports Med, Oct. 2004; 32( 7):1651-1659.
KFX® Medical, Arthroscopic Double Row Rotator Cuff Repair [procedural Video], Performed by Joe Thum, M.D., Toms River, NJ; can be view at: <http://www.kfxmed ical. com/tech nology_proced u re. htm>.
KFX® Medical, "Arthroscopic PASTA lesion repair using the SutureCross® System" [procedural Video] Performed by Joe Tauro, M.D., Toms River, NJ; can be view at: <http://www.kfxmedical.com/technology_procedure_pasta_video.htm.
KFX® Medical, "SutureCross® Knotless Anatomic Fixation System: Double Row Fixation for Rotator Cuff Repair Animation" [video screenshots] 2008, 52 pages total.; video available online at <http://www.kfxmedical.com/video/SURGTECH9-23.wmv>.
KFX® Medical, "SutureCross® Knotless Anatomic Fixation System: Double Row Fixation Rotator Cuff Repair Surgical Technique" [brochure], 2008, 12 pages total.
KFX® Medical, "SutureCross® Knotless Anatomic Fixation System: Double Row Rotator Cuff Fixation" [website] ; retrieved from the Internet: <http://www.kfxmedical.com/product_suturecross.htm>, 1 page.
KFX® Medical, "SutureCross® Knotless Anatomic Fixation System: Rotator Cuff Repair" [datasheet], 2008, 2 pages total.
KFX® Medical, The PASTAFxTM System Surgical Technique: Simplified PASTA Rotator Cuff Repair [technique guide], 2008, 8 pages total.
KFX® Medical, The PASTAFxTM System: No need to Tear to Repair [website]; retrieved from the internet: <http://www.kfxmedical.com/product_pastafx.htm>, 2 pages total.
KFX® Medical, The PASTAFxTM System: Simplified PASTA Repair [datasheet] 2008, 2 pages total.
Khabie et al., "Fixation Strength of Suture Anchors After Intraoperative Failure of the First Anchor," 45th Annual Meeting of Orthopaedic Research Society, Feb. 1-4, 1999, Anaheim, p. 1074 ; retrieved from the Internet: <http://www.ors.org/web/Transactions/45/1074.PDF>.
Langdown et al., In Vivo Evaluation of 6-TCP Bone Graft Substitutes in a Bilateral Tabial Defect Model, Paper No. 1712, 52nd Annual Meeting of the Orthopaedic Research Society, The Lakeside Center, McCormick Place, Chicago, IL, Mar. 19-22, 2006, 1 page total.
Larson et al., "Arthroscopic Management of Femoroacetabular Impingement: Early Outcomes Measures," Arthroscopy. May 2008;24(5):540-546.
Linvatec, "Course: Bio-Anchor® Surgical Technique" [Slideshow], 2004, 13 pages; retrieved from the Internet: <http://www.conmed.com/SurgicalTechniques/BioAnchor.swf>.
Linvatec, a Conmed® Company, "Bio-Anchor® Surgical Technique: Shoulder Instability System" [brochure], 2004, 2 pages; retrieved from the Internet: <http://www. con med. com/PDF%20files/CST%203021%20Rev%201%20BioAnchorST.pdf.
Linvatec, a Conmed® Company, "ImpactTM Suture Anchor Surgical Technique" [brochure], 2004, 4 pages total.
Lo et al., "Abrasion Resistance of Two Types of Nonabsorbable Braided Suture," Arthroscopy, Apr. 2008; 20(4):407-413.
Lo et al., "Arthroscopic Knots: Determining the Optimal Balance of Loop Security and Knot Security," Arthroscopy. May 2004;20(5):489-502.
Louden et al., "Tendon Transfer Fixation in the Foot and Ankle: A Biomechnanical Study Evaluating Two Sizes of Pilot Holes for Bioabsorbable Screws," Foot & Ankle International, Jan. 2003; 24(1):67-72.
Ma et al., "Biomechanical Evaluation of Arthroscopic Rotator Cuff Stitches," The Journal of Bone and Joint Surgery, 2004; 86:1211-1216.

McGuire et al., "Bioabsorbable Interference Screws for Graft Fixation in Anterior Cruciate Ligament Reconstruction," Arthroscopy, Jul. 1999; 15(5):463-473.
Menche et al., "Inflammatory Foreign-Body Reaction to an Arthroscopic Bioabsorbable Meniscal Arrow Repair," Arthroscopy. Oct. 1999;15(7):770-772.
Meyer et al., "Mechanical Testing of Absorbable Suture Anchors," Arthroscopy, Feb. 2003; 19(2):188-193.
Middleton et al., "Synthetic Biodegradable Polymers as Orthopedic Devices," Biomaterials, Dec. 2000, 21(23):2335-2346.
Millett et al., "Mattress Double Anchor Footprint Repair: A Novel, Arthroscopic Rotator Cuff Repair Technique," Arthroscopy Oct. 2004; 20(8):875-879.
Morgan, "Arthroscopic Management of Rotator Cuff Tears" [Presentation Outline], The Morgan Kalman Clinic, Wilmington, Delaware, undated, 2 pages.
Murray, Jr., "Arthroscopic Rotator Cuff Repair with a Bio absorbable Suture Anchor: Preliminary Results," [Abstract] Orthopaedic Associates of Portland, Portland, ME, 1 page.
Ogose et al., "Histological Assessment in Graft of Highly Purified Beta-Tricalcium Phosphate (Osferion) in Human Bones," Biomaterials. Mar. 2006;27(8):1542-1549.
Ogose et al., "Histological Examination of 6-Tricalcium Phosphate Graft in Human Femur," J Biomed Mater Res, 2002;63(5):601-604.
Parcus Medical, LLC, "Parcus V-LoxTM PEEK CF Suture Anchor", pp. 15, 16 of 510(k) Summary, FDA Approval Letter and Indications of Use for 510(k) No. K091094, Sep. 2009, 5 pages total.
Parcus Medical, LLC, "PEEK CF V-LoxTM Suture Anchor Demo" [video]; can be view at: <http://www.parcusmedical.com/techniques/animations/peek-vlox-anchor-demo.html>.
Parcus Medical, LLC, "V-LoxTM PEEK CF Suture Anchor [Production Information and Directions for use", undated, 2 pages total.
Parcus Medical, LLC, "V-LoxTM PEEK CF Suture Anchors Product Information Sheet" [brochure] undated, 1 page total.
Parcus Medical, LLC, "V-LoxTM PEEK CF Suture Anchors" [website]; retrieved from the Internet: <http://www.parcusmedical.com/products/peek-anchor.html>, 2 pages total.
Park et al., ""Transosseous-Equivalent" Rotator Cuff Repair Technique," Arthroscopy, Dec. 2006; 22(12):1360.e1-1360.e5.
Romeo et al., "Arthroscopic Repair of Full-Thickness Rotator Cuff Tears: Surgical Technique and Instrumentation" Orthopedic Special Edition, 2001; 7(1 of 2):25-30; retrieved from the Internet: <http://www.cartilagedoc.org/downloads/shoulder/Rotat.pdf>.
Schamblin, Conexa® Case Series Report: Arthroscopic Reinforcement of Revision Rotator Cuff Repair Tornier, Inc., 2009, 2 pages; retrieved from the Internet: <www.bhportho.com/docs/Conexa_RCR_Repair_Schamblin.pdf>.
Smith & Nephew, Inc., "2008 Product Catalog" [catalog], 2009, 311 pages total.
Smith & Nephew, Inc., "2009 Product Catalog" [catalog], 2008, 373 pages total.
Smith & Nephew, Inc., "ACCY-PASS Suture Shuttle" [video animation] 2005, 59 image screen shots; can be view at : <http://endo.smith-nephew.com/fr/View.asp?guid={6F27C42E-1632-4974-84E9-F18922FC19AA} &b=2->.
Smith & Nephew, Inc., Bioraptor 2.9 Suture Anchor [video animation], 2004; can be viewed at: <http://endo.smith-nephew.com/fr/View.asp?guid={98BCCE86-B5C2-413F-80AE¬CF7260A38C17} &b=2-BIORAPTOR%20 animation. wmv>.
Smith & Nephew, Inc., "Bioraptor 2.9" [website], 3 pages total; retrieved from the Internet: <http://endo.smith-nephew.com/fr/node.asp?Nodeld=3608>.
Smith & Nephew, Inc., "Bioraptor PK suture Anchor", 510(k) Summary, FDA Approval Letter, and Indications of Use for 510(k) No. K071586, Aug. 2007, 5 pages total.
Smith & Nephew, Inc., "ELITE PASS Premium Arthroscopic Suture Shuttle" [video animation], Mar. 2005, 44 image screen shots; video can be viewed at: <http://global.smith-nephew.com/us/showfile.xml?doc=V1-ELITE_PASS_Animation(26)_.wmv>.
Smith & Nephew, Inc., "FOOTPRINT PK Suture Anchor: Arthroscopic Shoulder Repair Using the Smith & Nephew FOOTPRINT PK Suture Anchor" [brochure], 2008, 12 pages total.

(56) References Cited

OTHER PUBLICATIONS

Smith & Nephew, Inc., "KINSA* Suture Achnor" [website], 2 pages; retrieved from the Internet: <http://www.endo.smith-nephew.com/fr/node.asp?NodeId=3739>.

Smith & Nephew, Inc., "OsteoraptorTM Suture Anchor", pp. 10-11 of 510(k) Summary, FDA Approval Letter, and Indications of Use for 510(k) No. K082215, Nov. 2008, 5 pages total.

Smith & Nephew, Inc., "TWINFIX Suture Anchors with ULTRABRAID Suture—Unparalleled strength, superior handling" [brochure], 2005, 12 pages total.

SmithNephew. Shoulder Series Technique Guide: Arthroscopic Shoulder Repair Using the Smith & Nephew Kinsa Suture Anchor [brochure], Smith & Nephew, Inc., Sep. 2006, Rev. B, 12 pages total; retrieved from the Internet: <http://global.smith-nephew.com/cps/rde/xbcr/smithnephewls/V1-10600180b%2829%29.pdf.

Spiralok and-Bio-Corkscrew FT Cadaver Study [white paper], no publication information, 2 pages total.

Stryker Corporation, "PEEK TwinLoop" [website], 1 page; retrieved from the Internet: <http://www.strykercom/enus/products/Orthopaedics/SportsMedicine/ShoulderInstrumentation/Anchors/Peek/056652.

Stryker Corporation, "Point to the Solution: BioZip Absorbable Suture Anchor" [brochure,] 2008, 4 pages total.

Stryker Corporation, "Shoulder Repair Made Simpler: Champion Shoulder Instrumentation" [brochure], 2008, 4 pages total.

Stryker Corporation, Strength & Flexibility in Soft-Tissue Repair [brochure], 2008, 4 pages total.

Stryker Corporation, Stronger Than Ever: PEEK Zip Anchor [brochure] 2008, 4 pages total.

Stryker Corporation, "Suture Sliding Made Simple" [brochure], 2005, 4 pages total.

Stryker Corporation, One Shot for Success—Titanium Wedge Anchor [brochure], 2008, 4 pages total.

Stryker. Stability, Precision, Flexibility—PEEK Twinloop Anchor [brochure], Stryker Corporation, Jun. 2008, Rev 1, 4 pages total; retrieved from the Internet: <http://www.strykercom/stellent/groups/public/documents/web_prod/056750.pdf>.

Tetik et al., "Bioabsorbable Interference Screw Fixation in a Bone Tunnel: Comparison of 28mm; 35 \mm Single Screw Fixation and Bi-Cortical Fixation with a 20mm and 17mm Screws," Lexington, Kentucky, undated, 3 pages total.

Tornier, Inc., "CINCHTM Knotless Fixation Implant System", pp. 38-40 of 510(k) Summary, FDA Approval Letter and Indications of Use for 510(k) No. K080335, Feb. 2008, 6 pages total.

Tornier, Inc., "InsiteTM Suture Anchors", pp. 66-67 of 510(k) Summary, FDA Approval Letter and Indications of Use for 510(k) No. K080368, Feb. 2009, 5 pages total.

Tornier. Piton Knotless Fixation System, Tornier, Inc., 2009, 3 pages total; retrieved from the Internet: <http://www.tornier-us.com/sportsmed/smd003/index.php?pop=1> on Oct. 14, 2009.

Vogt et al., "Injuries to the Articular Cartilage," European Journal of Trauma, Aug. 2006; 32(4):325-331.

Walsh et al., "Healing of a Critical Size Defect in Sheep Using Bone Graft Substitutes in Block Form," Poster No. 1433, 53rd Annual Meeting of the Orthopaedic Research Society, San Diego Convention Center, San Diego, California, Feb. 11-14, 2007, 1 page total.

Warden et al., "Magnetic Resonance Imaging of Bioabsorbably Polylactic Acid Interference Screws During the First 2 Years After Anterior Cruciate Ligament Reconstruction," Arthroscopy, Jul.-Aug., 15(5):474-480.

Weiler et al., "Biodegradable Implants in Sports Medicine: The Biological Base," Arthroscopy, Apr. 2000;16(3):305-321.

Yanke et al., 'Arthroscopic Double-Row and "Transosseous-Equivalent" Rotator Cuff Repair,' Am J Orthop (Belle Mead NJ). Jun. 2007;36(6):294-297.

Zimmer, Inc., "Labral Repair with Statak Suture Anchors—Surgical Techniques: Arthroscopic & Open" [brochure], 1996, 6 pages total.

Zimmer, Inc., "Rotator Cuff Repair with Statak Suture Anchors—Surgical Techniques: Arthroscopic & Open" [brochure], 1996, 6 pages total.

Office action dated Jun. 5, 2009 for U.S. Appl. No. 12/605,065.
Office action dated Oct. 4, 2012 for U.S. Appl. No. 12/776,225.
U.S. Appl. No. 14/585,654, filed Dec. 30, 2014, Hirotsuka et al.
Office action dated Dec. 5, 2014 for U.S. Appl. No. 13/692,596.
European search report and search opinion dated Apr. 15, 2016 for EP Application No. 10775301.4.
Notice of allowance dated Mar. 31, 2016 for U.S. Appl. No. 13/749,038.

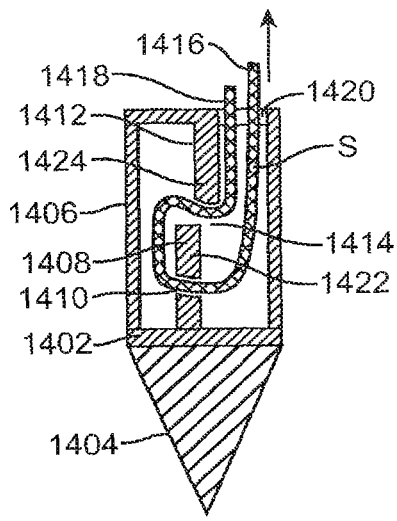
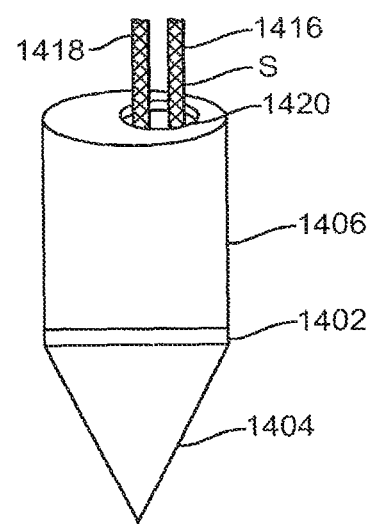
FIG. 25A          FIG. 25B
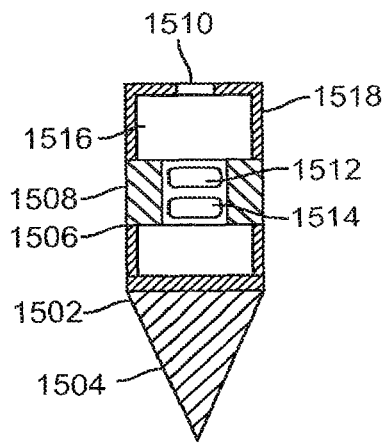
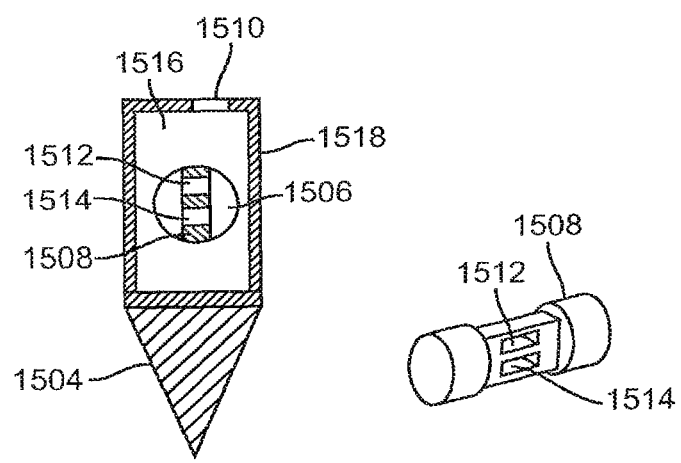
FIG. 26A          FIG. 26B          FIG. 26C

SEC A-A

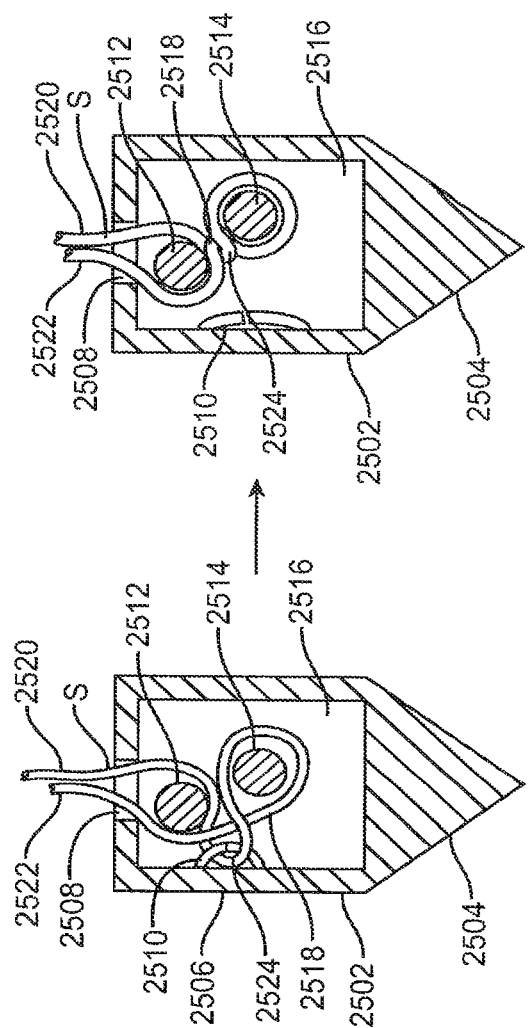

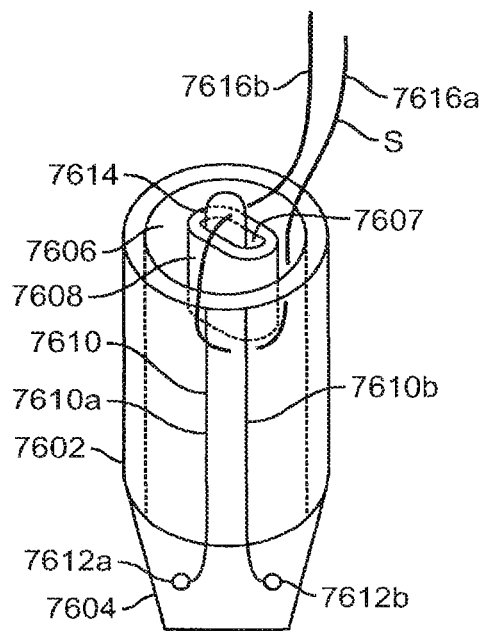
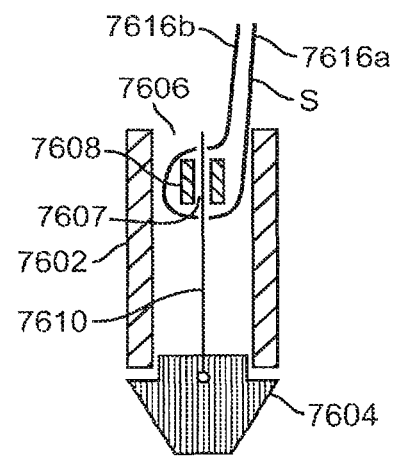
FIG. 51A    FIG. 51B
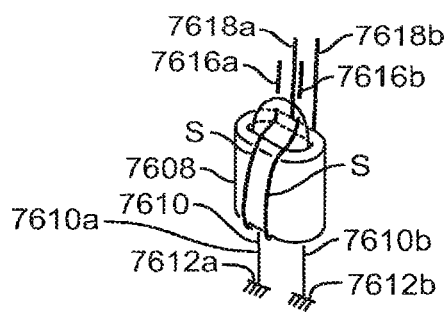
FIG. 51C

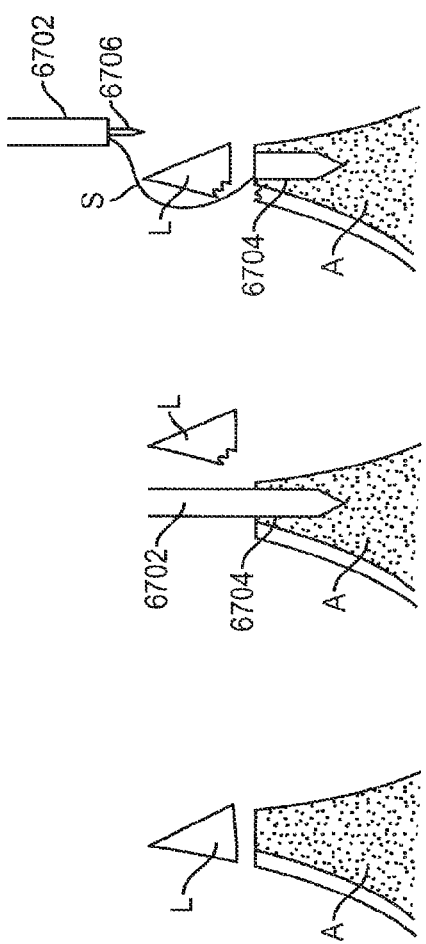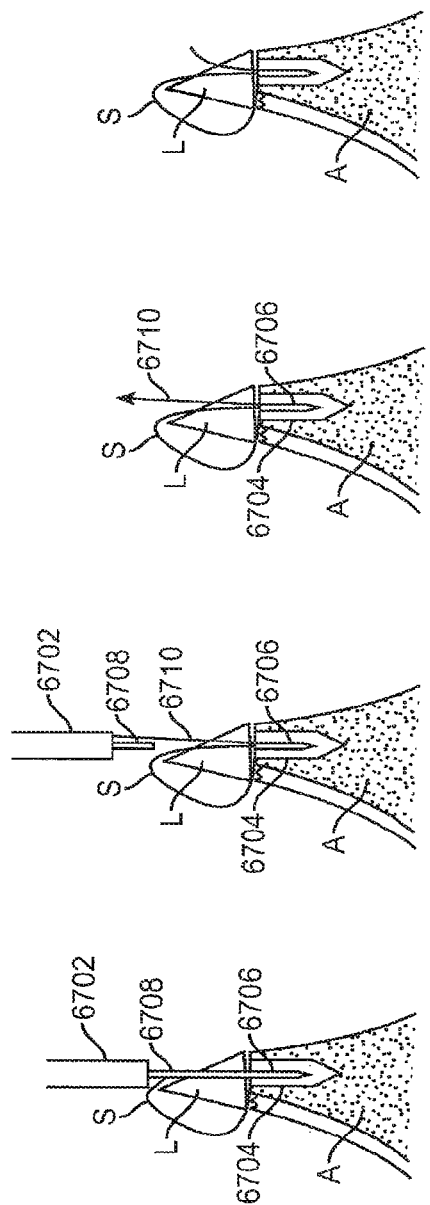

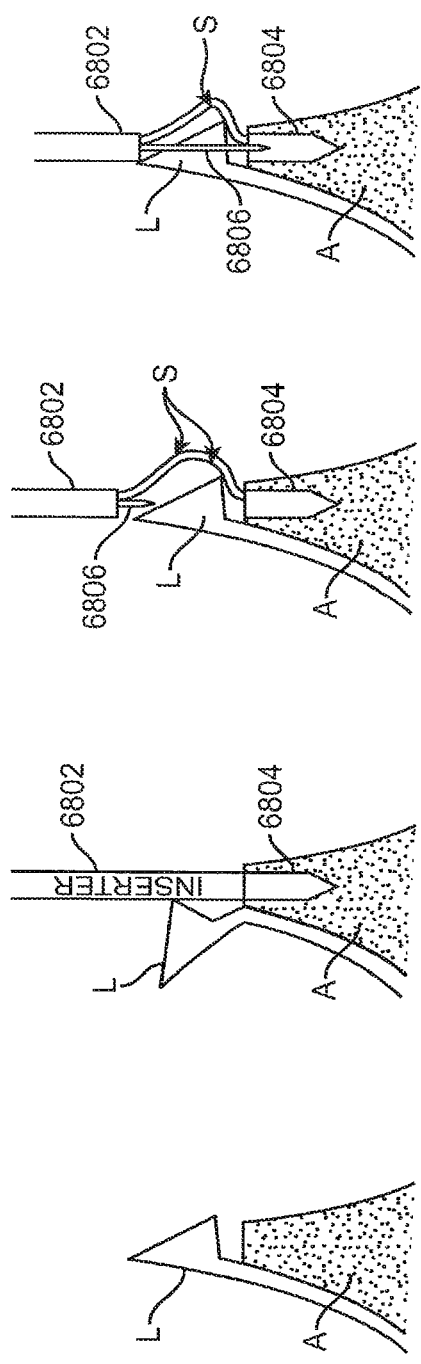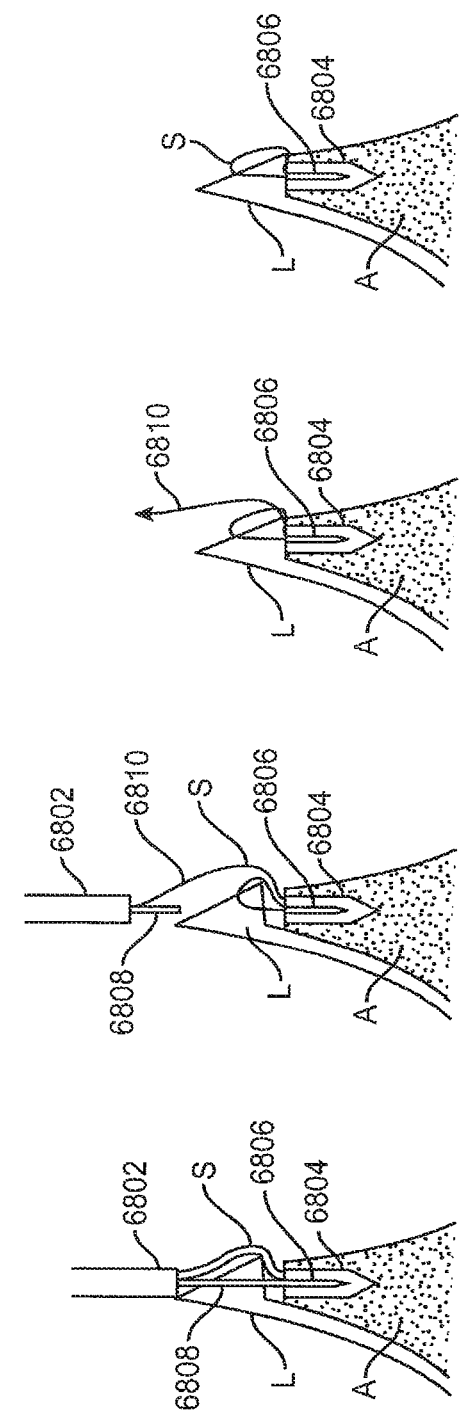

KNOTLESS SUTURE ANCHOR AND METHODS OF USE

CROSS-REFERENCES TO RELATED APPLICATIONS

The present application is a continuation of U.S. patent application Ser. No. 12/776,225, filed May 7, 2010, which is a non-provisional of, and claims the benefit of U.S. Provisional Patent Application Nos. 61/177,602, filed May 12, 2009; 61/219,290, filed Jun. 22, 2009; 61/263,728, filed Nov. 23, 2009; 61/263,751, filed Nov. 23, 2009; 61/298,780, filed Jan. 27, 2010; and 61/304,352, filed Feb. 12, 2010; the entire contents of each of the above listed patent applications is incorporated herein by reference.

The present application is also related to U.S. patent application Ser. No. 12/605,065, filed Oct. 23, 2009; U.S. patent application Ser. No. 12/776,177, filed May 7, 2010; and U.S. patent application Ser. No. 12/776,208, filed May 7, 2010; the entire contents of which are incorporated herein by reference.

BACKGROUND OF THE INVENTION

1. Field of the Invention

The present disclosure relates to medical devices, systems and methods, and more specifically to methods, systems and devices used for knotless suturing of tissue.

Soft tissue such as tendons, ligaments and cartilage are generally attached to bone bysmall collagenous fibers which are strong, but which nevertheless still can tear due to wear or disease. Examples of musculoskeletal disease include a torn rotator cuff as well as a torn labrum in the acetabular rim of a hip joint or the glenoid rim in a shoulder joint.

Thus, treatment of musculoskeletal disease may involve reattachment of torn ligaments, tendons or other tissue to bone. This may require the placement of devices such as suture anchors within bone. A suture anchor is a device which allows a suture to be attached to tissue such as bone. Suture anchors may include screws or other tubular fasteners which are inserted into the bone and anchored in place. After insertion of the anchor, the tissue to be repaired is captured by a suture, the suture is attached to the anchor (if not already pre-attached), tension is adjusted, and then the suture is often knotted so that the tissue is secured in a desired position.

Most conventional suture anchors require the surgeon to tie knots in the suture to secure the target tissue to the bone after the anchor is placed. Knot tying can be difficult during surgery, particularly if working in a confined space through cannulas or other surgical ports as in arthroscopic surgery. Therefore, it would be desirable to provide knotless suture anchor systems.

Additionally, many surgeons prefer to use polymeric anchors rather than metal ones so that the anchors are compatible with the use of MRI. While polymeric anchors are available, they do not have the knotless suture securing capabilities described above. This may be in part due to challenges of fabricating polymer anchors that provide a reliable cinching mechanism for a knotless anchor at the small scale required for orthopedic procedures. Further, while it is frequently advantageous to fabricate polymeric devices by molding, known knotless anchor designs require multiple moving parts and geometries which are not suitable for molding. Therefore it would be advantageous to provide a knotless anchor with the characteristics described above and which is also suitable to being molded with a polymer as a single integral part or as series of molded components that can be easily assembled together. By single integral part, it is meant that the entire part is formed from a single piece of material or molded as a single piece, without need for fastening, bonding, welding or otherwise interconnecting multiple components together. Examples of this include, but are not limited to, single-piece components that are injection molded, cast, or machined from a single block of material. The word "molded" is intended to encompass materials which are injection molded, blow molded, compression molded, thermoformed, or made using other molding processes known to those of skill in the art, useful for shaping polymers, ceramics, or other formable materials.

Frequently two or more anchors and multiple lengths of suture are required. Using such devices can be time consuming and difficult to undertake in the tight space encountered during endoscopic surgery and sometimes even in conventional open surgery. Recently, knotless suture anchors having suture clamping mechanisms have been developed to eliminate the need to tie knots but they still can be difficult or awkward to use.

Some knotless suture anchors have been devised which allow the suture to be cinched and secured without tying a knot, however these typically rely upon trapping the suture between the anchor and the bone to secure the suture, which means the anchor cannot be fully inserted into the bone until the tissue has been captured and secured tightly. The process of maintaining tension on the suture, keeping the tissue at the desired location and simultaneously inserting the anchor into the bone is difficult. Other knotless anchors rely on the manual actuation of some type of moving part on the anchor to clamp or trap the suture within the anchor, requiring an extra hand that the surgeon may not have available. It would be desirable to allow the anchor to be fully inserted in the bone prior to securing the tissue and to avoid the requirement of extra manipulations to secure the suture.

Thus, it would be desirable to provide improved knotless suture anchors that are easier to use and also that may take up less space during deployment and that are easier to deploy.

In particular, treating musculoskeletal disease in a hip joint can be especially challenging. The hip joint is a deep joint surrounded by a blanket of ligaments and tendons that cover the joint, forming a sealed capsule. The capsule is very tight thereby making it difficult to advance surgical instruments past the capsule into the joint space. Also, because the hip joint is a deep joint, delivery of surgical instruments far into the joint space while still allowing control of the working portions of the instrument from outside the body can be challenging. Additionally, the working space in the joint itself is very small and thus there is little room for repairing the joint, such as when reattaching a torn labrum to the acetabular rim. Moreover, when treating a torn labrum, the suture anchor must be small enough to be inserted into the healthy rim of bone with adequate purchase, and the anchor also must be short enough so that it does not protrude through the bone into the articular surface of the joint (e.g. the acetabulum). Existing anchors may be used to repair the labrum, but are not well-suited to labral repair especially in the hip. First, the reattachment of the labrum to the acetabular rim is most effective if both ends of the suture are attached to the same point in the bone. This provides the most precise and secure apposition of the labrum to the rim. The space available on the acetabular rim is very limited, typically requiring an anchor with a transverse dimension (e.g. diameter) preferably less than 4 mm and no more than about 3.5 mm and therefore many commercially available anchors are too large. Thus, it would be desirable to provide suture anchors that have a small diameter and length.

Additionally, existing knotless anchors are typically designed for use in rotator cuff repair in the shoulder and they are intended for placement in separate holes in the bone. These devices have no mechanism for coupling one anchor to the other within the same hole, cannot be implanted concentrically within the hole, and are too long for stacking within the same hole. Further, many existing knotless anchors are too large for placement on the acetabular rim for labral repair of the hip.

In addition, existing knotless anchors and interconnecting anchors have suture locking mechanisms which have moving parts and other complex designs that are not reliably manufacturable at the small scale required for labral repair anchors. While various types of anchors with suture locking mechanisms have been disclosed, many of these cannot be made in an anchor less than 4 mm, and no more than 3.5 mm in diameter.

Moreover, because of the difficulty of performing labral repairs arthroscopically, it is highly desirable to minimize the manipulations of the suture and anchor that are required intraoperatively. Many existing knotless anchors require the surgeon, after initial anchor placement and capture of the labrum, to thread the free end of the suture through the anchor or a component of the anchor, which is difficult and takes an excessive amount of time. Some anchors further require the surgeon to push the anchor further into bone, or push a locking mechanism on the anchor, or perform some other manipulation of the anchor in order to lock the suture. These manipulations add difficulty and time to arthroscopic labral repair that would be desirably avoided.

Therefore, it would be desirable to provide improved knotless suture anchors that are ideally suited to arthroscopic procedures, and in particular labral repair in the hip. The anchors would preferably be adapted for placement in a single hole in the bone, extremely simple in design with few or no moving parts, manufacturable at very small scale (e.g. diameter less than 4 mm, and preferably no more than 3.5 mm), and require no manipulation of the suture or the anchor itself in order to operate the suture locking mechanism. The anchors should further require no intraoperative threading of the suture ends or other manipulation of the suture either before or after initial anchor placement.

Thus, there is a need for improved devices, systems and methods which overcome some of the aforementioned challenges. At least some of these objectives will be met by the inventions described hereinbelow.

2. Description of the Background Art

Patents disclosing suture anchoring devices and related technologies include U.S. Pat. Nos. 7,566,339; 7,390,329; 7,309,337; 7,144,415; 7,083,638; 6,986,781; 6,855,157; 6,770,076; 6,767,037; 6,656,183; 6,652,561; 6,066,160; 6,045,574; 5,810,848; 5,728,136; 5,702,397; 5,683,419; 5,647,874; 5,630,824; 5,601,557; 5,584,835; 5,569,306; 5,520,700; 5,486,197; 5,464,427; 5,417,691; and 5,383,905. Patent publications disclosing such devices include U.S. Patent Publication Nos. 2009/0069845 and 2008/0188854 and PCT Publication No. 2008/054814.

SUMMARY OF THE INVENTION

The present invention provides devices, systems and method for knotless suturing of tissue. Exemplary procedures where knotless suturing may be advantageous include repair of torn rotator cuffs, as well as a torn labrum in the acetabular rim of a hip joint or the glenoid rim in a shoulder joint. The invention relates to suture anchors for anchoring sutures to bone, and more specifically provides a suture anchor which eliminates the need for knotting the suture and which is suited to being a molded polymer construction. The anchors will find particular utility in hip and shoulder arthroscopy, e.g. labral reattachment and similar procedures.

In a first aspect of the present invention, a knotless suture anchoring system comprises a first anchor positionable in tissue and having a longitudinal axis. The system also has a cinching mechanism coupled to the first anchor. The cinching mechanism comprises a body having first and second transverse apertures spaced apart along the longitudinal axis and separated by a bar. A length of suture is threaded through the first and second apertures so as to form a loop around the bar. The suture has first and second extremities extending respectively from the first and second apertures on the same side of the body, and the first and second extremities are generally parallel to and lie over one another such that the second extremity is sandwiched between the first extremity and the body. Exerting tension on the first extremity compresses the second extremity against the body to prevent movement of the suture relative to the body. Also, exerting tension on the second extremity allows the suture to move longitudinally relative to the body.

The suture may comprise a flat cross-sectional profile, a round cross-sectional profile, or any other profile. The anchor has a proximal end, a distal end, and the longitudinal axis extends therebetween. The first and second apertures may extend through the body in a direction transverse to the longitudinal axis. The central channel may be aligned with the longitudinal axis, and the channel may have an opening at the proximal end. At least one of the first and second extremities of suture may extend through the opening. The cinching mechanism may be positioned in a central channel of the anchor. The apertures may be disposed along the body in a single line substantially parallel with the longitudinal axis. The body may comprise a plate and the first and second apertures comprise slots extending through the plate. The plate may be oriented generally parallel to the longitudinal axis. The plate may be disposed in a central channel of the anchor.

The body may have a face against which the second extremity is compressed, and the bar may be laterally offset from the face. The first aperture may intersect the face so as to define a corner which engages the second extremity. The corner may have an edge which locks the second extremity when the first extremity is tensioned. The corner may define an angle of no more than about 90 degrees. The face may comprise one or more features to induce friction with the second extremity when the first extremity is tensioned.

The body may comprise a barrel disposed in an aperture in a sidewall of the anchor transverse to the longitudinal axis of the anchor. The barrel may be rotatably disposed in the sidewall aperture, and the rotatable barrel may have a locked position and an unlocked position. The unlocked position may allow the suture to move, and the locked position may constrain movement of the suture. The apertures may extend through the barrel parallel to a first axis, and in the unlocked position, the first and second extremities may extend from the apertures substantially parallel to the first axis. In the locked position, the first and second extremities extend from the apertures in a direction transverse to the first axis.

The cinching mechanism may be a single molded part, and may be integral with the first anchor. The cinching mechanism and the first anchor may be a single molded part. The cinching mechanism may be on a separate member that is configured to be attached to the first anchor at a surgical site. The cinching mechanism may be coupled to a second anchor adapted for positioning in tissue and which may be coupled to the first anchor. The cinching mechanism may require no movement of parts relative to the first anchor to prevent the suture from moving when the first extremity is tensioned.

The first anchor may have an outer diameter which is less than 4 mm and no more than about 3.5 mm along its entire length. The system may further comprise a second anchor that is positionable in the tissue. One of the two anchors may be positionable concentrically in the other of the two anchors, or one of the two anchors may be positioned end to end with the other of the two anchors.

In another aspect of the present invention, a knotless suture anchoring system comprises a first anchor component having a longitudinal axis and a first cinching mechanism. A second anchor component is initially detached from the first anchor component, and at least one of the first and second anchor components are adapted for placement directly into bone or other tissue and comprise a retention feature on an exterior surface thereof for retaining the first or second anchor component in the bone or tissue. The system also has a coupling mechanism for coupling the second anchor component to the first anchor component, and a length of suture at least partially disposed in the first cinching mechanism. The suture has a free end, and the first cinching mechanism allows the suture to pass through the first cinching mechanism in a first direction when the free end is tensioned and constrains movement of the suture through the first cinching mechanism in a second direction opposite the first direction.

The second anchor component may be received within a cavity in the first anchor component. The first anchor component may be received within a cavity in the second anchor component. The first anchor component may be coupled end-to-end with the second anchor component. The suture may have a second end coupled to the second anchor component. The first cinching mechanism may have no parts movable relative to the first anchor component. The system may further comprise a second cinching mechanism coupled to the second anchor component. The suture may have a second end that is coupled to the second cinching mechanism. The second anchor component may have a suture retention structure for retaining a second end of the suture therein. The first anchor component and the first cinching mechanism may be an integral molded construction.

In another aspect of the present invention, a knotless suture anchoring system comprises a first anchor having a proximal end and a distal end, and being positionable in tissue. A second anchor also has a proximal end and a distal end, and a first cinching mechanism is coupled to either the first anchor or the second anchor. A coupling element is attached to one or both of the first and second anchors and is adapted to couple the first and the second anchors together end-to-end. A length of suture is coupled to either the first anchor or the second anchor. The suture has a free end and is at least partially disposed in the first cinching mechanism. The first cinching mechanism is adapted to allow the suture to be tensioned by pulling the free end so that the suture passes through the first cinching mechanism in a first direction while movement of the suture through the first cinching mechanism in a second direction opposite the first direction is constrained.

The coupling element may comprise a threaded post, and the first anchor may be threadably engaged with the second anchor. The coupling element may comprise a post having a plurality of barbs disposed thereon, or the coupling element may comprise a compression fitting. The suture may be fixed to the first anchor and the cinching mechanism may be on the second anchor. Each of the first and second anchors may be placed in tissue separately from the other of the first and second anchors.

In still another aspect of the present invention, a method for re-joining damaged tissue with substrate tissue comprises providing a suture coupled with a first anchor and a second anchor, and positioning the first anchor in the substrate tissue. The method also includes capturing the damaged tissue with the suture, and positioning the second anchor in the substrate tissue. The second anchor is axially aligned end-to-end with the first anchor. Adjusting the length of the suture apposes the damaged tissue with the substrate tissue.

The substrate tissue may comprise bone and the step of positioning the first anchor in the substrate tissue may comprise drilling a hole in the bone followed by positioning the first anchor therein. The step of positioning the first anchor may comprise advancing the first anchor from an elongate shaft of a delivery instrument. Capturing the damaged tissue may comprise at least partially encircling the damaged tissue with the suture. Capturing may also comprise passing at least one of the suture anchors through a penetration in the damaged tissue. Positioning the second anchor may comprise coupling the first anchor with the second anchor. Coupling the first and second anchors may comprise interconnecting a proximal region of the first anchor with a distal region of the second anchor. Coupling may also comprise engaging a plurality of threads or ribs on a proximal end of the first anchor with the second anchor. Adjusting the length of the suture may comprise pulling the suture through a cinching mechanism disposed in either the first or the second anchor. The cinching mechanism may be adapted to allow the suture to move in a first direction, while the suture is constrained from moving in a second direction opposite the first direction.

In another aspect of the present invention, a method for anchoring suture to substrate tissue comprises drilling a first hole into the substrate tissue, and placing a suture anchor into the first hole. The suture anchor is coupled to a first extremity of a suture. The method also includes capturing damaged tissue with the suture. The damaged tissue obstructs visualization of the first hole, so transmitting light through the damaged tissue allows visualization of the first hole through the tissue. A second extremity of the suture is then coupled to the first anchor.

The second extremity of the suture may be coupled to an anchor component and coupling the second extremity may comprise coupling the anchor component to the first anchor. The anchor component may be inserted concentrically in the first anchor, or the anchor component may be coupled end-to-end with the first anchor. At least one of the first anchor and the anchor component may have a cinching mechanism which allows the suture to move in a first direction and constrains the suture from moving in a second direction opposite the first direction. The method may comprise tightening the suture by pulling it through the cinching mechanism. The first anchor may be placed by means of a delivery instrument to which the first anchor is releasably coupled. The light may be transmitted from a light emission device coupled to the delivery instrument. The substrate tissue may comprise an acetabular or glenoid rim and the damaged tissue may comprise a torn labrum.

In another aspect of the present invention, a method for fabricating a suture anchor comprises molding the suture anchor from a polymer. The suture anchor may be of a unitary construction without moving parts and may have a cinching mechanism adapted to allow a suture to pass therethrough in a first direction while movement of the suture in a second direction opposite the first direction is constrained.

In yet another aspect of the present invention, a knotless suture anchoring system comprises a first anchor having a proximal end, a distal end, a central channel extending therebetween, and positionable in tissue. A tissue piercing needle is positionable in the central channel, and a first cinching mechanism is coupled to either the first anchor or the tissue piercing needle. A coupling element is attached to the first anchor or the tissue piercing needle. The coupling element is adapted to couple the first anchor and the tissue piercing needle together when the tissue piercing needle is positioned in the central channel. A length of suture is coupled to the first anchor and the tissue piercing needle. The suture has a free end and is at least partially disposed in the first cinching mechanism. The first cinching mechanism is adapted to allow the suture to be tensioned by pulling the free end so that the suture passes through the first cinching mechanism in a first direction while movement of the suture through the first cinching mechanism in a second direction opposite the first direction is constrained.

The suture may be tied to the first anchor and the first cinching mechanism may be coupled to the tissue piercing needle. The coupling element may comprise a snap fit between the tissue piercing element and the first anchor. The distal end of the first anchor may comprise a plurality of slits parallel with a longitudinal axis of the first anchor. The slits may form a plurality of deflectable arms in the anchor. An outer surface of the first anchor may comprise a plurality of barbs. The tissue piercing needle may comprise a central channel that is substantially parallel with a longitudinal axis of the needle. The suture may be fixedly attached to the tissue piercing needle, and the first cinching mechanism may be coupled with the first anchor.

In another aspect of the present invention, a method for re-joining damaged tissue with a substrate tissue comprises providing a suture anchor system having an anchor, a tissue piercing needle, and a suture coupled to the anchor and the needle. The anchor is positioned in the substrate tissue, and the damaged tissue is pierced with the needle. The suture is passed through the damaged tissue, and the needle is coupled with the anchor. Suture length is then adjusted so that the damaged tissue is apposed with the substrate tissue.

The substrate tissue may comprise bone and the step of positioning the first anchor may comprise drilling a hole in the bone followed by positioning of the first anchor therein. The step of positioning the first anchor may comprise advancing the first anchor from an elongate shaft of a delivery instrument. The method may further comprise at least partially encircling the damaged tissue with the suture, and the step of adjusting the length may comprise pulling the suture through a cinching mechanism disposed in either the first anchor or the tissue piercing needle. The cinching mechanism may be adapted to allow the suture to move in a first direction, while the suture is constrained from moving in a second direction opposite the first direction. The damaged tissue may comprise a torn labrum. The coupling step may comprise positioning the tissue piercing needle in a central channel of the first anchor.

These and other embodiments are described in further detail in the following description related to the appended drawing figures.

BRIEF DESCRIPTION OF THE DRAWINGS

FIGS. 25A-25B illustrate another exemplary embodiment of a cinching mechanism.
FIGS. 26A-26C illustrate yet another exemplary embodiment of a cinching mechanism.
FIGS. 37A-37B illustrate an exemplary embodiment of a cinching mechanism.
FIGS. 51A-51C illustrate another exemplary embodiment of a cinching mechanism.

FIGS. 64A-64H illustrate an exemplary method of suture anchor delivery.

FIGS. 65A-65H illustrate an exemplary method of suture anchor delivery.

DETAILED DESCRIPTION OF THE INVENTION

Several exemplary embodiments of knotless suture anchors, methods of use and delivery instruments are illustrated and described in the attached figures.

Figure 1:
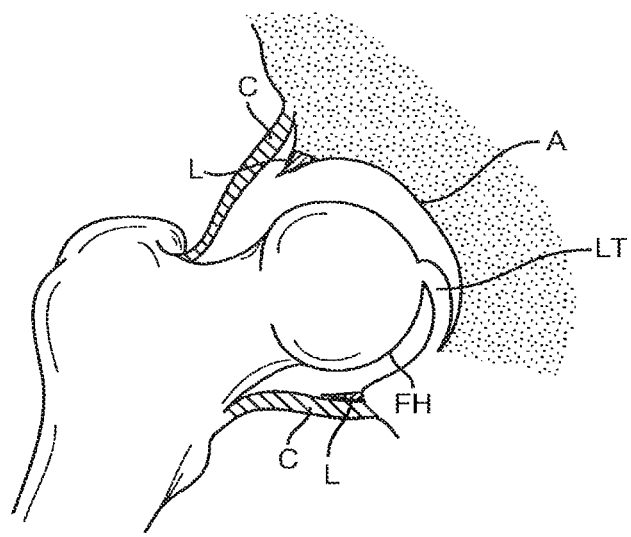
FIG. 1 illustrates basic anatomy of the hip.
Figure 2:
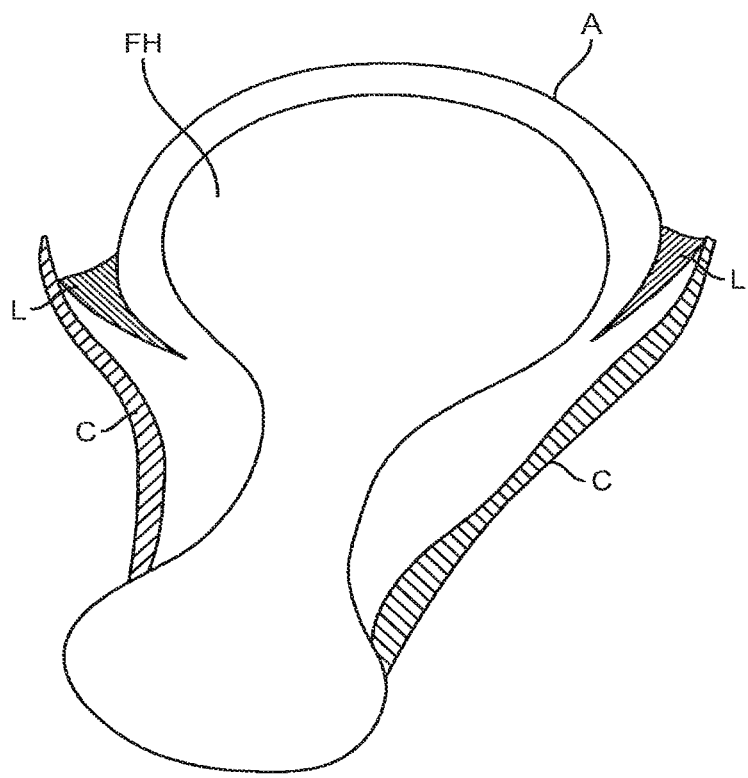
FIG. 2 illustrates a top view of the hip.

Anatomy:

Exemplary use of the devices, systems and methods of the present invention will be discussed primarily in terms of treatment of a hip joint. However, one of skill in the art will appreciate that other tissues may be re-attached to a base tissue or another substrate in other areas of the body including joints such as the shoulder joint, the ankle, wrist and other joints. Other areas may also be treated with the devices, systems and methods disclosed herein. Thus, the exemplary usage described herein is not intended to be limiting. FIG. 1 illustrates the basic anatomy of a hip joint. In FIG. 1 the hip joint is formed between the head of the femur FH and the acetabulum A, a concave surface of the pelvis. A blanket of ligaments cover the joint forming a capsule C. Additionally the acetabular labrum L, a fibrocartilaginous lip, surrounds the head of the femur, deepens the joint pocket and increases the surface area of contact. The ligamentum teres LT is a ligament attached to a depression in the acetabulum (the acetabular notch or fossa) and a depression on the femoral head (the fovea of the head). FIG. 2 is a top view of a hip joint highlighting the labrum L.

Figure 3:
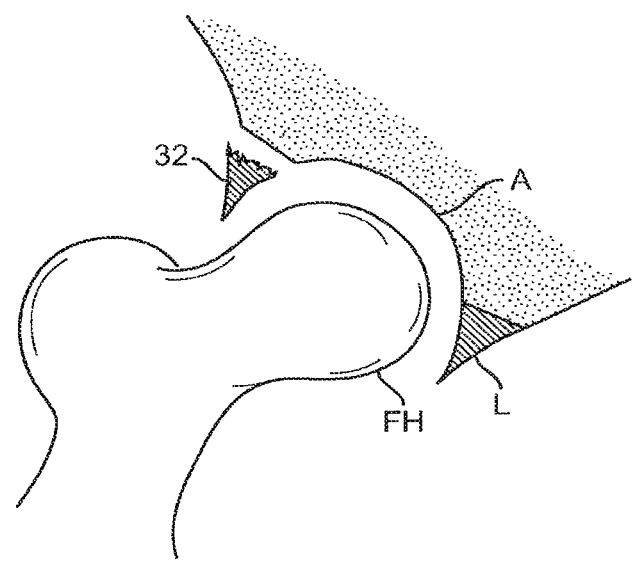
FIGS. 3-4 illustrate an exemplary method of reattaching a torn labrum to the acetabular rim.
Figure 4:
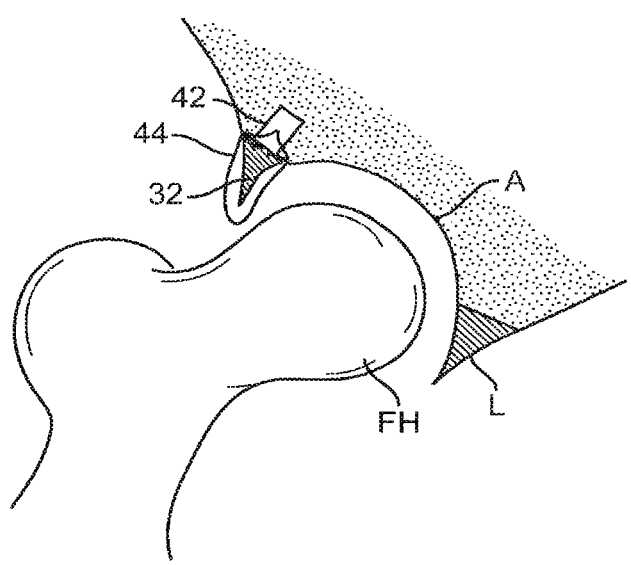

The labrum L can tear or separate from the acetabular rim due to wear or disease and this can result in pain as well as loss of joint mobility. FIG. 3 illustrates a torn labrum 32. Surgeons typically use suture and suture anchors to reattach the labrum to the acetabular rim. The surgeon often wraps a free end of the suture around the torn labrum and then the free end is threaded through a suture anchor. The anchor is inserted into bone and the suture length and/or tension is adjusted. FIG. 4 illustrates a torn labrum after it has been reattached to the substrate acetabulum. A suture anchor 42 with a suture 44 coupled thereto has been inserted into the acetabulum A thereby fixing one end of the suture 44 to the bone. The suture 44 is looped around the torn labrum 32 in order to capture the damaged tissue. The other end of the suture is also attached to the anchor and suture length has been adjusted in order to draw the labrum toward the acetabulum, where it is held until it heals and reattaches. Suture anchors are typically used instead of screws, pins, rivets or other fasteners due to the limited working space within the joint.

Figure 5A:
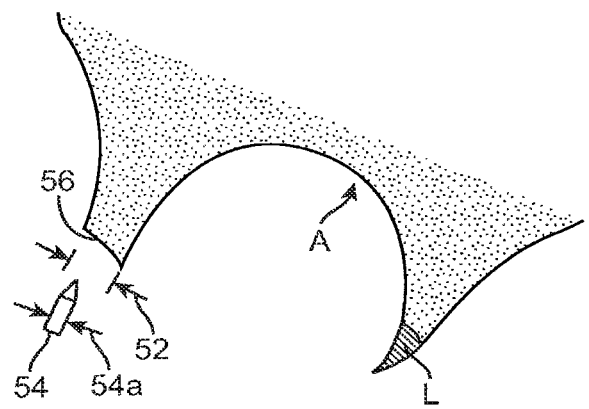
FIGS. 5A-5C illustrate dimensional constraints of a suture anchor used in the hip joint.
Figure 5B:
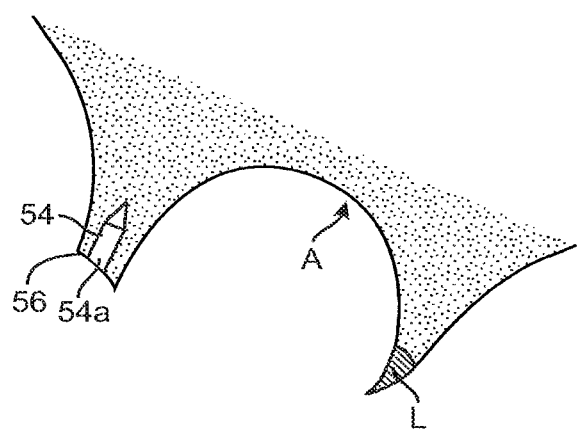
Figure 5C:
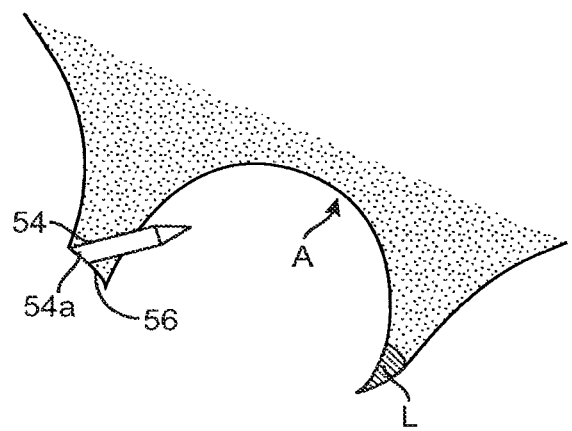

Referring now to FIGS. 5A-5C, the size of the suture anchor can be very important depending on the treatment zone. For example, when placing a suture anchor 54 into the acetabular rim 56 to repair the labrum L, the anchor width or diameter 54a cannot exceed the width 52 of the acetabular rim 56. Moreover, as shown in FIGS. 5A-5B, the anchor width 54a must be small enough relative to the width of the acetabular rim 56 so that adequate purchase is obtained without compromising strength of the rim 56. Thus, in most anchor embodiments described below, the suture anchor width (transverse to the anchor's longitudinal axis), or outer diameter if the anchor has a round profile, is preferably less than about 4 mm and no more than about 3.5 mm. Additionally, length of the anchor can also be critical. In FIG. 5B, the anchor 54 is placed substantially orthogonally into the acetabular rim and thus the anchor may be as long as necessary to obtain adequate purchase in the bone without risk of extending into the joint socket. However, it may be difficult to insert the anchor orthogonally into the acetabular rim due to the angle of approach, the narrow width of the rim, or for other reasons. In such cases, the anchor may be placed at a non-perpendicular angle relative to the rim surface, or it may be placed into a lateral facet of the acetabulum. In such cases, if the anchor is either too long or the angle is too great as shown in FIG. 5C, the anchor may pass entirely through the bone and exit into the joint itself, here the acetabular socket A, potentially damaging the cartilage and interfering with joint motion. Thus, when repairing a torn labrum in an acetabular or glenoid rim, the anchor has a diameter usually less than 5 mm, preferably less than 4 mm, and more preferably 3.5 mm or less. The length must be long enough to gain adequate purchase in the bone while also being short enough to avoid penetration into the articular surface, preferably being at least about 5 mm and less than or equal to about 14 mm in length.

Figure 6A:
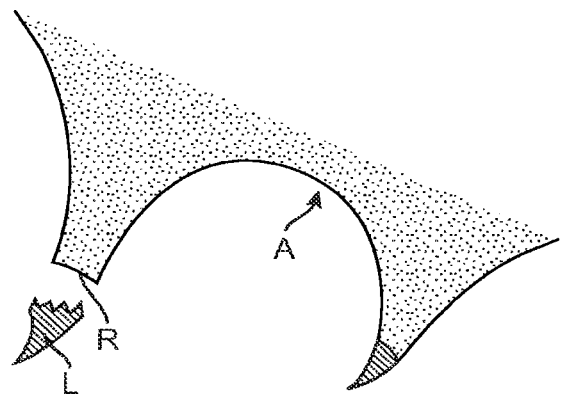
FIGS. 6A-6D illustrate an exemplary method of placing suture anchors into a hip joint.
Figure 6B:
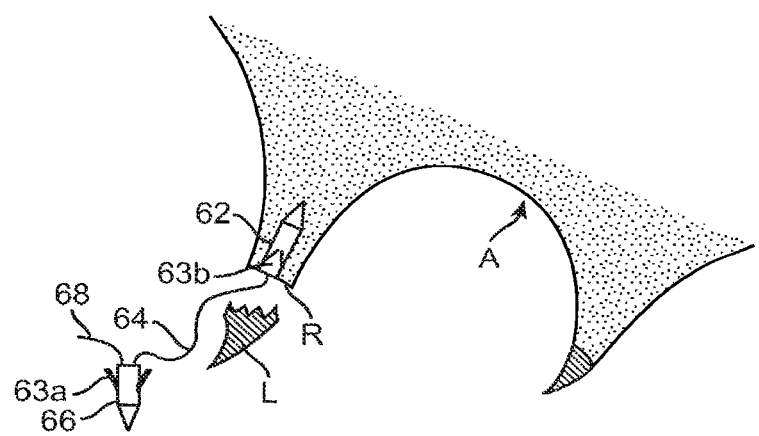
Figure 6C:
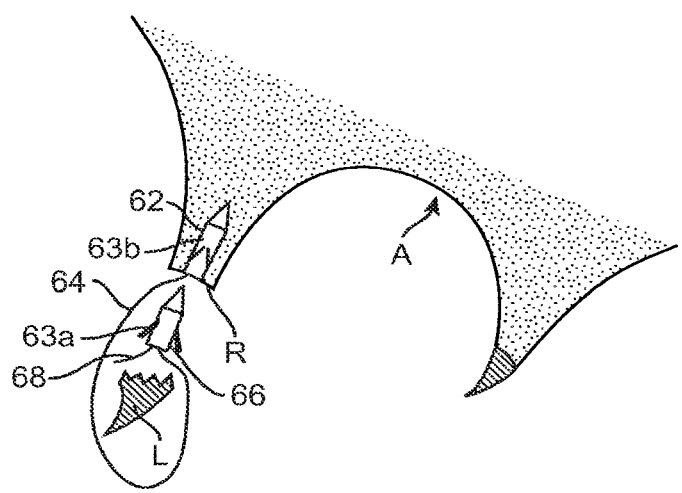
Figure 6D:
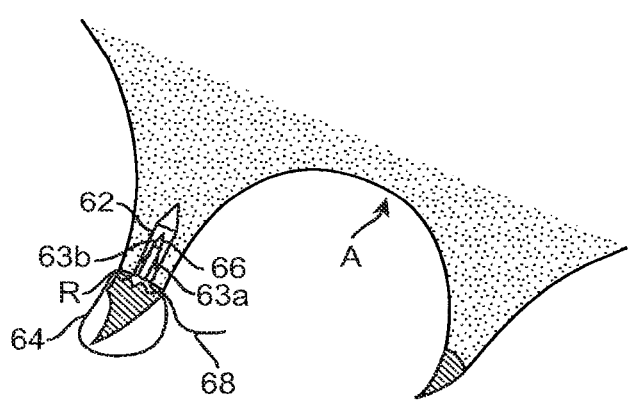

FIGS. 6A-6D illustrate an exemplary system and method for reattaching a torn labrum to the acetabular rim. The suture anchor system includes an outer anchor 62 and an inner anchor 14 66. A length of suture 64 having a free end 68 is coupled to both of the anchors 62, 66. Preferably suture 64 is pre-threaded in both anchors 62, 66 such that no threading of the suture through the anchors is required during the procedure, before or after placement of either anchor. The pair of anchors 62, 66 include a coupling mechanism 63a, 63b that allow the two anchors to interlock with one another when the inner anchor 66 is inserted into the outer anchor 62. In this embodiment, the inner anchor 66 is inserted concentrically into an inner cavity in the outer anchor 62, while in other embodiments described below, the anchors may be coupled together axially in a stacked relationship. In FIG. 6A, the torn labrum L is shown separated from the acetabular rim R of a hip joint having an acetabulum A. The outer anchor 62 is inserted into the acetabular rim R in FIG. 6B, either by placing the anchor into a pre-drilled hole or by directly driving the anchor into the bone. The suture 64 is then looped around the torn labrum L as shown in FIG. 6C and then the inner anchor 66 is inserted into the outer anchor 62 where the coupling mechanism 63a, 63b lock the two anchors together as shown in FIG. 6D. The suture 68 may then be tightened by pulling the free end which advances the suture through a cinching mechanism (not illustrated) in either the inner or outer anchor to tension the suture and draw the torn labrum into apposition with the acetabular rim R. The cinching mechanism allows the suture to be tensioned when pulled in one direction and constrains movement of the suture in the opposite direction. Once the appropriate tension has been achieved, the free end of the suture and any excess suture may be severed and removed from the treatment site. Additional details related to this method, the suture anchors and cinching mechanism may be found in U.S. patent application Ser. No. 12/605,065 and U.S. patent application Ser. No. 12/776,177, the entire contents of which are incorporated herein by reference.

Suture Anchor Configurations:

Any of the suture anchors described herein may be fabricated from metals such as stainless steel, nitinol, titanium, etc., ceramics, and other biocompatible materials. However, in preferred embodiments, the anchors are made from MRI (magnetic resonance imaging) compatible polymers such as PEEK (polyetherether ketone) or carbon reinforced PEEK. Dense, hard polymers are preferred so that the anchors will be non-resilient and do not deform when implanted. Preferred embodiments of anchors displace the bone or other substrate tissue when implanted.

Figure 7:
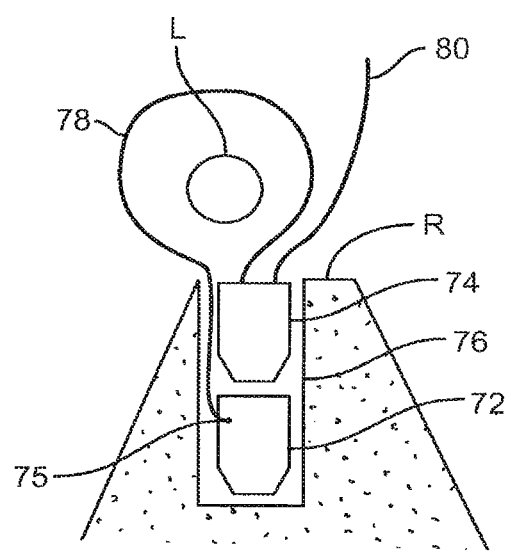
FIG. 7 illustrates suture anchors positioned end-to-end.

In other embodiments of suture systems, the anchor may include more than one suture anchor positioned in a single hole. For example, an approach for the deployment of suture anchors in an axially stacked arrangement in the same hole is illustrated in FIG. 7. A pair of suture anchors 72, 74 and a length of suture 78 having a free end 80 are used to reattach a torn labrum L to the acetabular rim R. In this exemplary embodiment, both anchors 72, 74 are placed end-to-end in a single pre-drilled hole 76 or they may be directly driven into the acetabular rim R. Suture 78 is coupled to the distal-most anchor 72 with a knot 75 or using another fastening method (e.g. crimping, bonding, etc.) and the length of suture encircles the labrum L and passes through the proximal-most anchor 74. The proximal-most anchor includes a cinching mechanism (not shown) that allows the free end 80 of the suture 78 to be pulled and tensioned in one direction while constraining movement of the suture in the opposite direction. By placing the two anchors end-to-end, both anchors may have maximum diameter within the constraints of the target anatomical location which allows the cinching mechanism size to also be maximized. Moreover, this configuration also minimizes the number of holes that must be drilled into the bone during the procedure. Another advantage of this configuration is that a portion of the suture 78 is pinched between an outer surface of the proximal-most anchor 74 and the inner wall of the hole 76. Not only does this secure the suture in position, but allows a gross adjustment of the suture length or tension by pulling the end of the suture 78 to draw the repaired tissue toward the bone, followed by a fine adjustment of suture length and tension by pulling the opposite end of the suture through the cinching mechanism. Additional details on cinching mechanisms which may be used in these anchors are described below, as well as in Provisional and Non-Provisional patent applications previously incorporated herein by reference. The suture anchors may also be placed in separate holes in the bone if desired.

Figure 8:
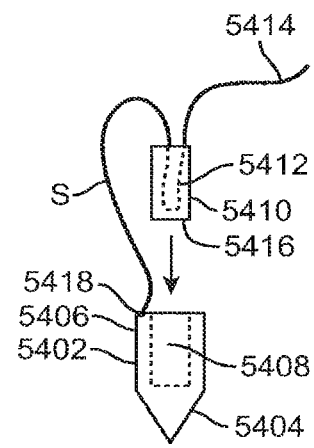
FIGS. 8-16 illustrate exemplary suture anchor configurations.

Other exemplary configurations are shown in FIGS. 8-16. For example, FIG. 8 schematically illustrates a two-part suture anchor system having an anchor 5402 and an insert 5410 coupled together with a suture S. The anchor 5402 generally has a cylindrical shaped body 5406 and a pointed tip 5404 that is adapted to penetrate into bone. A central channel 5408 is substantially parallel to the longitudinal axis of the cylindrical body 5406. The insert 5410 also is generally cylindrically shaped and is concentrically positionable in the central channel 5408 such that the distal end 5416 of the insert 5410 bottoms out in the central channel 5408. The insert 5410 may be sized such that it is press fit into the central channel 5408 or it may have a locking mechanism, such as a detent mechanism, snap fit, threads, or other mechanical locking mechanism to lock the insert 5410 with the anchor 5402. The insert 5410 also has a cinching mechanism 5412 that allows the suture to be pulled in one direction for adjustment and tightening, while constraining movement of the suture in the opposite direction. The cinching mechanism may be any of the cinching mechanisms disclosed herein. The suture S has one end attached to the anchor with a knot 5418 or by other techniques known to those skilled in the art and the suture also passes through the cinching mechanism 5412 and a free end 5414 extends from the insert. The free end 5414 may be pulled to tighten the suture.

Figure 9:
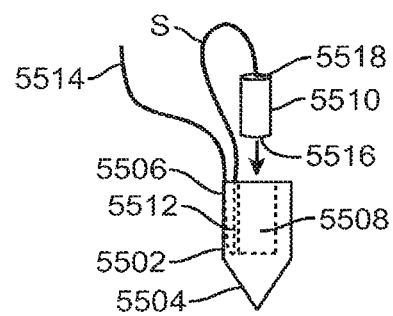

FIG. 9 schematically illustrates another anchor system configuration similar to that of FIG. 8, with the major difference being that the cinching mechanism is a part of the anchor instead of the insert. In FIG. 9, the anchor 5502 generally has a cylindrical shaped body 5506 and a pointed tip 5504 that can penetrate into bone. The anchor 5502 also has a central channel 5508 and a cinching mechanism 5512. The cinching mechanism may take the form of any of the cinching mechanisms described herein. The insert 5510 is also generally cylindrically shaped and is positionable in the central channel 5508 where it may be locked in place using any of the features described herein. The distal end 5516 of the insert 5510 in this embodiment has a flat planar face, although in other embodiments it may be pointed as will be seen below. A suture S is coupled to both the anchor 5502 and the insert 5510. One end of the suture S is tied in a knot 5518 or otherwise secured to the insert 5510 and the suture passes through the cinching mechanism 5512 of the anchor 5502. A free end 5514 extends from the anchor 5502 and may be pulled in one direction to tighten the suture.

Figure 10:
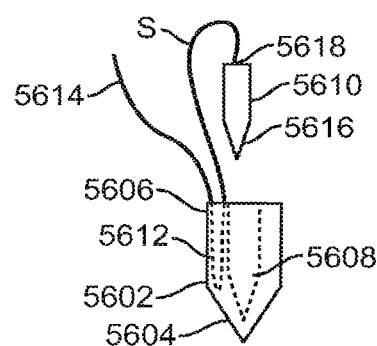

FIG. 10 schematically illustrates still another anchor system having an anchor 5602, a suture S, and a needle insert 5610. The anchor 5602 has a generally cylindrical shaped body 5606 with a central channel 5608 and a pointed tip 5604 adapted to penetrate into bone. A cinching mechanism 5612 that generally takes the form of any of the cinching mechanisms disclosed herein is included in the anchor 5602. The needle insert 5610 also has a cylindrically shaped body and a distal tissue penetrating tip 5616 for passing through tissue. A suture S is coupled to both the needle insert 5610 and the anchor 5602. One end of the suture S is fixed to the needle insert 5610 with a knot 5618 or other technique and the suture S passes through the cinching mechanism 5612. A free end 5614 extends from the cinching mechanism 5602 and may be pulled through the cinching mechanism in one direction to tighten the suture S. The cinching mechanism constrains movement of the suture therethrough in the opposite direction.

Figure 11:
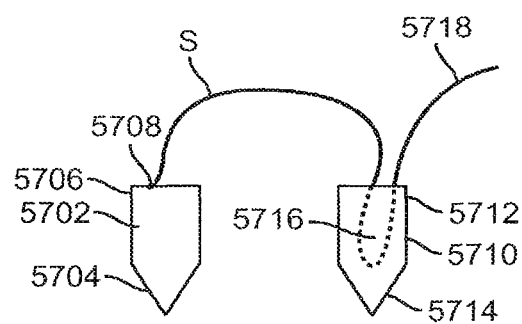

FIG. 11 schematically illustrates yet another anchor system having two anchors 5702, 5710. The first anchor 5702 has a generally cylindrical shaped body 5706 and a pointed tip 5704 for penetrating into bone. The second anchor 5710 similarly has a cylindrically shaped body 5712 and a pointed tip 5714 for penetrating into bone. The second anchor may be positioned in the same or a different location than the first anchor. The second anchor 5710 also includes a cinching mechanism 5716 that allows the suture S to be advanced in one direction and constrained in the opposite direction. A suture S is coupled to both anchors 5702, 5710. One end of the suture S is fixed to the first anchor 5702 with a knot 5708 or with other techniques known to those skilled in art, and the suture S passes through the cinching mechanism 5716 in the second anchor 5710. A free end 5718 of the suture S extends from the cinching mechanism and may be pulled to adjust suture length extending between the anchors 5702, 5710.

Figure 12:
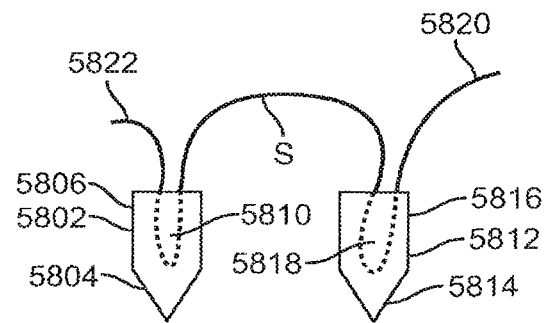

FIG. 12 illustrates another anchor system having two anchors 5802, 5812. In this embodiment, both anchors 5802, 5812 include cinching mechanisms 5810, 5818. The first anchor 5802 has a generally cylindrically shaped body 5806, a pointed distal tip 5804 for penetrating tissue such as bone and a cinching mechanism 5810. The second anchor 5812 similarly has a cylindrically shaped body 5816, a pointed tip 5814 for penetrating bone or other tissue, and a cinching mechanism 5818. The second anchor may be positioned in the same location or a different location than the first anchor. A length of suture S is coupled to both anchors 5802, 5812. The suture passes through both cinching mechanisms 5810, 5818, and has a first free end 5822 that extends from the first anchor 5802, and a second free end 5820 that extends from the second anchor 5812. Thus, in this exemplary embodiment, either or both free ends 5820, 5822 may be pulled in order to adjust the length of the suture extending between the anchors.

Figure 13:
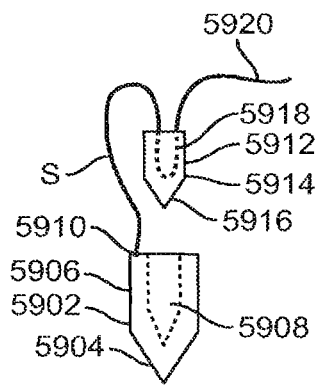

FIG. 13 schematically illustrates another anchor system having two anchors 5902, 5912. The first anchor 5902 includes a generally cylindrically shaped housing 5906, a pointed distal tip 5904 for penetrating into bone and a central channel 5908. The second anchor 5912 also includes a generally cylindrically shaped body 5914, a pointed distal tip 5916 for penetrating bone, and a cinching mechanism 5918. The second anchor 5912 may be positioned directly into bone or it may be positioned concentrically in the central channel 5908 of the first anchor 5902 and locked in place using any of the locking mechanisms described herein or known in the art. A length of suture S is coupled to both anchors 5902, 5912. One end of the suture S is fixed to the first anchor 5902 with a knot 5910 or by other methods known in the art. The suture S passes through the cinching mechanism 5918 in the second anchor 5912 and a free end 5920 extends from the second anchor 5912 and may be pulled in one direction to adjust the suture length between the two anchors. The cinching mechanism prevents the suture from moving in the opposite direction.

Figure 14:
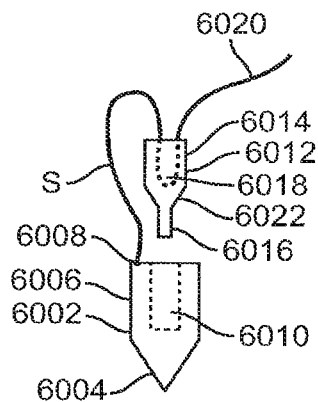

FIG. 14 schematically illustrates another anchor system having two stacked anchors 6002, 6012. The first anchor 6002 has a generally cylindrically shaped body 6006, a pointed tip 6004 for penetrating bone and a central channel 6010 that is generally parallel with the longitudinal axis of the first anchor 6002. The second anchor 6012 also includes a generally cylindrically shaped body 6014 and a cinching mechanism 6018. The cylindrical body 6014 has a tapered shoulder 6022 near the distal end of the anchor 6012 and a reduced diameter distal region 6016 that is positionable and lockable in the central channel 6010 of anchor 6002. A suture S is coupled to both anchors 6002, 6012. One end of the suture S is fixed to the first anchor 6002 with a knot 6008 or by other techniques. The suture passes through the cinching mechanism 6018 and a free end 6020 extends therefrom.

Figure 15:
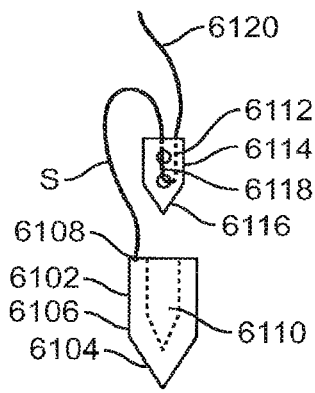

FIG. 15 schematically illustrates another anchor system having an anchor 6102 and a needle insert 6112. The anchor 6102 generally takes the same form as other anchors disclosed herein and includes a cylindrically shaped body 6106, a pointed distal tip 6104 for penetrating tissue such as bone, and a central channel 6110 that is substantially parallel to the longitudinal axis of the anchor 6102. The needle insert 6112 includes a cylindrically shaped body 6114, a cinching mechanism 6118, and a pointed distal tip 6116 that can penetrate tissue or bone. The needle insert 6112 is positionable and lockable in the central channel of the anchor 6102. A suture S is coupled to both the anchor 6102 and the needle insert 6112. One end of the suture S is attached to the anchor 6102 with a knot 6108 or by other attachment means known in the art. The suture also passes through the cinching mechanism 6118 and a free end 6120 of the suture S extends from the needle insert 6112 and may be pulled through the cinching mechanism to tighten the suture, while movement of the suture in the opposite direction is constrained. In this exemplary embodiment, the cinching mechanism may take the form of any of the embodiment disclosed herein.

Figure 16:
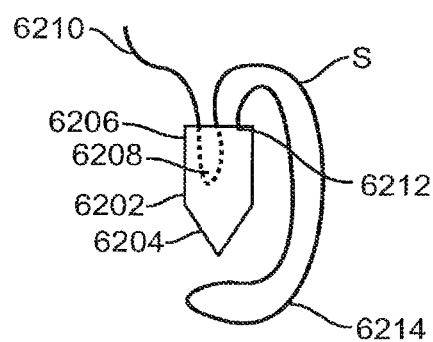

FIG. 16 schematically illustrates still another anchor system, this time with a single anchor 6202. The anchor 6202 includes a generally cylindrically shaped body 6206, a cinching mechanism 6208, and a pointed distal tip 6204 for penetrating tissue such as bone. One end of a suture S is fixed to the anchor 6202 with a knot 6212 or by other means and forms a loop region 6214 before passing through the cinching mechanism 6208. A free end 6210 of the suture S extends from the anchor 6202 and may be pulled to adjust the suture. In use, the suture at least partially encircles tissue to be captured and then the anchor 6202 passes through the loop 6214 and is then anchored into bone or other tissue. The suture can then be adjusted by pulling the free end 6210.

Figure 17A:
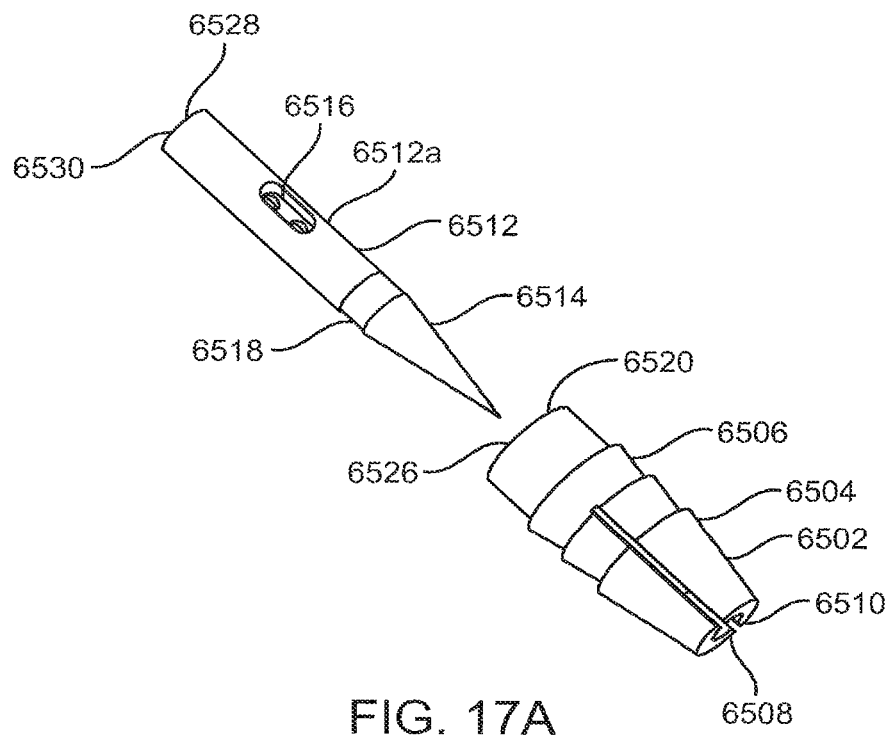
FIGS. 17A-17D illustrate an exemplary suture anchor.
Figure 17B:
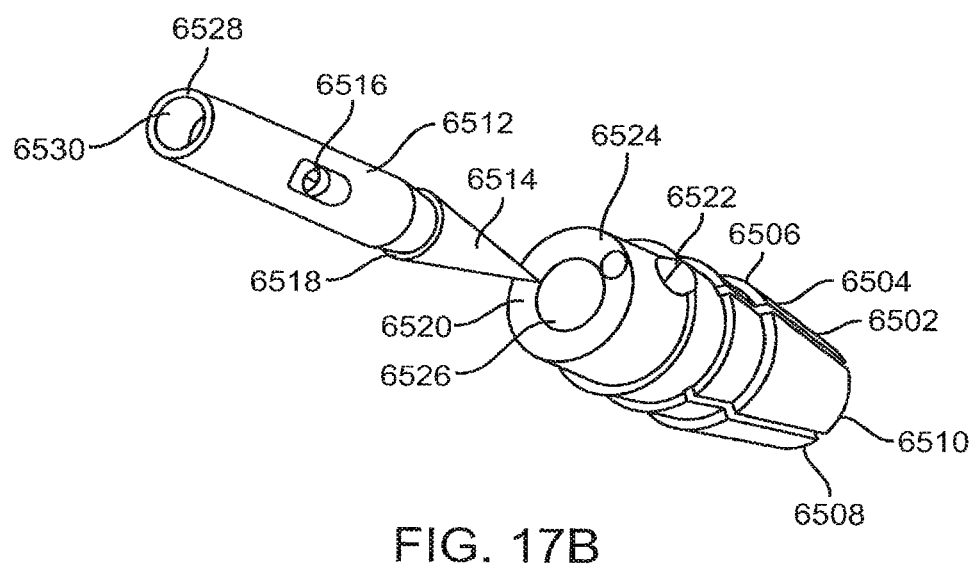
Figure 17C:
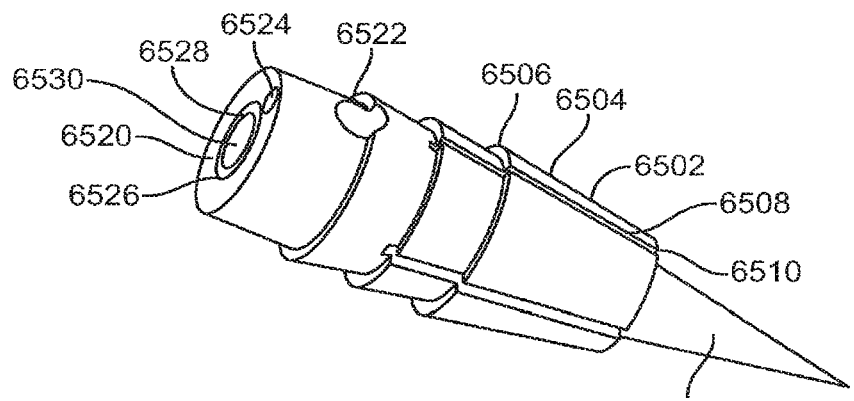
Figure 17D:
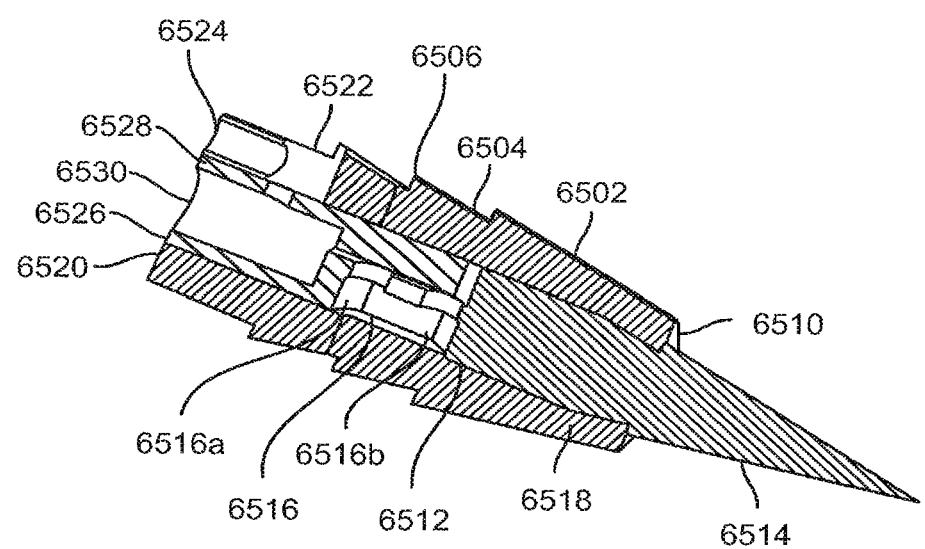

FIGS. 17A-17D illustrate another embodiment of a suture anchor system having an anchor and a needle. FIGS. 17A-17B are perspective views of the system rotated into different positions. FIG. 17C is a perspective view of the system when the anchor is coupled to the needle and FIG. 17D is a cross-sectional view of FIG. 17C taken along its longitudinal axis. The anchor system includes an anchor 6502 having a cylindrical shaped body 6504 and a plurality of barbs or scallops 6506 along the outer surface of the body 6504 to help the anchor remain positioned in tissue such as bone. The distal portion 6510 of the anchor has a flat end and a plurality of longitudinal slits 6508 that allow the distal portion 6510 to expand and contract as the needle is inserted into the anchor. The proximal end 6520 of the anchor 6502 is also flat and has a central channel 6526 extending all the way through the anchor 6502. The channel 6526 is substantially parallel to the longitudinal axis of the anchor. A channel 6524 extends through a side wall of the anchor substantially parallel to the longitudinal axis of the anchor and intersects with a passage 6522 that extends transversely through the anchor side wall (best seen in FIG. 17B). A suture may be fed through these passages and tied to the anchor.

The needle 6512 includes a pointed tip 6514 that is adapted to pierce tissue and also has a shoulder 6518 that helps the needle snap into engagement with the anchor when the needle is concentrically positioned in the anchor. The needle 6512 also includes a cylindrical body 6512a and the proximal end 6528 of the needle 6512 is flat and has a central channel 6530 extending into the needle. A central region of the needle includes a cinching mechanism 6516 which includes two apertures 6516a, 6516b (best seen in FIG. 17D) for receiving suture (not illustrated). This embodiment of cinching mechanism generally operates in the same manner as described with respect to FIGS. 21A-21B described below. One of skill in the art will of course appreciate that any of the cinching mechanisms disclosed herein may also be used.

In use, the anchor 6502 is positioned in bone and the needle is used to pierce through and pass a suture through damaged tissue. The needle is then coupled with the anchor and the suture is tensioned by pulling it through the cinching mechanism. This will be more thoroughly described below.

Figure 18:
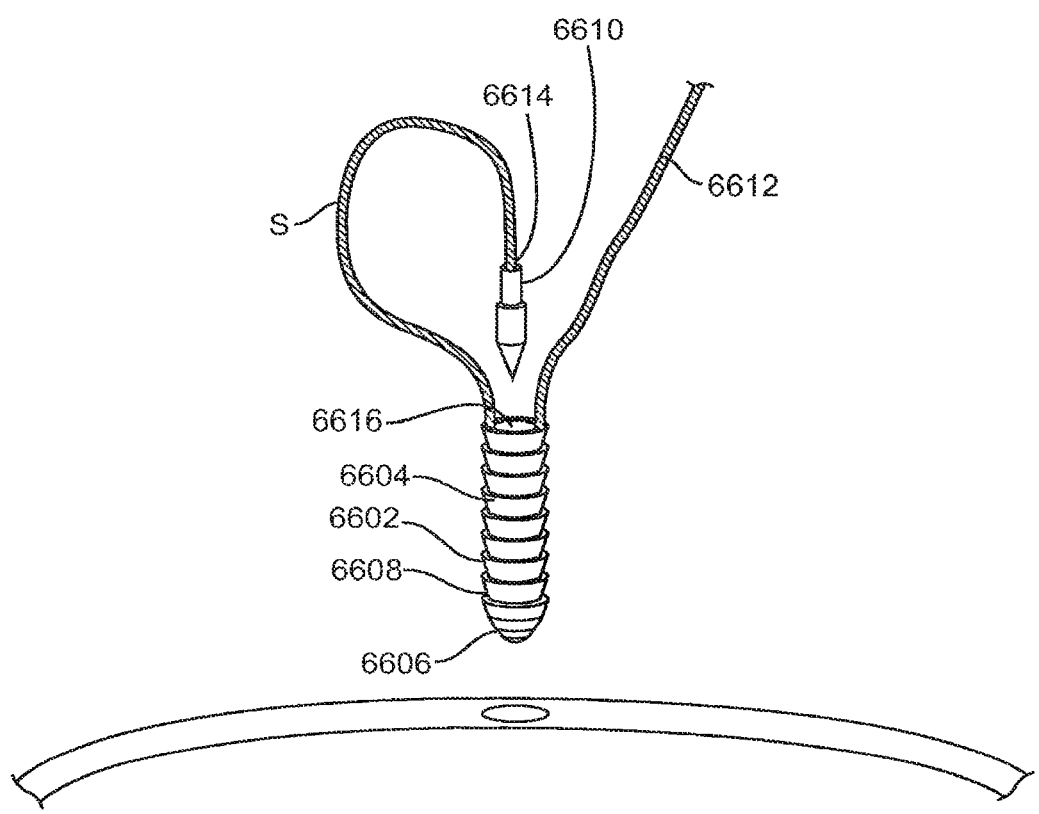
FIG. 18 illustrates another exemplary suture anchor.

In some embodiments, a portion of the anchoring system includes a piercing needle for capturing the damaged tissue by passing the suture therethrough. FIG. 18 illustrates another embodiment of an anchor system and needle. The anchor 6602 has a generally cylindrical shaped body 6604 with barbs 6608 along the outer surface and a tissue piercing tip 6606. The anchor 6602 includes any of the cinching mechanisms described herein and has a central passage 6616 for receiving the tissue piercing needle 6610. A length of suture S having a free end 6612 is fixed to the needle 6614 by crimping, bonding, knotting or by other methods. The suture 10 passes into the cinching mechanism (not illustrated) in the anchor 6602 and the free end 6612 exits the anchor. In use, the anchor 6602 is positioned in bone and the suture S at least partially captures the tissue to be repaired. The needle 6610 is then pierced through the tissue and the suture is also passed through the tissue. The needle is then inserted concentrically into the central channel 6616 of the anchor 6602 and locked into position. The suture S is then adjusted by pulling on the free end 6612 of the suture. In preferred embodiments, the needle diameter ranges from about 1.0 mm to about 2.2 mm. Needle length may range from about 2 mm to about 13 mm. The needle may have a straight tip or the tip may be curved or angled. An angled needle may range from 20 to 60 degrees. Using a needle to pass through the tissue may help retain the natural shape of the tissue thereby helping it to reattach and heal more quickly than if the tissue were deformed by tightening the suture around the tissue.

In anchoring systems having two or more suture anchors, it may be advantageous to attach the two anchors directly together. This minimizes the possibility that the anchors will become dislodged. For example, in FIG. 19, two anchors are stacked together in the same hole and joined with one another. A pair of anchors 82, 84 are coupled together with a suture 86 having a free end 86*a*. A coupling element 83 extends from the proximal end of the distal anchor 82 and allows the two anchors to be joined together. One end of the suture 86 is fixed to one anchor 82 with a knot 88 or other fastening methods may be used, and this anchor 82 may be placed into the bone before the other anchor 84. Once the anchor 82 is positioned into a pre-drilled hole in the bone or driven directly into the bone, the target tissue is captured by wrapping the second anchor around it or placing the second anchor through a penetration through the target tissue. Second anchor 84 is preferably placed into the same hole as first anchor 82, but may be configured for placement in a separate hole if desired. The second anchor 84 is advanced in the hole until its distal end butts up against the proximal end of the first anchor 82 and the coupling element 83 joins the two anchors together. The coupling element 83 may be a threaded rod that allows the two anchors to be screwed together, or the coupling element 83 may be a compression coupling with ribs or other features to enhance friction that is press fit into a corresponding bore (not shown) in the second anchor 84. Coupling element 83 has a relief feature 83*a* which allows two opposing halves of the relief feature to flex radially inward toward each other to facilitate insertion in the bore in the distal end of proximal anchor 84. One of skill in the art will appreciate that other coupling mechanisms, such as a ratchet, detent, snap fit or other mechanisms may be used to join the two anchors together. Once the two anchors are coupled together, the free end 86*a* of the suture may be pulled to advance the suture 86 through a cinching mechanism (not shown) in the second anchor 84 thereby allowing adjustment of suture length and tension. The second anchor 84 may have any of the cinching mechanisms disclosed in this specification.

Figure 20:
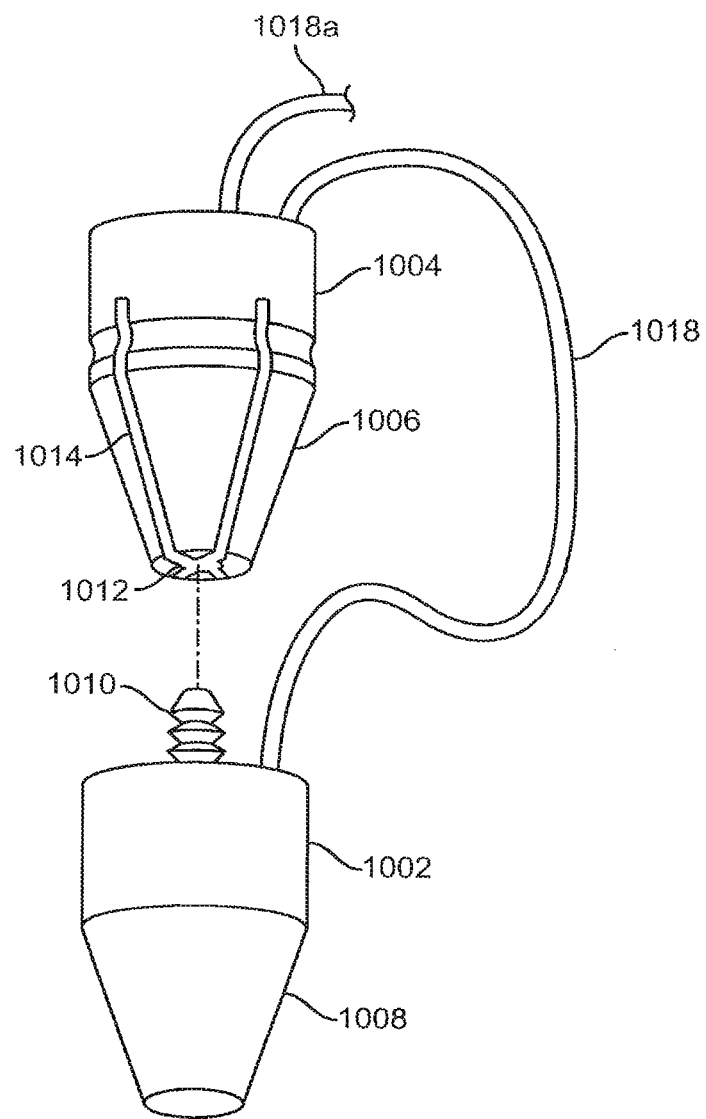

FIG. 20 illustrates another exemplary embodiment of a pair of anchors that couple together in an end-to-end configuration. The anchors 1002, 1004 are coupled together with a length of suture 1018 having a free end 1018*a*. Each anchor 1002, 1004 has a tapered distal end 1006, 1008 that helps align the anchor into a hole drilled into the bone or provides a penetrating tip that may be driven directly into bone. A coupling element 1010 is attached to anchor 1002 and may be a threaded rod or a compression coupling that engages with the corresponding engagement feature (e.g. a threaded female receptacle or a channel) 1012 on anchor 1004. Additionally, anchor 1004 includes a series of relief slots 1014 that allow the distal extremity of the anchor to radially expand and contract as the coupling element 1010 is advanced into engagement with anchor 1004. Thus, as the coupling element is initially advanced into aperture 1012, the relief slots allow the anchor 1004 to expand and receive the coupling element 1010. Once the coupling element has been inserted into anchor 1004, the anchor collapses back to its natural shape, locking the coupling element 1010 in place and providing an end-to-end or stacked pair of suture anchors. While this embodiment illustrates the male coupling element 1010 on anchor 1004, one will of course appreciate that it could easily be placed on anchor 1004. In use, once the anchors have been placed into the bone, the free end of the suture 1018*a* may be pulled, pulling the suture 1018 through a cinching mechanism (not shown) in anchor 1004. The cinching mechanism may be any of the mechanisms disclosed in this specification or incorporated by reference.

Figure 21A:
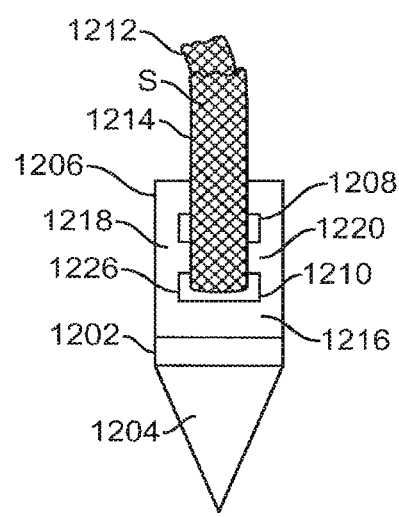
FIGS. 21A-21B illustrate an exemplary embodiment of a cinching mechanism.
Figure 21B:
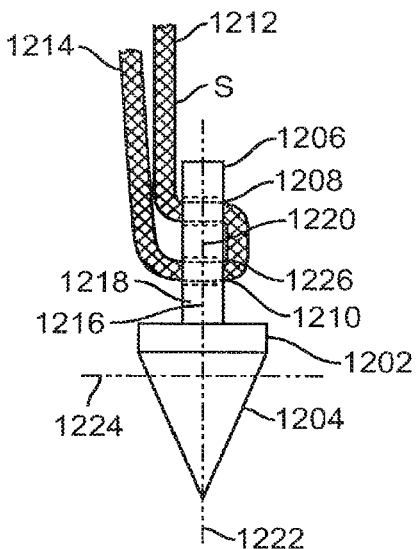

One-Way Cinching Mechanisms:

FIGS. 21A-21B illustrate a first exemplary embodiment of a suture cinching mechanism that may be used in any of the suture anchors disclosed herein. The suture anchor 1202 may have a tapered cylindrical tip 1204 to facilitate positioning in a hole in bone or to provide a tip that may be advanced to penetrate directly into the bone. A central wall 1216 extends proximally from tip 1204 such that its face 1218 is generally parallel to the longitudinal axis 1222 of anchor 1202. Wall 1216 has an upper aperture 1208 and a lower aperture 1210 extending transversely (indicated by phantom line 1224) through wall 1216 and separated by a bar 1220, thus forming a buckle 1206. A first extremity 1214 of suture S enters the lower aperture 1210 from one side of the buckle, passes through the lower aperture 1210 and exits the aperture. The suture S then enters the upper aperture 1208 from the opposite side of the buckle and exits the aperture such that a second extremity 1212 of the suture S is positioned under the first extremity 1214 of the suture, thus forming a loop around bar 1220. It will be appreciated that the terms "enter" and "exit" are relative and therefore a suture that enters an aperture may also be referred to as exiting the aperture. Similarly, a suture that is described as exiting an aperture may be referred to as entering the aperture. This applies throughout this specification unless indicated to the contrary. When positioned in a hole in bone or other tissue, anchor 1202 is inserted far enough so that wall 1216 is fully recessed inside the hole. This constrains the first extremity 1214 and second extremity 1212 of suture S within a space lying between the wall 1216 and the surrounding bone or tissue, thereby maintaining them in an orientation in which the first and second extremities are generally parallel (+/−30 degrees) to the longitudinal axis 1222 of anchor 1202 and the face 1218 of wall 1216. This orientation of the first and second extremities of suture S help to ensure the proper functioning of the cinching mechanism. If the second extremity 1212 of suture S is pulled the suture will advance through the buckle. However, when the first extremity 1214 of the suture is pulled, it compresses second extremity 1212 against the underlying face 1218 of wall 1216, thereby preventing the suture from advancing through the buckle. Preferably, the lower aperture 1210 forms a corner 1226 where it intersects with the face of bar 1220, the corner having an angle of no more than about 90 degrees, thus creating an edge which engages suture S and inhibits its movement when first extremity 1214 is tensioned. Thus, the cinching mechanism allows the suture be adjusted in one direction and constrains motion in the opposite direction. In this embodiment, the suture is preferably a suture having a flat or rectangular cross-section in order to increase friction, but other cross-sections may also be used including round suture. The slots 1208, 1210 are sized and shaped accordingly, therefore in this embodiment, both slots are rectangular, but they could also be round. FIG. 21B is a side view of FIG. 21A. Preferably this suture anchor and others described herein are fabricated by injection molding a polymer such as polyetheretherketone (PEEK), carbon reinforced PEEK or other polymers including biodegradable polymers such as polylactic acid (PLA) or polyglycolic acid (PGA). Thus, a single integral construct is provided requiring no assembly and no moving parts. Alternatively, some embodiments of anchors disclosed below may be moldable as a single piece, but may be molded into several components which are then assembled together.

Although not illustrated, it will be understood that any of the embodiments of the suture anchors of the invention described herein may include features on the exterior thereof to enhance retention of the anchor in bone or other tissue. Such features may comprise bumps, ridges, ribs, threads, scales, flaring wings, projections, or other structures to enhance friction or to mechanically engage the surrounding bone or tissue and resist proximal movement of the anchor after it has been fully inserted. Such features are well-known in the art, with examples illustrated in U.S. Pat. Nos. 6,554,852, 6,986,781, and 6,007,566, which are incorporated herein by reference.

Figure 22A:
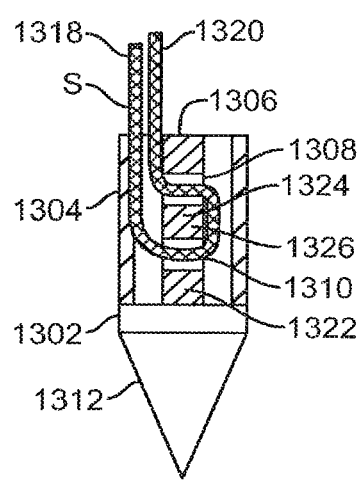
FIGS. 22A-22B illustrate another exemplary embodiment of a cinching mechanism.
Figure 22B:
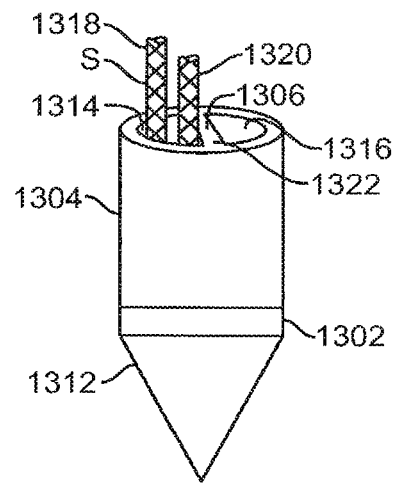

FIGS. 22A-22B illustrate another cinching mechanism embodiment. This is similar to the one previously described in FIGS. 21A-21B with the major difference being that the cinching mechanism is enveloped by a housing. FIG. 22A shows a cross-section of the anchor and cinching mechanism. The anchor 1302 has a tapered tip 1312 for alignment with a hole in bone or for providing a tip that can penetrate directly into bone. The anchor has a central wall 1322 arranged generally parallel to the longitudinal axis of the anchor with two transverse apertures 1308, 1310 therein separated by a transverse bar 1324, forming a buckle 1306 for cinching the suture S. The cinching mechanism is surrounded by a housing 1304 having two proximal openings 1314, 1316. The housing is preferably cylindrically shaped, but may have other configurations, including, but not limited to square, rectangular, oval, triangular, or other shapes. Any of the anchor housings disclosed herein may have any of these shapes. The housing guides the first extremity 1318 and second extremity 1320 from apertures 1314, 1316 in a direction generally parallel to wall 1322 in lieu of relying upon the wall of the hole for this purpose as in the previous embodiment. A first extremity 1318 of suture S enters the lower aperture 1310 from a first side and exits that aperture on a second side, opposite the first side. The suture then enters the upper aperture 1308 from the second side and exits the upper aperture on the first side. A second extremity 1320 of the suture S exiting the upper aperture 1308 is positioned under the first extremity 1318 of suture S. In this embodiment, the suture S enters and exits the housing through aperture 1314, although the suture could also enter and exit the other aperture 1316. Operation of the cinching mechanism is generally the same as previously described with respect to FIGS. 21A-21B. Pulling on the second extremity of suture 1320 allows the suture to pass through the buckle 1306. However, pulling on the first extremity of suture 1318 compresses the second extremity of suture 1320 against the wall 1322 creating friction between the suture and the buckle 1306, thereby preventing the suture from moving in that direction. Optionally, ridges, bumps, or other features may be provided on the face 1326 of wall 1322 to enhance friction against second extremity of suture 1320. This embodiment may be molded as a single integral construct or as two or more components that are assembled together. For example, the buckle and anchor tip may be molded as one component and the cylindrical housing may be molded as a second component. The two pieces may then be bonded, welded, fastened or snap fit together using techniques well known in the art.

Figure 23:
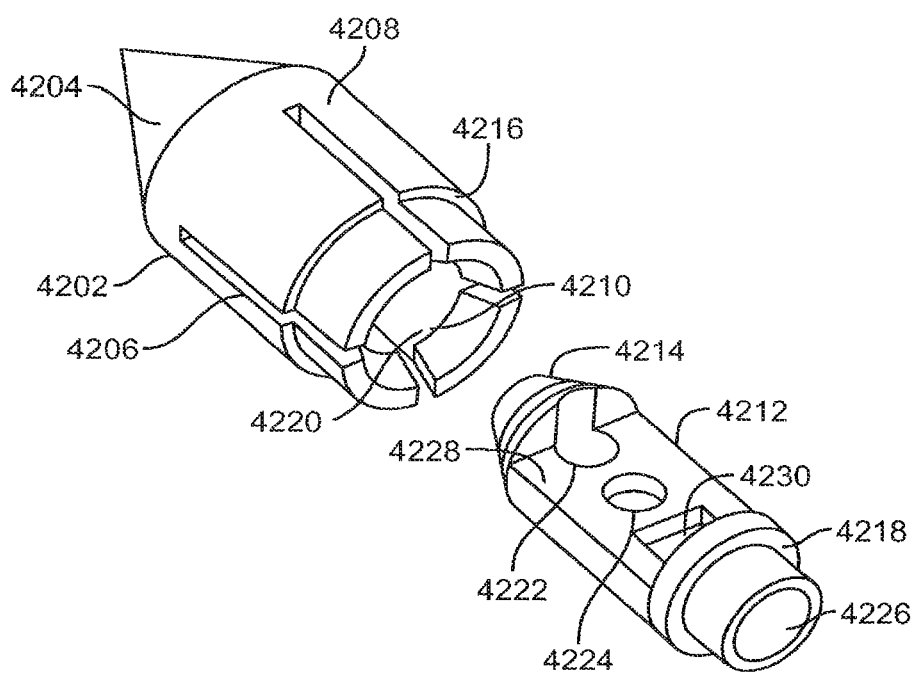
FIG. 23 illustrates another exemplary embodiment of a suture anchor.

FIG. 23 illustrates a perspective view of a suture anchor system having an outer anchor, an inner anchor positionable concentrically in the outer anchor, and a cinching mechanism in the inner anchor. The outer anchor 4202 includes a cylindrical shaped housing 4208 with a central channel 4210 and a pointed or tapered tip 4204 similar to those previously described. The housing includes a plurality of longitudinally oriented slots 4206 that form discrete sections at the proximal end of the housing which can flex outwardly. Additionally, the housing includes an outer annular flange 4216 and an inner annular flange 4220. The inner anchor 4212 has a distal pointed or tapered distal tip 4214 that may be used to help guide the inner anchor into the outer anchor or that may be driven directly into the bone or other tissue. The proximal end of the inner anchor has an annular flange 4218 and also a cylindrical end with a passage 4226 therethrough. A middle portion of the inner anchor between the distal tip and the proximal end includes a flat recessed section 4228 having passages 4222, 4224 therethrough and an opening 4230 which communicates with passage 4226. In an exemplary embodiment the distal end of inner anchor 4212 has a sharpened tip adapted to penetrate the damaged tissue that is to be reattached, such that the inner anchor functions as a needle to pass directly through such tissue without the need for a separate device to create a penetration. In use, a first end of a suture (not shown) may be fixed to the outer anchor 4202 and the suture may then be threaded through apertures 4222, 4224 to form the cinching mechanism as shown in the embodiments illustrated in FIG. 21A-21B or 22A-22B. Once the outer anchor is positioned into bone or other tissue, the suture may be looped around damaged tissue or passed through a penetration in the damaged tissue and then either be inserted into the outer anchor and locked in place or positioned into the bone or other tissue separate from the outer anchor. Outer flanges 4216, 4218 on the outer and inner anchors are used as a seat for engagement by a delivery instrument to facilitate insertion of the anchors into the bone. Additionally, when the inner anchor is inserted into the outer anchor, the slots 4206 allow the discrete sections of the housing to be deflected outwardly to receive the inner anchor then resiliently snap back inwardly to lock the inner anchor in place. Once the inner anchor has been advanced deep enough into the outer anchor, the flange 4218 on the inner anchor will engage the flange 4220 on the outer anchor and the two anchors will be locked together. The suture may then be adjusted by pulling it through the cinching mechanism as previously described with respect to FIGS. 21A-21B and 22A-22B. In preferred embodiments, the outer diameter of the outer anchor is less than 4 mm and no more than 3.5 mm and the overall length of the inner and outer anchors when coupled together is less than 15 mm, and more preferably less than 12 mm. The inner and outer anchors are preferably each a single piece molded construct, preferably being molded from a polymer such as PEEK or carbon-fiber filled PEEK. One of skill in the art will appreciate that any of the other cinching mechanisms described herein my easily be substituted for the cinching mechanism shown in FIG. 23.

Figure 24A:
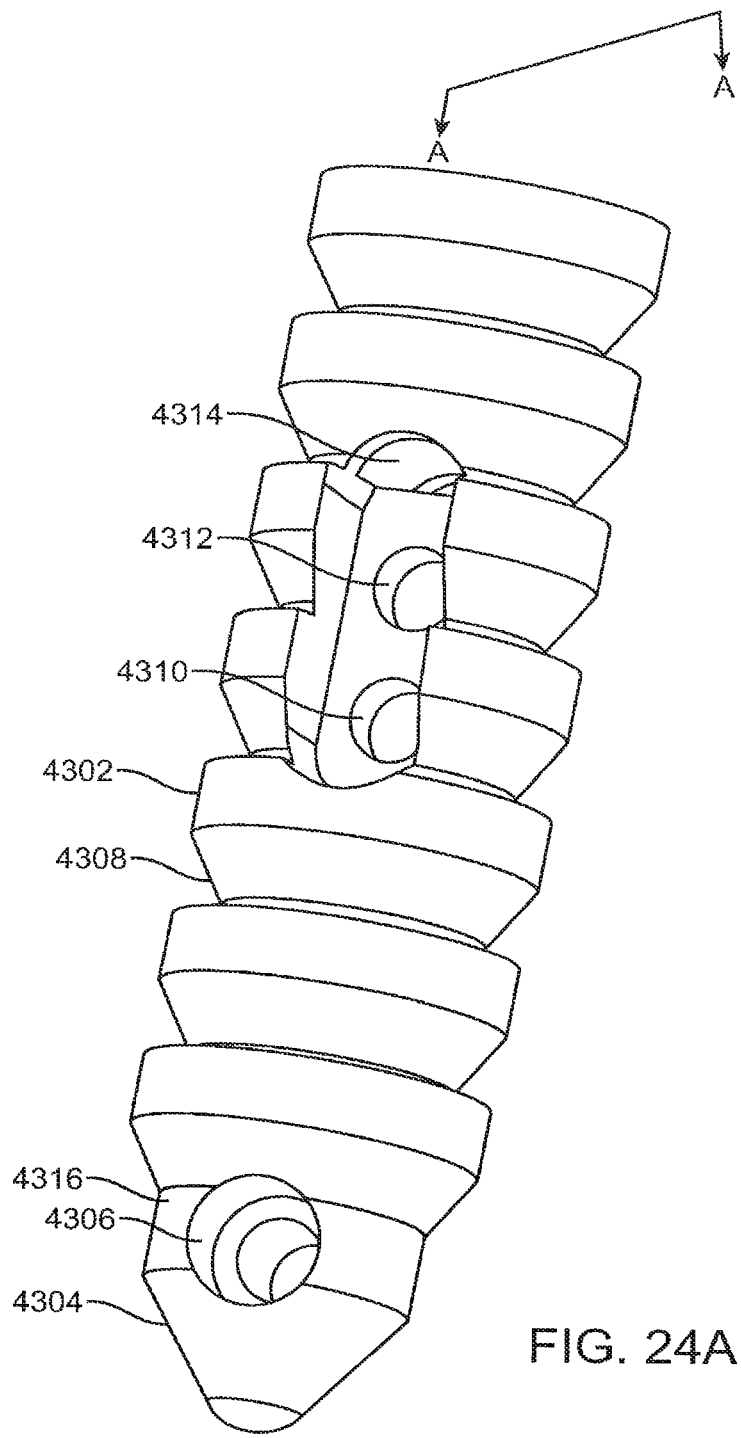
FIGS. 24A-24B illustrate still another exemplary embodiment of a suture anchor.
Figure 24B:
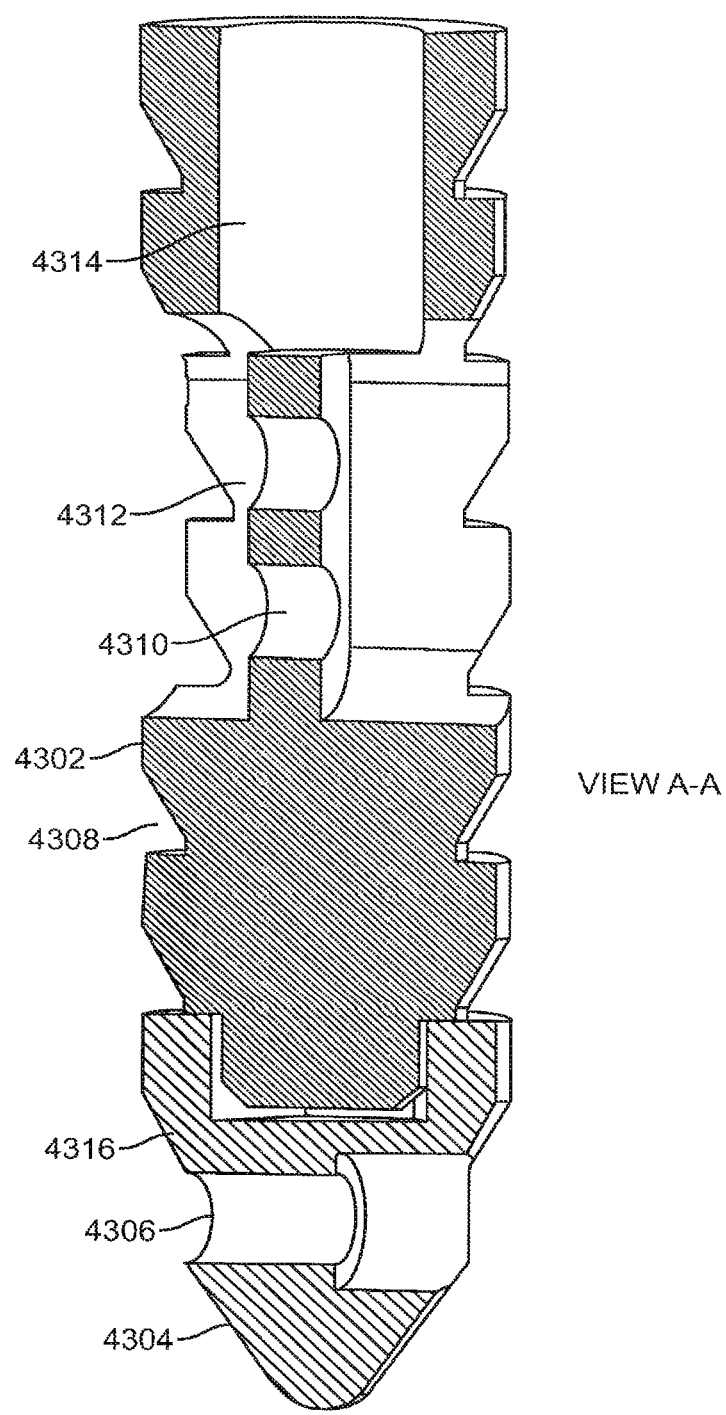

FIG. 24A illustrates a perspective view of another exemplary embodiment of a suture anchor having two stacked anchors and a cinching or locking mechanism for the suture. FIG. 24B is a cross-sectional view of the anchor in FIG. 24A taken along line A-A (along the longitudinal axis and after the anchor has been rotated approximately 90 degrees). The anchor system includes a top anchor 4302 and a bottom anchor 4316. The bottom anchor generally consists of several cylindrical sections of varying diameters. The conical distal end 4304 of the bottom anchor 4316 is tapered or pointed to facilitate driving the anchor directly into bone or other tissue or to help center the bottom anchor into an existing pre-drilled hole. A channel 4306 passes transversely through the bottom anchor and may be used to fix a suture thereto. As shown in FIG. 24B, the channel 4306 has a smaller diameter section large enough to accommodate the diameter of the suture, and a larger diameter section which allows a knot to be tied in the suture, the knot being too large to pass through the smaller diameter section, thereby securing the suture in the channel. A proximal portion of the bottom anchor 4316 has a central cavity adapted to receive and couple with the distal tip of the top anchor 4302. Both the top anchor 4302 and bottom anchor 4316 have a plurality of circumferential ribs 4308 disposed on their exterior to help hold the anchors in bone or tissue. Ribs 4308 each have an angled bevel on their distal edges to allow the anchor to pass more easily into bone or tissue, while having a flat proximal aspect that engages the tissue or bone into which the anchor is disposed to resist migration of the anchor proximally. The top and bottom anchors are preferably of the same diameter so as to fit snugly in the same pre-drilled hole. The distal tip of the top anchor 4302 is received in the cavity in the proximal portion of the bottom anchor 4316 and preferably includes some means of coupling the two anchors together, such as a friction fit between the interconnecting parts, or a coupling mechanism similar to that described in other embodiments disclosed herein. The proximal end of the upper anchor 4302 includes a central channel 4314 that allows the suture to pass through into a recessed central portion of the anchor which includes a flattened region having apertures 4310, 4312 therethrough. The suture may be threaded through apertures 4310, 4312 as described in the embodiments of FIGS. 21A-21B and FIGS. 22A-22B. In use, with the suture pre-attached to bottom anchor 4316 and pre-threaded through apertures 4310, 4312, the bottom anchor 4316 is driven directly into bone or inserted in a pre-drilled hole, and the top anchor 4302 is then looped around or passed directly through a penetration in the tissue to be repaired. Top anchor 4302 is then inserted into the same hole in which bottom anchor 4316 is positioned until its distal tip seats within the proximal end of the bottom anchor. The suture may then be adjusted or locked as described above. It will be understood that the top anchor 4302 may have a sharpened distal tip to allow it to penetrate directly through the tissue to be repaired without need for a separate instrument to create a penetration.

FIGS. 25A-25B illustrate yet another exemplary embodiment of a suture anchor with cinching mechanism. FIG. 25A is a cross-sectional view of FIG. 25B. The suture anchor 1402 has a tapered or pointed tip 1404 to help align it with a hole in the bone or to provide a tip that may be driven directly into bone. A cylindrical housing 1406 surrounds the cinching mechanism which includes two central walls 1408, 1412 that are offset from one another in a direction transverse to the longitudinal axis of the anchor 1402. The lower central wall 1408 has a lower aperture 1410 passing therethrough and an upper aperture 1414 is created by the space between the two offset walls 1408, 1412, forming a bar 1422 between the apertures. The top of the anchor is sealed except for an opening 1420 that is sized to allow the suture S to enter and exit the anchor. A first extremity 1418 of suture S enters the anchor through opening 1420 and travels down a first side of central wall 1412. The suture then crosses the central wall to the opposite, second side of the wall 1412 by passing through a gap created by the offset between the upper 1412 and lower 1408 walls. The suture S then travels down the second side and enters an aperture 1410 in the lower wall 1408. A second extremity 1416 of suture S exits the aperture 1410 on the first side and travels up the anchor and out of opening 1420. Opening 1420 helps orient the first and second extremities of suture 1416, 1418 so they are generally parallel with the face of upper wall 1412 as they enter and exit the anchor. In use, when the first extremity 1418 of suture S is pulled, the suture will advance through the cinching mechanism and thus the suture S length and tension may be adjusted. However, when the second extremity 1416 of suture S is pulled, first extremity 1418 is compressed against the upper wall 1412 and in particular the lower corner 1424 of upper wall 1412, creating friction against the suture and preventing movement of the suture in that direction. Aligning the suture extremities to be parallel with one another and with upper wall 1412, helps maximize friction between the suture extremities and the central wall. Thus, the suture may be adjusted in one direction only.

A further embodiment of a suture anchor according to the invention is illustrated in FIGS. 26A-26B. FIG. 26A illustrates a cross-section of the suture anchor and FIG. 26B illustrates another cross-section of the anchor rotated approximately 90 degrees. The suture anchor 1502 includes a tapered tip 1504 that generally takes the same form as those previously described above. A cylindrical housing 1518 having a central channel 1516 surrounds the cinching mechanism which comprises a barrel insert 1508 disposed in a transverse bore 1506 in the housing 1518. The barrel insert 1508 is transverse to the longitudinal axis of the anchor and preferably is orthogonal to the longitudinal axis. FIG. 26C illustrates the barrel insert 1508 removed from the anchor. The barrel 1508 has an upper aperture 1512 and a lower aperture 1514, both sized to accept suture, which are configured and operate in a manner similar to those described above in connection with FIGS. 21A-21B, and 22A-22B. An opening 1510 in the top of the housing 1518 allows the suture to enter and exit the suture anchor. This construction allows the cinching mechanism (barrel 1508) to be molded as a separate part from the remainder of the anchor, and the two parts are assembled by press fitting, bonding, or otherwise fixing barrel 1508 within bore 1506.

Figure 27A:
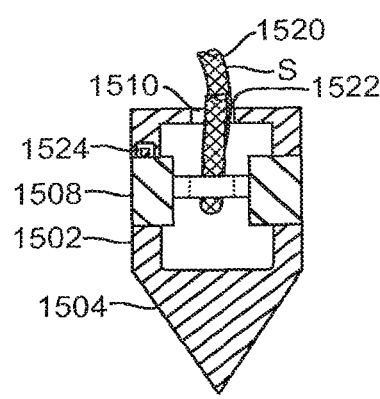
FIGS. 27A-27F illustrate another exemplary embodiment of a cinching mechanism.
Figure 27B:
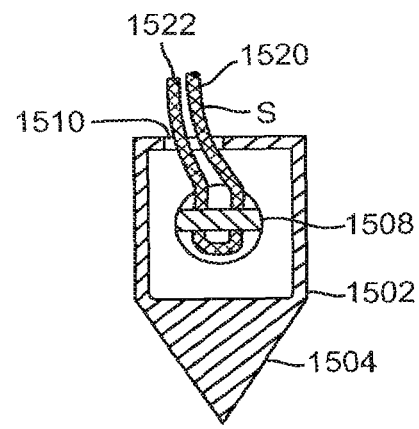

The previous embodiments have no moving parts and thus the suture may be adjusted and locked without actuating or moving any components. The size, shape, position, and orientation of all parts of the anchor remain the same whether the suture is being adjusted or locked. Other embodiments, such as those shown in FIGS. 27A-27F, include a cinching mechanism with at least one moving part. FIGS. 27A-27F illustrate a suture anchor similar to that shown in FIGS. 26A-26C, but in this embodiment the barrel 1508 is rotatable about a transverse axis from an unlocked position, shown in FIGS. 27A-27B, and 27F, to a locked position shown in FIGS. 27C-27D, and 27E. FIGS. 27A and 27B are cross-sections of the anchor taken at positions approximately 90 degrees apart from one another. In FIG. 27A, the suture S has a first extremity 1520 which extends downward through aperture 1510 and enters aperture 1512 in the rotatable barrel 1508 from a first side. The suture exits aperture 1512 on a second side opposite the first, crosses under the barrel and enters aperture 1514 from the second side, passes through aperture 1514 and a second extremity 1522 of the suture S exits the barrel on the first side. In the unlocked position, the barrel is positioned in the anchor such that both apertures 1512, 1514 are generally facing upwards in a direction parallel to the longitudinal axis of the anchor. A pin 1524 in barrel 1508 is movable within a curved channel in the wall of housing 1518 and prevents the barrel from rotating beyond certain limits. Thus, when a first extremity 1520 of the suture is pulled the barrel rotates into the unlocked position and is prevented from further rotation by engagement of the pin with the housing 1518. With the barrel 1508 in the unlocked position, friction against the suture is minimized and suture length and tension may be easily adjusted. However, when the second extremity 1522 of the suture S is pulled in a second direction opposite the first direction, the barrel will rotate into the locked position, preventing suture movement in that direction.

Figure 27C:
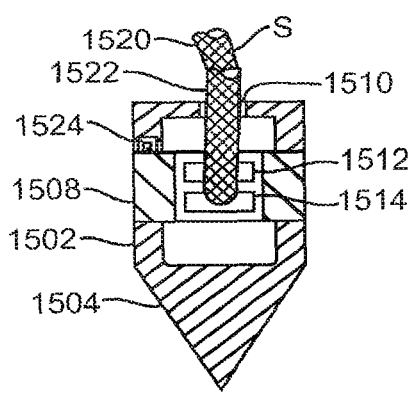
Figure 27D:
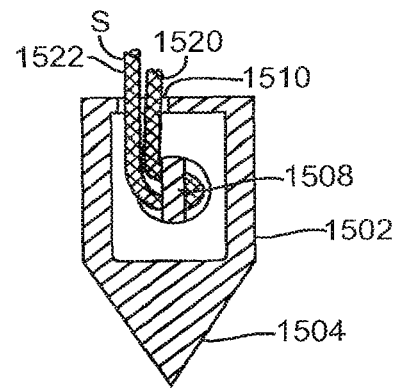
Figure 27E:
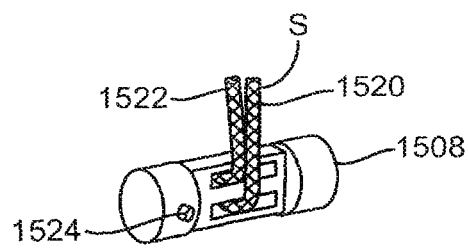
Figure 27F:
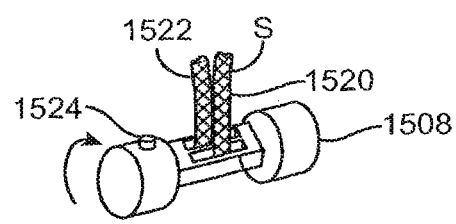

FIGS. 27C-27D illustrate the suture anchor of FIGS. 26A-26C with the barrel rotated into the locked position. FIGS. 27C and 27D are cross-sections of the anchor taken at positions approximately 90 degrees apart from one another. When the suture is pulled in the second direction, the barrel 1508 rotates and locks the suture. In the locked position, apertures 1512, 1514 are oriented to face transverse to the longitudinal axis of the anchor 1502, with both the first and second extremities 1520, 1522 of the suture extending from the apertures in a direction generally parallel to the lateral face of barrel 1508. Locking occurs because the first extremity 1520 is sandwiched between the second extremity 1522 and barrel 1508 such that, when second extremity 1522 is tensioned, the first extremity 1520 is compressed against the wall of barrel 1508 by the second extremity 1522.

Figure 28A:
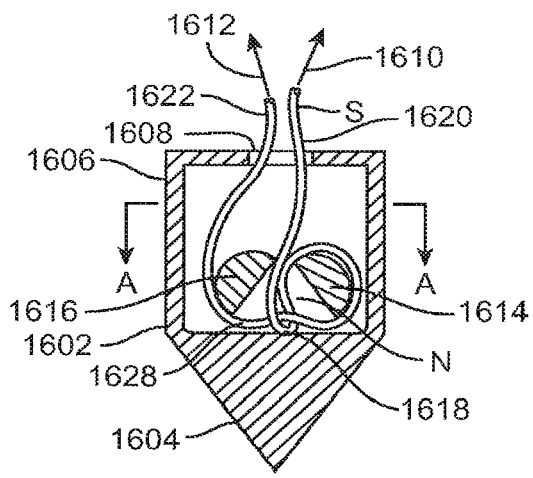
FIGS. 28A-28C illustrate an exemplary embodiment of a cinching mechanism.
Figure 28B:
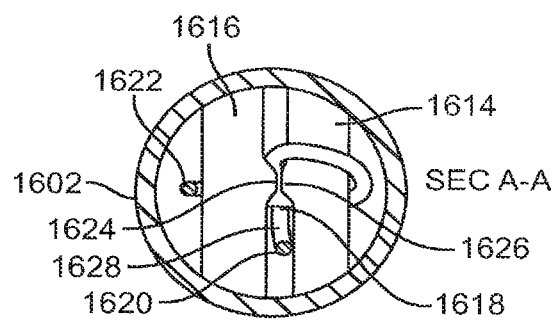
Figure 28C:
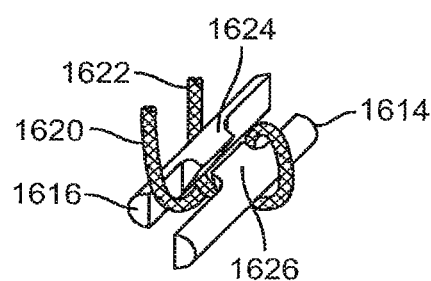

FIGS. 28A-28C illustrate another exemplary embodiment of a suture anchor having a cinching mechanism for adjusting the suture length and tension. This embodiment relies on the suture S crossing itself to create friction and compression on the suture that prevents movement of the suture in one direction while allowing movement in the opposite direction. FIG. 28A is a cross-section of the suture anchor 1602 which has a tapered or pointed tip 1604 that generally takes the same form as previously described suture anchor tips. A cylindrical housing 1606 encloses the cinching mechanism which includes two guide members 1614 and 1616 transversely positioned in the suture anchor housing relative to the longitudinal axis of the suture anchor. Guide members 1614, 1616 are separated by a gap therebetween. An upper opening 1608 allows the suture S to enter and exit the suture anchor. Guide members 1614, 1616 preferably have enlarged middle portions 1624, 1626 which extend toward each other, and may optionally engage or be integrally attached to each other. The undersides of middle portions 1624, 1626 comprise angled surfaces that merge toward one another, creating a notch N. A first extremity of suture 1622 enters the suture anchor through opening 1608 and partially encircles the first guide member 1616 and the second guide member 1614. After the suture is looped over the top of guide member 1614, it bends downward between the two guide members and forms a loop 1618 around an intermediate segment of suture 1628 extending across notch N. The suture then extends upward between the two guide members and a second extremity 1620 of the suture S exits the suture anchor through opening 1608. FIG. 28B illustrates a cross-section of anchor 1602 taken along line A-A in FIG. 28A.

FIG. 28C illustrates the path of the suture S around the guides in greater detail. In use, the first extremity of suture may be pulled in the direction indicated by arrow 1612 thereby allowing the suture length and tension to be adjusted. In this direction, the suture may pass freely around the guide members without binding. However, when the second extremity of suture 1620 is pulled in the direction indicated by arrow 1610, the loop 1618 tightens around the intermediate segment 1628, drawing it into notch N. Intermediate segment 1628 is thus compressed against the middle portions 1624, 1626 of guide members 1614, 1616, thereby locking the suture in position.

Figure 29A:
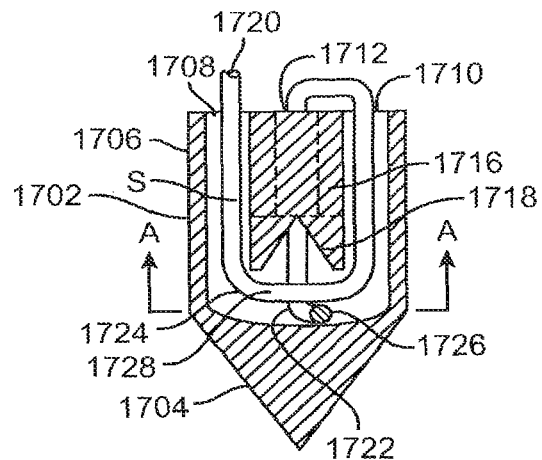
FIGS. 29A-29C illustrate still another exemplary embodiment of a cinching mechanism.
Figure 29B:
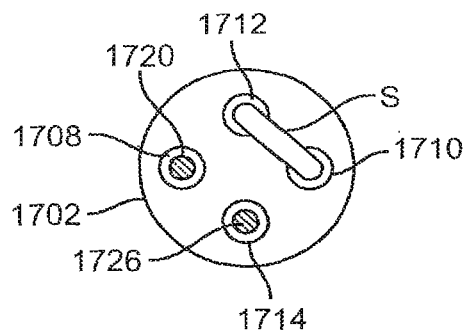
Figure 29C:
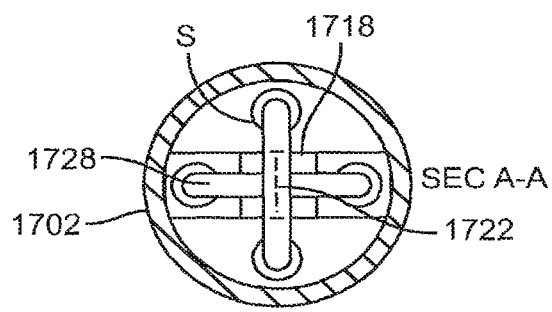

FIGS. 29A-29C illustrate yet another embodiment of a cinching mechanism in a suture anchor. FIG. 29A is a cross-section of a suture anchor 1702 having a tapered tip 1704 that generally takes the same form as tips previously describe above. The suture anchor has a cylindrical housing 1706 that surrounds the cinching mechanism. A plurality of openings 1708, 1710, 1712 and 1714 on the top surface of the housing allow the suture to enter and exit the anchor. A first extremity 1720 of suture S enters aperture 1708 and extends into a central channel 1724 of the anchor. The cinching mechanism includes a partition 1716 having a notched end 1718 in the central channel 1724. The first extremity 1720 of the suture S extends down into the central channel 1724 and has an intermediate segment 1728 that extends underneath the partition 1716 transversely across notch 1718. Suture S then extends upward and exits the anchor from aperture 1710. The suture crosses over a top of the anchor and re-enters the anchor in aperture 1712, extends down into the central channel and forms a loop 1722 across the intermediate segment 1728 of suture in a direction parallel to notch 1718. A second extremity 1726 of the suture extends upward from loop 1722 and exits the suture anchor through a fourth aperture 1714 in the top of the anchor. FIG. 29B is a top view of the anchor and FIG. 29C is a cross-section of FIG. 29A taken along line A-A.

In operation, the first extremity of suture 1720 may be pulled in a first direction and the suture is advanced through the cinching mechanism thereby adjusting length or tension in the suture. However, when the second extremity 1726 is pulled in a second direction opposite the first direction, intermediate segment 1728 is drawn upward by loop 1722 into notch 1718, compressing it against partition 1716 and binding the suture to prevent its movement in the second direction.

Figure 30A:
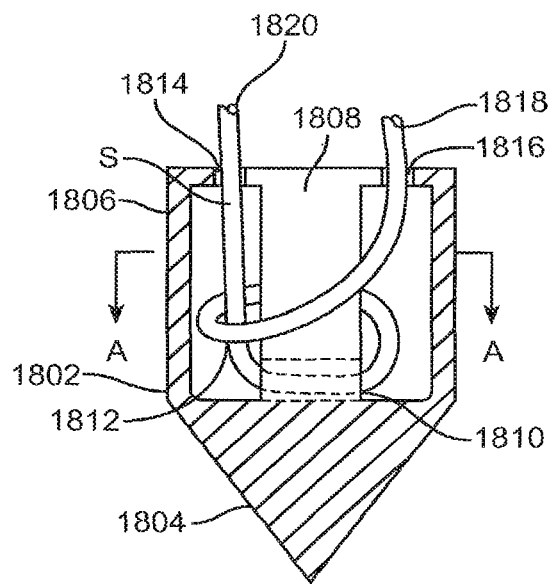
FIGS. 30A-30B illustrate yet another exemplary embodiment of a cinching mechanism.
Figure 30B:
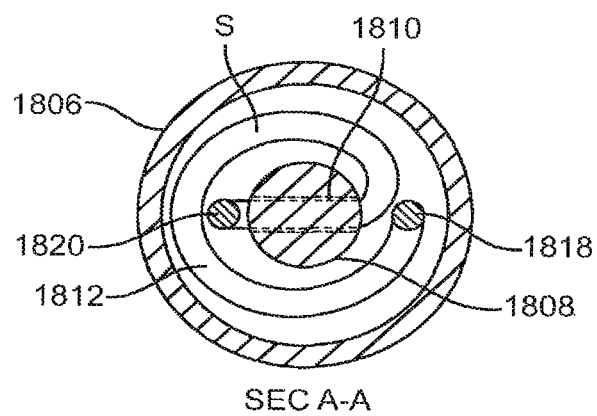

FIG. 30A illustrates a cut-away view of still another exemplary embodiment of a suture anchor having a cinching mechanism and FIG. 30B illustrates a cross-section of FIG. 30A taken along line A-A. The suture anchor 1802 has a tapered or pointed tip 1804 that generally takes the same form as other anchor tips previously described above. A cylindrical housing 1806 surrounds the cinching mechanism which includes a cylindrical central post 1808 disposed in the anchor and having an aperture 1810 extending therethrough. Openings 1814 and 1816 allow the suture S to enter and exit the anchor. In this embodiment, a first extremity 1820 of the suture S enters the anchor through opening 1814, travels down into the anchor and enters passage 1810 in the central post 1808 from a first side. The suture S then exits passage 1810 on a second side opposite the first side and then partially loops around the central post, crossing over itself to form a loop 1812 around the first extremity 1820 of suture S. A second extremity 1818 then travels up and out the anchor via opening 1816. When the first extremity 1820 of suture S is pulled in a first direction, the suture S is easily advanced through the cinching mechanism allowing the suture tension and length to be adjusted. However, when the second extremity 1818 is pulled in a second direction opposite the first direction, loop 1812 tightens and compresses first extremity 1820 against post 1808, resulting in friction between the suture and the central post 1808. This prevents the suture from being pulled in the second direction. Optionally, features such a bumps or ridges or coatings to enhance friction may be provided on the surface of post 1808 to enhance the resistive forces on suture S.

Figure 31A:
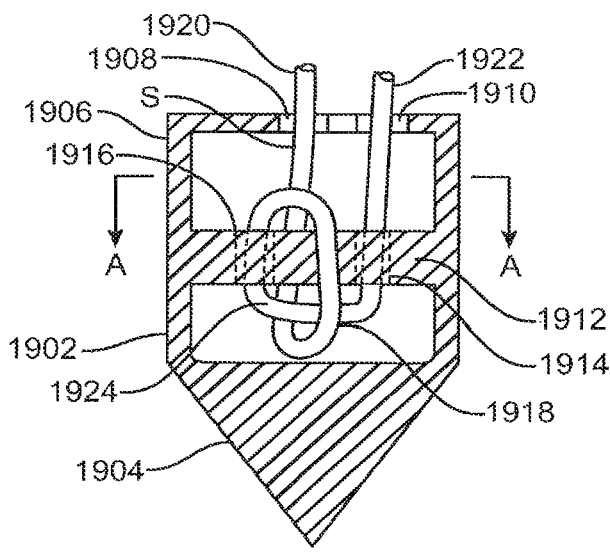
FIGS. 31A-31B illustrate another exemplary embodiment of a cinching mechanism.
Figure 31B:
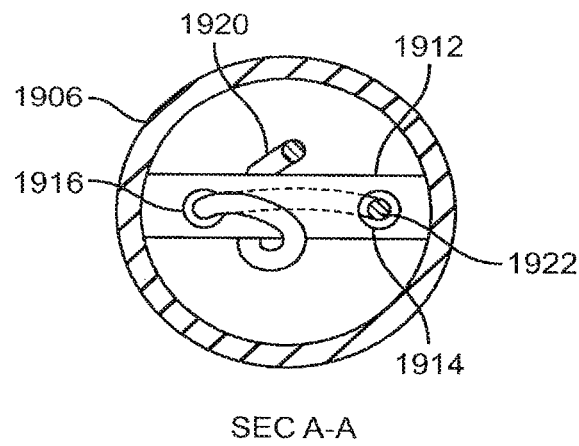

FIG. 31A illustrates another exemplary embodiment of a suture anchor where the suture crosses over itself. FIG. 31B illustrates a cross-section of FIG. 31A taken along line A-A. The suture anchor 1902 includes a pointed or tapered tip 1904 similar to other tips described above and the anchor also has a cylindrical housing 1906 similar to those described above. One of skill in the art will appreciate that while many of the embodiments described herein have a cylindrically shaped housing, other shapes may also be used in this or any of the embodiments disclosed herein, including, but not limited to square, rectangular, oval, triangular, or other symmetric and non-symmetrical configurations. The top of the housing has two apertures 1908, 1910 that allow the suture S to enter and exit the anchor. A single aperture accommodating both extremities of the suture is also possible. In this embodiment, the cinching mechanism includes a central bar 1912 that is disposed in the anchor transverse to the longitudinal axis of the anchor, preferably orthogonal. The central bar 1912 includes two passages 1914, 1916. In operation, a first extremity 1922 of the suture S enters aperture 1910 and travels downward into the anchor and enters passage 1914 from the top. The suture then exits passage 1914, and has an intermediate segment 1924 disposed substantially parallel along the underside of central bar 1912. Suture S then passes through passage 1916, loops around the central bar 1912 and forms a loop 1918 over the intermediate segment 1924. A second extremity 1920 of the suture S then runs upward and out of the anchor through aperture 1908. The suture anchor operates similarly to other embodiments described above where the suture crosses over itself. In this embodiment, the suture may be advanced when the first extremity 1922 is pulled in a first direction since the suture does not bind against itself or the central bar. However, when the second extremity 1920 of suture S is pulled in a second direction opposite the first direction, loop 1918 tightens up around intermediate segment 1924, compressing it against bar 1912 to create friction between the suture and the central bar which prevents the suture from moving. Again, bar 1912 may be provided with friction-enhancing features or a coatings to enhance the resistive force on suture S.

Figure 32A:
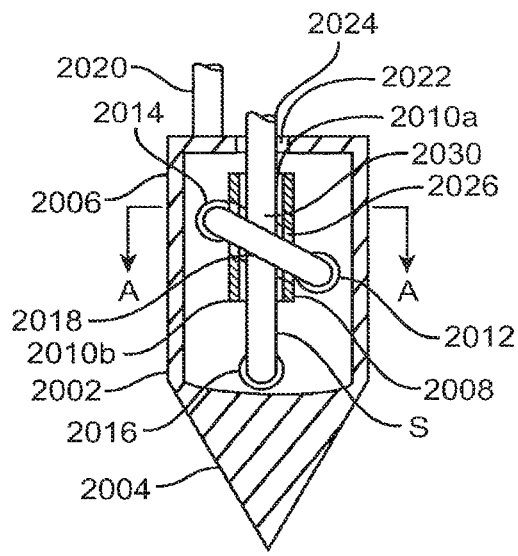
FIGS. 32A-32C illustrate another exemplary embodiment of a cinching mechanism.
Figure 32B:
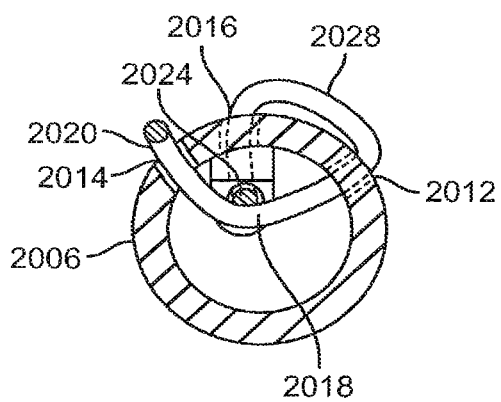
Figure 32C:
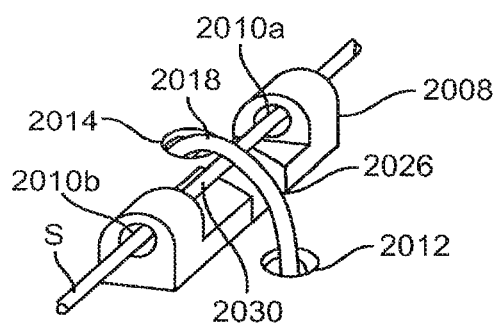

FIG. 32A illustrates another exemplary embodiment of a suture anchor where the suture crosses over itself. FIG. 32B is a cross-section of FIG. 32A taken along line A-A, and FIG. 32C highlights a portion of the cinching mechanism in greater detail. The suture anchor 2002 includes a tapered or pointed tip 2004 similar to other anchor tips described previously and the anchor has a cylindrical housing 2006 with apertures 2012, 2014, and 2016 in a sidewall of the housing. Aperture 2022 is in a top surface of the housing. The cinching mechanism includes a cradle 2008 having eyelets 2010*a*, 2010*b* and a V-notched channel 2026 for holding the suture S. The V-notch is transverse to the longitudinal axis of the cradle. Cradle 2008 may be integrally formed with housing 2006 or may be a separate component attached to the inside wall of the anchor housing 2006 using methods well known in the art (e.g. welding, screws, bonding, snap fitting, etc.). A first extremity 2024 of the suture S enters the anchor and extends through eyelets 2010*a*, 2010*b* across the cradle 2008, with an intermediate portion 2030 of suture S being substantially parallel to the longitudinal axis of the cradle and transverse to V-notched channel 2026. The suture then exits a lower portion of the anchor via a side aperture 2016. The suture 2028 then wraps partially around an external surface of the housing and re-enters the anchor via another side aperture 2012, The suture S then crosses over intermediate segment 2030 in a direction substantially parallel to V notched channel 2026 and exits the anchor via aperture 2014, forming a loop 2018. A second extremity 2020 then extends upward away from the anchor. The first extremity of suture 2024 may be pulled in a first direction thereby adjusting suture tension or length, however, when the second extremity 2020 of the suture is pulled in a second direction opposite the first direction, the loop 2018 tightens down upon intermediate segment 2030, pulling it into V-notched channel 2026 to create friction between the suture and the cradle, thereby preventing the suture from moving in the second direction. Preferably, channels or recesses (not shown) are provided in the outer wall of the anchor to receive those portions of the suture running along the exterior of the anchor to allow the suture to slide easily even when the anchor is placed in bone.

Figure 33:
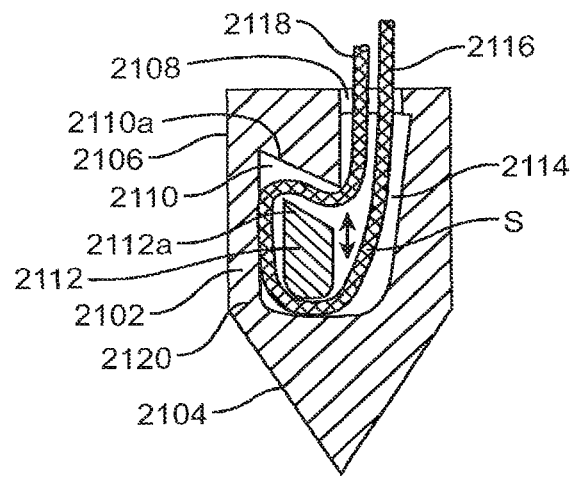
FIG. 33 illustrates another exemplary embodiment of a cinching mechanism.

FIG. 33 illustrates another embodiment of a suture anchor with a cinching mechanism. The suture anchor 2102 includes a pointed or tapered tip 2104 similar to those previously described and has a cylindrical housing 2106 containing the cinching mechanism. An aperture 2108 on the top surface of the housing allows the suture S to enter and exit the anchor. A central channel 2114 directs the suture toward a sliding wedge 2112 which is captured in a channel 2110 of the anchor. The sliding wedge may have any number of shapes, but in this embodiment includes an angled upper surface 2112*a* that corresponds to the angled upper surface 2110*a* of the channel 2110 in which the wedge slides. Preferably the angled upper surface 2110*a* forms an angle with the longitudinal wall 2120 of central channel 2114 which is less than 90 degrees, more preferably less than about 80 degrees, to increase the friction on the suture when second extremity 2116 is tensioned (described below). The upper surface 2112*a* of the wedge 2112 forms a similar angle with the side wall of wedge 2112, forming an acute angle along the upper edge. The first extremity 2118 of the suture enters the anchor via aperture 2108 and extends downward into central channel 2114 and then loops around and partially encircles the sliding wedge 2112. A second extremity 2116 of the suture S then extends upward through the central channel 2114 and exits the anchor through aperture 2108. The sliding wedge 2112 allows the suture S to be adjusted in one direction while constraining movement in a second direction opposite the first direction. The suture may be adjusted in the first direction when the first extremity 2118 is pulled because the suture S can pass easily around the sliding wedge 2112. However, when the second extremity 2116 of the suture S is pulled in the second direction opposite the first direction, the portion of the suture looped around the lower side of the sliding wedge will pull the sliding wedge upward until the upper surface 2112a compresses the suture S between the sliding wedge and the angled wall 2110a of channel 2110 preventing the suture from moving in the second direction. Moreover, the acute angle of the upper corner of the wedge provides a sharp edge which pinches the suture between the sliding wedge and the wall of channel 2110, increasing resistance of its movement.

Figure 34A:
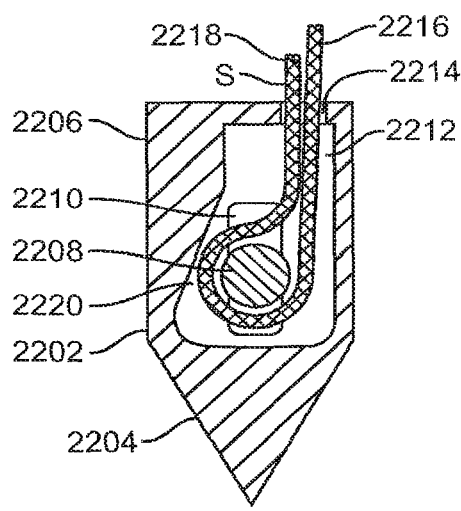
FIGS. 34A-34B illustrate another exemplary embodiment of a cinching mechanism.
Figure 34B:
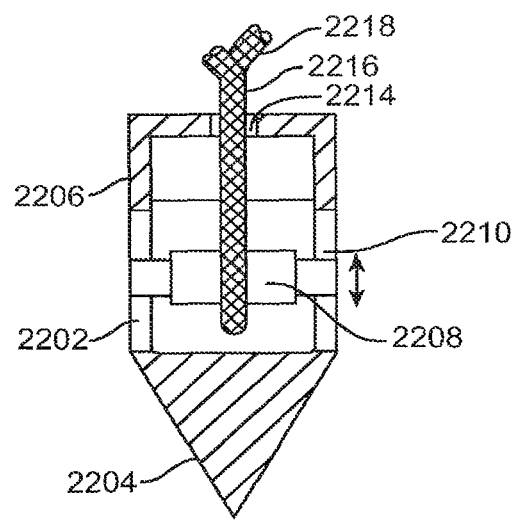

FIG. 34A illustrates a cross-section of another embodiment of a suture anchor having a cinching mechanism. FIG. 34B is also a cross-section of the anchor, this time rotated approximately 90 degrees relative to that of FIG. 34A. The anchor 2202 includes a tapered or pointed tip 2204 that generally takes the same form as other anchor tips previously described. The anchor also has a cylindrical housing 2206 that holds the suture and cinching mechanism and a top surface of the housing includes an aperture 2214 which allows the suture S to enter and exit the anchor. In this embodiment, a pin 2208 slides along a slot 2210 in a sidewall of the housing and serves as the wedging element. A first extremity 2218 of suture S enters the anchor through aperture 2214 and extends downward through a central channel 2212. Central channel 2212 has a sloping sidewall 2220 that narrows the width of the central channel as aperture 2214 is approached. The suture partially encircles the sliding pin 2208 and then a second extremity 2216 of the suture extends upward through the central channel 2212 and exits the anchor via aperture 2214. Aperture 2214 is laterally offset from the axis along which pin 2208 slides such that the second extremity 2216 of the suture is directed in a lateral direction from pin 2208 while the first extremity 2218 is generally parallel to the axis of movement of pin 2208. In operation, when the first extremity 2218 of suture S is pulled in a first direction, the lateral component of the force vector on pin 2208 keeps pin 2208 from being forced upward toward the sloping wall 2220 and allows the suture S to slip around the pin 2208. Thus, when the suture is pulled in the first direction, suture length or tension may be adjusted. When the second extremity 2216 of suture S is pulled in a second direction opposite the first direction, the forces on the suture will pull the sliding pin upward along the slot 2210. As the pin moves upward, the space between the pin and sloping wall 2220 decreases, resulting in the suture S being compressed between the pin and the sloping wall 2220, thereby locking the suture and preventing it from moving any further. Thus the cinching mechanism allows the suture to be adjusted when pulled in one direction and locked in the opposite direction.

Figure 35:
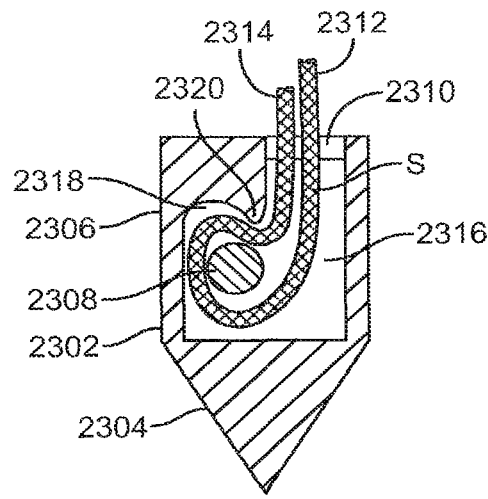
FIG. 35 illustrates another exemplary embodiment of a cinching mechanism.

FIG. 35 illustrates a cross-section of yet another embodiment of a suture anchor having a cinching mechanism. This embodiment is similar to that of FIG. 33 except that a stationary pin is provided in place of the sliding wedge. The anchor 2302 includes a pointed tip 2304 and a cylindrical housing 2306. A pin 2308 is mounted transversely in a central channel 2316. A first extremity 2314 of suture S enters the anchor through an aperture 2310 and extends downward into central channel 2316 and then the suture loops around and partially encircles the pin 2308. A second extremity 2312 then extends upward and out of the anchor through aperture 2310. Preferably central channel 2316 forms an upper wall 2318 opposite the upper side of pin 2308 which is curved or angled so as to form an acutely angled edge 2320 around which the first extremity passes. Suture length or tension may be adjusted by pulling the first extremity in a first direction and this allows the suture to pass freely through the anchor and cinching mechanism. When the second extremity 2312 of the suture is pulled in a second direction opposite the first direction, the second extremity 2312 compresses the first extremity 2314 against the wall of central channel 2316 and against edge 2320, pinching the suture S therebetween and preventing movement in the second direction. In alternative embodiments, the pin 2308 may rotate in place about its longitudinal axis, thereby facilitating the movement of the suture thereover when the first extremity 2314 is tensioned.

Figure 36A:
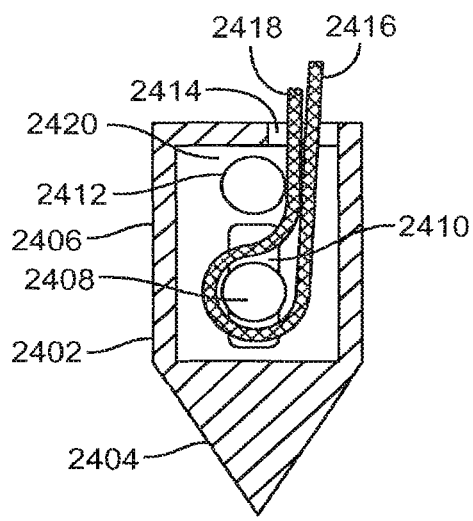
FIGS. 36A-36B illustrate an exemplary embodiment of a cinching mechanism.
Figure 36B:
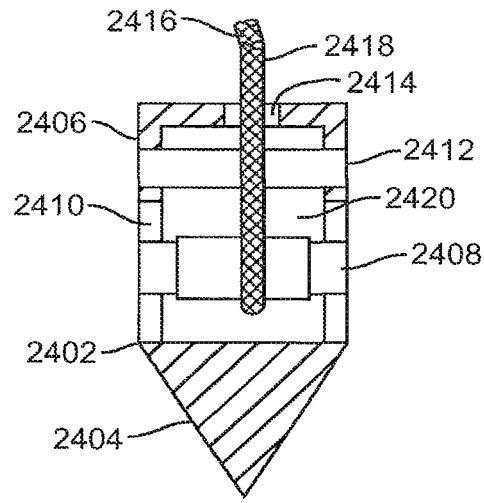

FIG. 36A illustrates a cross-section of another exemplary embodiment of a suture anchor having a cinching mechanism. FIG. 36B illustrates a cross-section of the embodiment in FIG. 36A rotated approximately 90 degrees. This embodiment is similar to that shown in FIGS. 34A-34B, except a fixed pin 2412 is provided in place of the sloping wall of the earlier embodiment. Anchor 2402 includes a pointed tip 2404 and a cylindrical housing 2406. A sliding pin 2408 is oriented transversely across housing 2406 and moves up and down along slot 2410 in the housing toward and away from fixed pin 2412 which is mounted transversely near the upper or proximal end of the housing. Both pins are generally parallel to one another and transverse to the longitudinal axis of the anchor, preferably orthogonal. A first extremity 2418 of the suture enters the anchor via aperture 2414 and extends downward into central channel 2420 crossing under the fixed pin 2412 and looping around and partially encircling the sliding pin 2408. A second extremity 2416 of the suture S then extends upward through the central channel and exits the anchor through aperture 2414. As in the embodiment of FIGS. 34A-34B, aperture 2414 is preferably laterally offset from the axis along which the sliding pin 2408 slides, so that the first extremity 2418 of suture S is directed in a lateral direction from sliding pin 2408 in order to exit through the aperture. When the first extremity 2418 is pulled in a first direction, the suture S slips around sliding pin 2408 without forcing it toward fixed pin 2412, allowing suture S to pass freely through the anchor and cinching mechanism. Thus suture length and tension may be adjusted by pulling the suture in the first direction. When the second extremity 2416 is pulled in a second direction opposite the first direction, the suture pulls the sliding pin 2408 upward along slot 2410 until the suture S is pinched between the sliding pin 2408 and the fixed pin 2412. Thus the suture cannot move when pulled in the second direction.

FIG. 37A illustrates an embodiment of a suture anchor and cinching mechanism in the unlocked configuration and FIG. 37B illustrates the suture anchor and cinching mechanism in the locked configuration. The anchor 2502 has a tapered or pointed tip 2504 similar to those previously described and also has a cylindrical housing 2506 with a central channel 2516 and an aperture 2508 on a top surface which allows the suture S to enter and exit the anchor. A pair of pins 2512, 2514 are mounted to housing 2506 transversely across central channel 2516 and are separated by a gap. A split retainer ring 2510 is coupled to an inner wall of housing 2506 so as to be aligned with the gap. A first extremity 2522 of the suture S enters the anchor through aperture 2508 and extends downward into the central channel 2516, passing under the second pin 2514 and looping back over the top of the second pin 2514 and through the gap between the two pins. The suture crosses over an intermediate segment 2518 of the suture which extends across the gap, passes through the split ring retainer 2510 and then passes back through the gap between the pins, forming a loop 2524 around the intermediate segment 2518. A second extremity 2520 of the suture S then extends upward and exits the anchor through aperture 2508. As seen in FIG. 37A, when the first extremity 2522 of suture S is pulled in a first direction, the suture will pass freely through the anchor and cinching mechanism without pulling out of the split retainer ring 2510, thereby allowing suture to move so that length and tension may be adjusted. However, as seen in FIG. 37B, when the second extremity 2520 of the suture S is pulled in a second direction opposite the first direction, the suture will pull out from the split retainer ring 2510 and the loop 2525 will then pull intermediate segment 2518 into the gap between the pins, compressing the suture against the pins, and creating friction which prevents the suture from further movement.

Figure 38A:
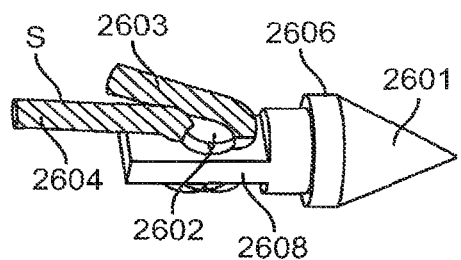
FIGS. 38A-38B illustrate an exemplary embodiment of a cinching mechanism.
Figure 38B:
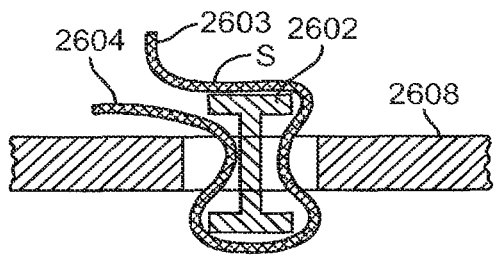

FIGS. 38A-38B illustrate another embodiment of a suture anchor having a suture locking mechanism. FIG. 38A is a perspective view of the suture anchor and FIG. 38B shows a cross section of the locking mechanism. Anchor 2606 includes a tapered or pointed tip 2601 similar to other tips described above, and the cinching mechanism includes a locking bar 2602 that slides along a central wall 2608. Suture S is threaded around the locking bar 2602. In this embodiment, the locking mechanism uses a floating suture locking mechanism within the anchor body. The suture S having ends 2603, 2604 is threaded through the floating locking bar 2602 such that it is activated by pulling one end of the suture to engage the lock. When the other end is tensioned, the lock can release providing adjustable tensioning capabilities. The central wall 2608 is configured to receive the sliding locking bar 2602. As tension on the suture thread end 2603 is increased the sliding member is pulled proximally locking the suture in position. When tension is exerted on thread end 2604 the system remains free to move and the suture slides past the locking bar. The floating locking bar 2602 can be constructed of a different material than the anchor, such as a compressible material like a soft durometer polymer such as silicone or urethane. With a softer, compressible material the suture may be locked as the material compresses around it during tensioning. In addition, the floating lock may be molded with a variety of surface features to cause a more secure lock, such as bumps, ridges or the like.

Figure 39:
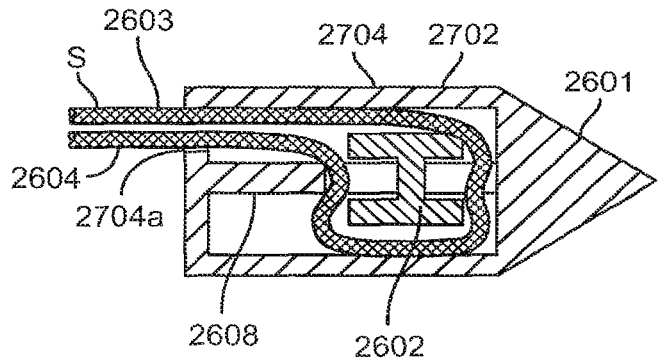
FIGS. 39-48 illustrate other exemplary embodiments of a cinching mechanism.

FIG. 39 illustrates a variation of the embodiment in FIGS. 38A-38B with the major difference being that the anchor 2702 includes a cylindrical housing 2704 that surrounds the cinching mechanism and also that the housing has an aperture 2704a on its top or proximal surface for the suture S to enter and exit the anchor. In this embodiment, the housing 2704 guides the first and second extremities 2603, 2604 of suture S along a path parallel to the axis of movement of the floating locking bar 2602. This ensures that when first extremity 2603 is tensioned, the force vectors are in the appropriate direction to pull floating locking bar proximally, thereby clamping the suture against the central wall 2608.

Figure 40:
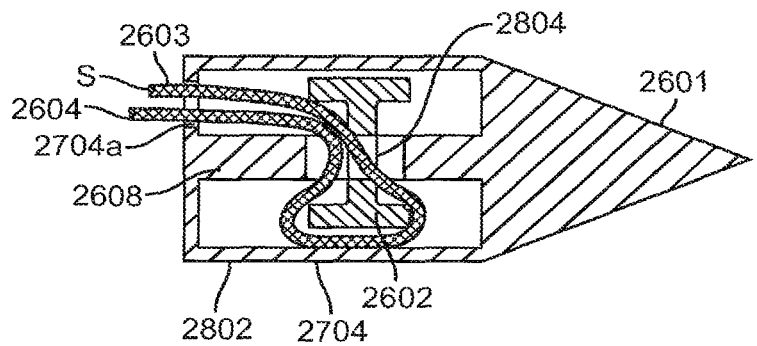

FIG. 40 illustrates a variation of the embodiment in FIG. 39, this time the floating locking bar 2602 in anchor 2802 includes an aperture 2804 in a middle portion thereof that allows the suture to pass therethrough instead of the suture passing over the top of the locking bar. This may allow more free movement of the suture when second extremity 2604 is tensioned, and may increase and the clamping force of the floating locking bar 2602 when first extremity 2603 is tensioned.

Figure 41:
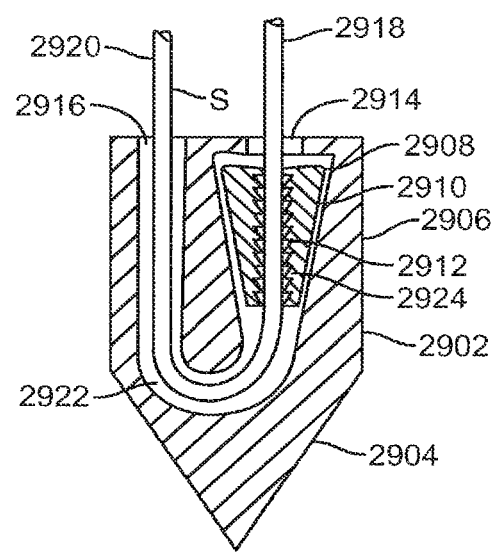

FIG. 41 illustrates a cross-section of another embodiment of a suture anchor and cinching mechanism. The anchor 2902 has a pointed or tapered tip 2904 similar to those previously described and also has a cylindrical housing 2906 with a pair of apertures 2914, 2916 which allow the suture S to enter and exit the anchor. The anchor also has a U-shaped central channel 2922 with a tapered portion 2908 on one side of the U. The cinching mechanism includes a split wedge 2924 having opposable jaws 2910 each with a plurality of teeth 2912 for pinching the suture S. The split wedge is slidably disposed in the tapered portion 2908 of the central channel 2922. A first extremity 2918 of suture S enters the anchor via aperture 2914 and extends downward into the central channel 2922 in between the jaws 2910. The suture exits the jaws and a second extremity 2920 of suture S passes through the bottom portion of the U shaped channel and exits the anchor through aperture 2916. In use, when the first extremity 2918 of the suture S is pulled in a first direction away from the anchor, wedge 2924 is pulled proximally in tapered channel 2908, allowing jaws 2910 to separate. This allows the suture to pass freely through the U-shaped channel and the jaws thereby allowing the suture length or tension to be adjusted. However, when the second extremity 2920 of the suture is pulled in a second direction opposite the first direction, away from the anchor, the suture will pull the split wedge 2924 downward into the tapered portion of the channel such that the jaws pinch the suture and the teeth 2912 bite into the suture, constraining suture movement relative to the anchor.

Figure 42:
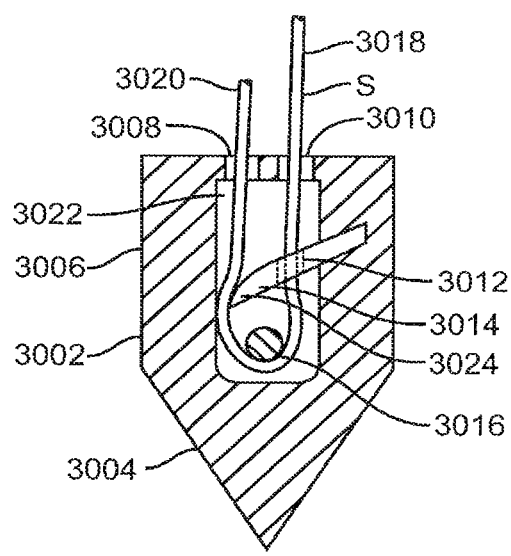

FIG. 42 illustrates a cross-section of another suture anchor embodiment. Anchor 3002 includes a tapered or pointed tip 3004 similar to those described above and has a cylindrical housing 3006 having a central channel 3022 and two apertures 3008, 3010 on the proximal or top surface of the housing for the suture S to enter and exit the anchor. An arm 3014 having a free distal end 3024 and an aperture 3012 in a proximal portion thereof is fixed to a wall of the anchor and cantilevers into the central channel. Preferably, distal end 3024 of arm 3014 has a beveled tip, preferably being beveled only on one side (e.g. the upper side as shown) or with a steeper angle on one side than the other, so that the tip engages the suture more readily when pulled in one direction vs. the other. For the same purpose, arm 3014 may be mounted non-orthogonally to the suture path (e.g. angled downwardly as shown), or constructed so as to resiliently deflect or bend preferentially in one direction vs. the other. A pin 3016 generally transverse to the longitudinal axis of the central channel is mounted near the bottom of the central channel. A first extremity 3018 of suture S enters the anchor via aperture 3010 and travels downward into the central channel 3022 and passes through aperture 3012. The suture then passes under the pin 3016 and past the distal end of the arm 3014. A second extremity 3020 of the suture then exits the anchor via aperture 3008. When the first extremity 3018 of the suture S is pulled in a first direction away from the anchor, arm 3014 deflects in the direction of suture movement and the suture S will pass freely through the anchor and cinching mechanism, allowing suture length or tension to be adjusted. However, when the second extremity 3020 is pulled in a second direction opposite the first, away from the anchor, the beveled tip of arm 3014 engages the suture and is pulled toward the opposing inner wall of the central channel, thereby pinching the suture and preventing its movement. The arm may be resilient and deflectable in which case the arm will deflect upward as the suture is pulled in the second direction and therefore the suture will be pinched between the arm and the wall of the central channel. Alternatively, the arm may be rigid but have a sharp tip that catches the suture and mechanically constrains it as it is pulled past the tip in the second direction. The suture may be round or flat and in some embodiments, the suture may have surface features which help it engage with the arm. For example, a flat suture may have discrete holes or ridges on it (similar to a cable tie).

Figure 43:
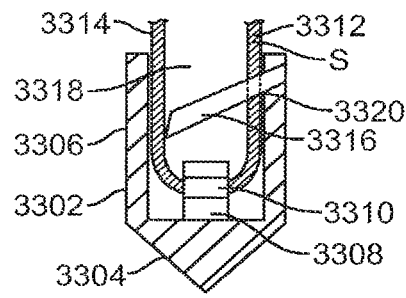

FIG. 43 is a schematic illustration of another suture anchor and locking mechanism. The anchor 3302 includes a pointed or tapered tip 3304 similar to those described above and also has a cylindrical housing 3306 with a central channel 3318. This embodiment is similar to that described above and illustrated in FIG. 42, having an arm 3316 cantilevered from a wall of the central channel with a distal tip configured to engage suture S. In place of pin 3016 in FIG. 42, this embodiment has a post 3308 secured to the bottom of the central channel 3318 with a passage 3310 through post 3308. A first extremity 3312 of the suture S enters the top of the anchor and passes through an aperture 3320 in the arm. The suture then passes through the passage 3310 in post 3308 and then the suture extends upward past the arm and a second extremity 3314 of the suture S exits the anchor. This embodiment works in substantially the same manner as embodiment in FIG. 42.

Figure 44:
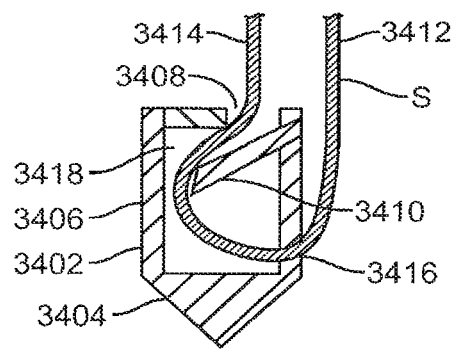

FIG. 44 is a schematic illustration of a suture anchor and locking mechanism. The anchor 3402 includes a pointed or tapered tip 3404 similar to those described above and also has a cylindrical housing 3406 having a central channel 3418 and an aperture 3408 on the top of the housing. An aperture 3416 passes through a sidewall of the housing near the bottom of the central channel and an arm 3410 is attached to a sidewall of the central channel and the arm cantilevers into the central channel. A first extremity 3412 of the suture S extends downward along an outer surface of the anchor and enters the central channel via aperture 3416. Preferably, a longitudinal channel or recess (not shown) is provided in the outer wall of the anchor which receives the suture and allows it to slide easily even when the anchor is placed in bone. The suture then passes around the arm and a second extremity 3414 exits the anchor via aperture 3408. The cinching mechanism operates substantially similarly to the embodiments described in FIGS. 42 and 43 above.

Figure 45:
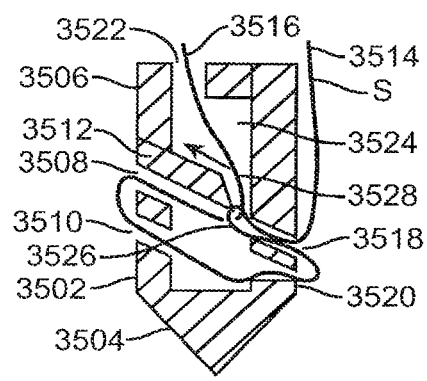

FIG. 45 shows another schematic of a suture anchor and locking mechanism. Anchor 3502 includes a pointed or tapered tip 3504 similar to those described above and the anchor also has a cylindrical housing 3506 with a central channel 3524 and having passages 3508 and 3510 through a sidewall of the housing and passage 3518 through a sidewall on the opposite side of the housing. An aperture 3522 is on the top of the housing so that the suture may enter and exit the anchor. An arm 3512 is attached to a sidewall of the central channel and extends outwardly into the central channel like a cantilevered beam. An extremity of the suture 3516 enters the anchor via aperture 3522 and then passes downward in the central channel and has a tip engaging segment 3528 that passes around the tip of arm 3512. The suture then exits the anchor via passage 3508, travels a short distance along an outer surface of the anchor and re-enters the anchor via passage 3510, crossing the channel and then again exiting the anchor via passage 3520. The suture re-enters the anchor via passage 3518 and forms a loop 3526 around the tip-engaging segment 3528 extending around arm 3512, the suture then exiting through passage 3518. The suture then extends upward along an outer surface of the anchor. Preferably, channels or recesses (not shown) are provided in the outer wall of the anchor to receive those extremities of the suture extending along the exterior to allow the suture to slide easily even when the anchor is placed in bone. In operation, when the suture is pulled in the direction of end 3514, the suture loop 3526 will pull the tip-engaging segment 3528 of the suture away from the arm thereby allowing the suture to move relative to the arm so that suture tension or length may be adjusted. When the suture is pulled in the opposite direction by tensioning end 3516, the suture is pulled into engagement with the arm, preventing the suture from passing, and thus the suture is locked.

Figure 46:
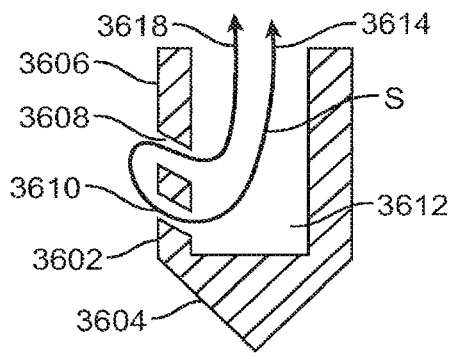

FIG. 46 is a schematic illustration of another suture anchor embodiment with locking mechanism. Anchor 3602 includes a tapered or pointed tip 3604 similar to those previously described above. A cylindrical housing 3606 includes a central channel 3612 and a pair of passages 3608, 3610 in a sidewall of the housing. An extremity 3618 of the suture S enters the anchor from the top of the central channel and extends downward into the channel. The suture then exits the anchor via passage 3608 and passes along an outer surface of the anchor and then re-enters the anchor via passage 3610. Again, a longitudinal channel or recess (not shown) is preferably provided on the outer wall of the housing 3606 between passages 3608, 3610 to receive the suture and allow it to slide freely without interference by surrounding bone or tissue. The suture then extends upward and an extremity 3614 of the suture S exits the anchor via the top of the channel. The passages 3608, 3610 may be angled so that the suture may pass through them in one direction, while resistance is met in the opposite direction. Thus, in this embodiment, when suture extremity 3618 is pulled away from the anchor, it will pass freely through the passages allowing suture length or tension to be adjusted. However, when suture extremity 3614 is pulled away from the anchor, suture extremity 3614 compresses suture extremity 3618 against the inner wall of the central channel 3612, constraining the suture from moving.

Figure 47:
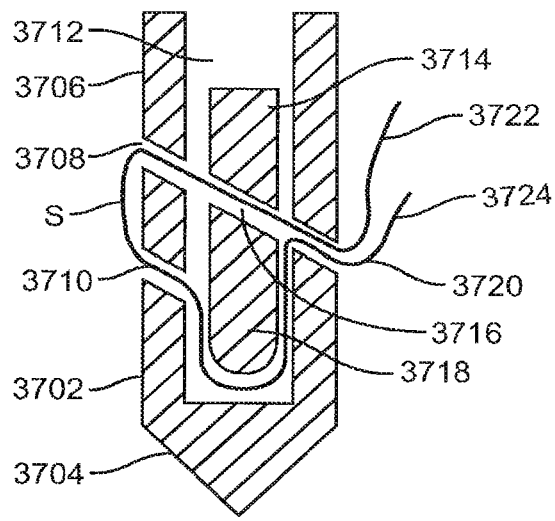

FIG. 47 is another schematic illustration of a suture anchor having a sliding clamping element. Anchor 3702 includes a tapered or pointed tip 3704 similar to those described above. The anchor also has a cylindrical body 3706 with a central channel 3712 extending therethrough. A pair of passages 3708, 3710 extend through a sidewall on one side of the anchor and another passage 3720 extends through the sidewall on an opposite side of the anchor. A sliding clamp 3718 is disposed in central channel 3712 so that it may travel up and down the central channel (e.g. the sliding clamp may be free-floating or may ride in slots in the sidewall of the anchor). A rigid stop 3714 is fixed in the central channel above (proximally of) the sliding clamp. A first extremity 3722 of the suture S extends downward and runs alongside an exterior surface of the anchor and then enters the anchor via passage 3720. The suture crosses the central channel through a transverse passage 3716 between the sliding clamp 3718 and the rigid stop 3714. The suture exits the anchor via passage 3708 and passes along an outer surface of the anchor and then re-enters the anchor via passage 3710, extending downward and under the sliding clamp 3718. A second extremity 3724 of the suture S then exits the anchor via passage 3720. Longitudinal channels or recesses (not shown) are preferably provided on the outer wall of the body 3706 between passages 3708, 3710 and from passage 3720 to the proximal end of the anchor to receive the suture and allow it to slide freely without interference by surrounding bone or tissue. In operation, the first extremity 3722 of suture S may be pulled in a first direction away from the anchor without binding, thereby allowing suture length or tension to be adjusted. When the second extremity 3724 of suture S is pulled away from the anchor in a second direction opposite the first direction, the suture will pull the sliding clamp 3718 upward, pinching the suture between the top of the sliding clamp and the bottom of the rigid stop 3714, thereby locking the suture in position.

Figure 48:
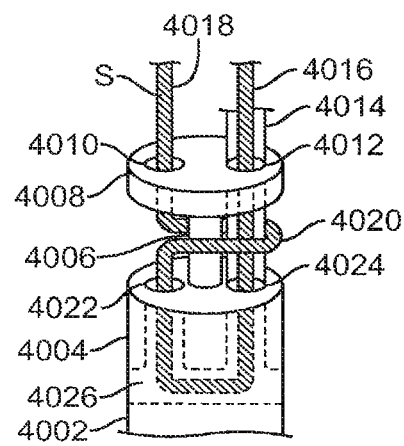

FIG. 48 illustrates another embodiment of a knotless cinching mechanism which has an optional feature to allow two-way suture movement and selective conversion to one-way cinching function. Anchor 4002 includes a cylindrical housing 4004 and may have any of the distal tips described herein. The housing 4004 has apertures 4022, 4024 on the top surface that form an entrance to and an exit from a U-shaped channel 4026 that holds a part of the suture S. A central post 4006 joins the top of the housing 4004 with an end plate 4008 having apertures 4010, 4012 therethrough. An optional lubricious sheath or suture cover 4014 is removably positioned through aperture 4012 so as to enclose a portion of the suture along post 4006 distal to aperture 4012. A first extremity 4016 of suture S enters aperture 4012 and extends downward alongside the central post 4006 entering the U-shaped channel 4026 via aperture 4024. The suture travels through the U-shaped channel and travels upward, exiting the U-shaped channel via aperture 4022. The suture then loops around the central post 4006, forming a loop 4020 which partially encircles the central post along with sheath 4014 and the first extremity 4016 of suture S. A second extremity 4018 of the suture S then extends upward and passes through aperture 4010 in the end plate 4008. The lubricious sheath 4014 covers a portion of the suture S extending through aperture 4012 and also a portion of the suture S underneath loop 4020. The lubricious sheath has sufficient radial strength to keep from collapsing on the underlying suture when loop 4020 is cinched down, and lubricous enough to allow the suture to slide through it. When the sheath 4014 is positioned over the suture, either the first extremity 4016 or second extremity of suture S may be pulled away from the anchor and the suture will pass freely through the anchor and cinching mechanism since the suture will glide through the lubricious sheath even though loop 4020 may be tightening around it. Once the sheath 4014 is refracted or removed the suture underlying loop 4020 may be engaged by the loop such that, when the second extremity 4018 of suture S is pulled in a second direction away from the anchor and opposite the first direction, loop 4020 will cinch down on first extremity 4016 to compress it and create friction between the suture and the central post, preventing the suture from moving in the second direction. Even with the sheath removed, however, applying tension to first extremity 4016 in the first direction will allow the suture to move. If a sufficiently flexible material is used, sheath 4014 may extend proximally over suture S a sufficient distance to allow the surgeon to grasp it. Alternatively, sheath 4014 may comprise a short and more rigid segment and it may be coupled to a flexible tether or length of suture (not shown) which may extend away from the surgical site, preferably out of the patient's body, to allow the surgeon to retract or remove the sheath at the desired time. It will be understood that the embodiment illustrated in FIG. 40 may also be used without sheath 4014, wherein it will operate solely as a one-way cinching mechanism as with other embodiments described herein.

Figure 49A:
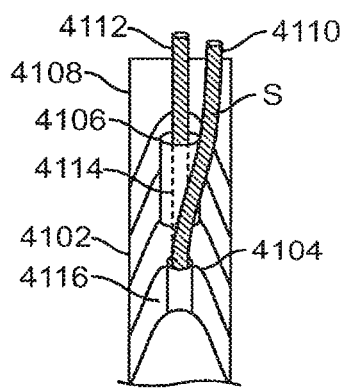
FIGS. 49A-49C illustrate another exemplary embodiment of a cinching mechanism.
Figure 49B:
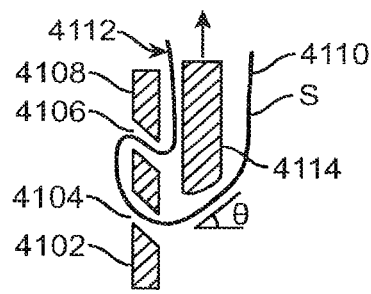
Figure 49C:
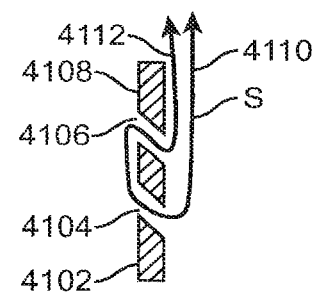

FIG. 49A illustrates another exemplary embodiment of a suture anchor having a locking mechanism. FIG. 49B schematically illustrates a side cross-sectional view of FIG. 49A. The anchor 4102 may have a cylindrical housing (not illustrated) and tip (not illustrated) similar to other embodiments described above and a central wall 4108 may be disposed in the anchor housing. Upper and lower apertures 4106, 4104 are disposed in wall 4108. A removable wedge element 4114 (best seen in FIG. 49B) is positionable in the anchor between a first extremity 4112 of the suture and a second extremity 4110 of the suture. The wedge element 4114 is arch-shaped on its inner side facing wall 4108 so as not to clamp the first extremity 4112 of suture S against wall 4108 and to allow suture S to slide. Wedge element 4114 may also include a longitudinal groove or channel 4116 on its outer side to receive the second extremity 4110 of the suture and allow it to slide. Wedge element 4114 preferably has a distal end which has a curvature or angle selected to guide suture S in a more lateral direction away from lower aperture 4104 so as to minimize friction with wall 4108 adjacent to the aperture. The first extremity 4112 of the suture S extends downward and substantially parallel with the central wall entering aperture 4106 from a first side and then travels along an outside surface of the central wall, entering aperture 4104 from a second side opposite the first side. The suture S then loops around the removable wedge element partially encircling it. A second extremity 4110 of the suture S then extends upward and out of the anchor. Thus, when the removable wedge element is disposed in between the suture and the central wall, the second extremity of the suture gently exits aperture 4104 and gently curves around the wedge. When the first extremity 4112 of the suture is pulled in a first direction away from the anchor, the suture will pass freely through the apertures of the central wall and thus the suture length or tension may be adjusted. Additionally, with the wedge element in place, the second extremity 4110 of the suture S may also be pulled in a second direction opposite the first direction and away from the anchor and the suture will also move freely through the cinching mechanism. Thus the suture S may be tightened or loosened by pulling the suture in either the first or the second direction. When the removable wedge element 4114 is removed from its position between the suture and the central wall, the angle that the suture exits aperture 4014 will increase and be close to perpendicular and the second extremity 4110 is allowed direct contact with first extremity 4112. Thus, when the second extremity 4110 of the suture S is pulled in the second direction, the suture will bind against an edge of aperture 4104 and second extremity 4110 will compress first extremity 4112 against wall 4108, preventing the suture from moving in the second direction. The apertures 4104, 4106 may be angled non-orthogonally to the face of the wall so as to optimize slidability and friction in different directions. For example, one or both of apertures 4104, 4108 may be angled to slope downward (distally) toward the inner side of the wall so as to create a sharper edge along the upper side of the aperture thereby increasing resistance on suture movement. Moreover, the shape of the removable wedge 4114 may also be adjusted to optimize slidability of the suture in the first and second directions. FIG. 49C illustrates the cinching mechanism when the removable wedge has been removed.

Figure 50A:
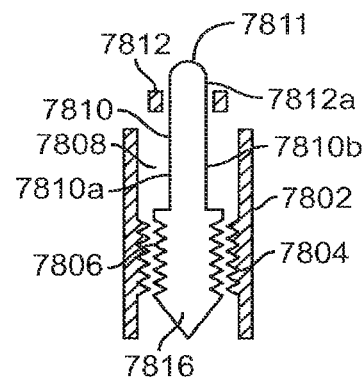
FIGS. 50A-50C illustrate another exemplary embodiment of a cinching mechanism.
Figure 50B:
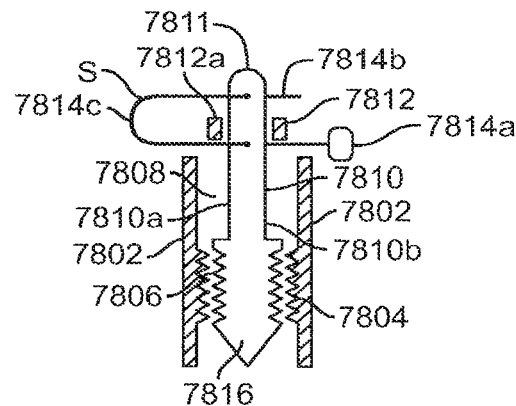
Figure 50C:
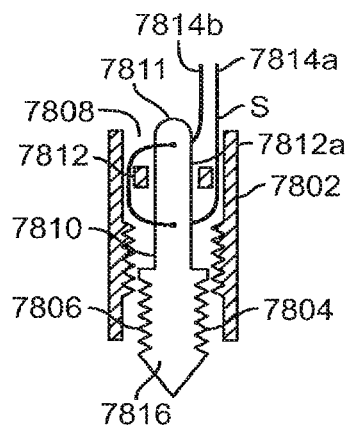

FIGS. 50A-50C illustrate cross-sections of another embodiment of a knotless suture anchor system having an outer anchor 7802 and an inner anchor 7816. FIG. 50A shows the anchor unloaded, FIG. 50B shows a suture S being loaded into the anchor, and FIG. 50C shows the anchor locked. The outer anchor 7802 has a central channel 7810 with internal threads or ribs 7804 for engaging the threads or ribs 7806 on the inner anchor 7816. A suture or wire guide 7810 forming a loop 7811 with legs 7810a, 7810b, is attached to the inner anchor 7816 and passes through an axial passage 7812a in a strangling member 7812 so as to act as a rail over which strangling member 7812 slides. In use, the inner anchor 7816 is retracted proximally or unthreaded sufficiently so that the strangling member 7812 is exposed from the central channel 7810. As seen in FIG. 50B, a lasso 7814a of suture, wire, or other flexible material passes through loop 7811 in wire guide 7810, around one side of strangling member 7812 and between the legs 7810a, 7810b of wire guide 7810 on the lower side of strangling member 7812 and has a free end 7814b and a capture loop 7814c on the opposite end. The anchor system is pre loaded with lasso 7814a threaded in this manner so that after a suture is passed through or around the tissue to be repaired, the suture ends may be passed through the capture loop 7814c and the free end of lasso 7814a then pulled to draw the suture through the wire guide loop both distally and proximally of strangling member 7812. Thus the one-way cinching mechanism may be threaded with a suture by the surgeon during a surgical procedure. The inner anchor 7816 is then advanced distally into the central channel 7808 so that the strangling member 7812 is disposed in the central channel and the two ends 7814a, 7814b extend proximally from the anchor 7802, as seen in FIG. 50C. Thus, when free end 7814a is pulled, the length or tension of suture S may be adjusted. However, when free end 7814b is pulled, the suture S will force the strangling member 7812 to move upward along the wire guide 7810 until the suture is pinched between a top portion of the strangling member 7812 and the wire guide 7810, thereby preventing further movement of the suture.

FIGS. 51A-51B illustrate another exemplary embodiment of a suture anchor cinching mechanism. FIG. 51A shows a schematic of the anchor and FIG. 51B illustrates a cross-section of the anchor. The anchor 7602 has a generally cylindrically shaped housing with a pointed distal tip 7604, a central channel 7606, and a strangling shuttle 7608 that slides along a suture or wire guide 7610. The wire guide 7610 has both ends 7612a, 7612b attached to a lower portion of the anchor 7602 and a looped region 7614 extends through a central passage 7607 through the strangling shuttle 7608. A suture S extends through the loop 7614 on one side of strangling shuttle 7608 and is wrapped around the shuttle 7608 passing between the two legs 7610a, 7610b of wire guide 7610 on the opposite side of strangling shuttle 7608 such that both free ends 7616a, 7616b extend proximally from the anchor 7602. In use, when free end 7616b is pulled, the length or tension of suture S may be adjusted as the suture will slide around the strangling shuttle 7608. However, when the other free end 7616a is pulled, the strangling shuttle 7608 will be pulled up and slide along the wire guide 7610 until a portion of the suture S is pinched between the top surface of the strangling shuttle 7608 and the loop 7614 of the wire guide 7610. Once pinched, the suture S will be constrained from further movement. Thus, the cinching mechanism allows one-way adjustment of the suture. FIG. 51C illustrates a perspective view of the strangling element 7608, except this time with two sutures S passing therearound. Thus, the cinching mechanism may be used to allow one-way adjustment of more than one suture. In this embodiment, free ends 7616a, 7618a may be pulled to adjust length or tension in the sutures, while pulling the opposite free ends 7616b, 7618b will lock the suture and prevent further movement.

Figure 52A:
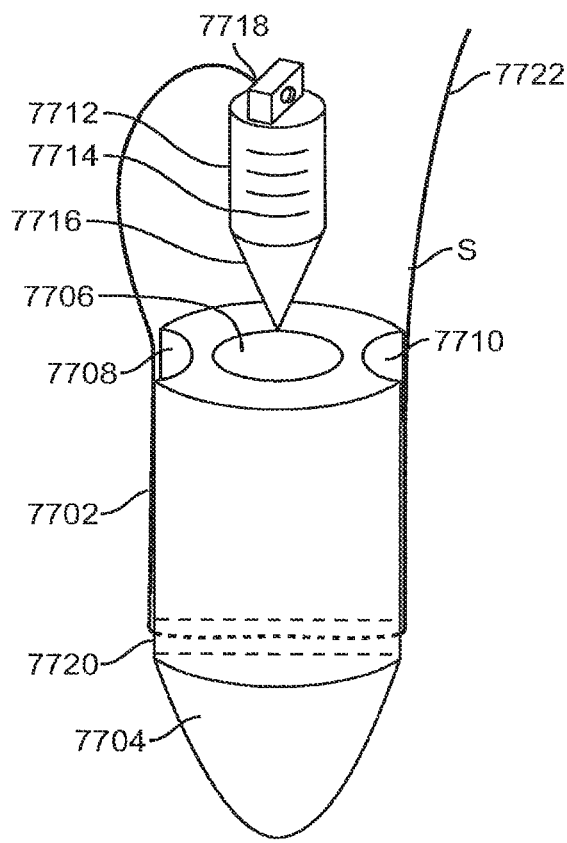
FIGS. 52A-52B illustrate an exemplary embodiment of a cinching mechanism.
Figure 52B:
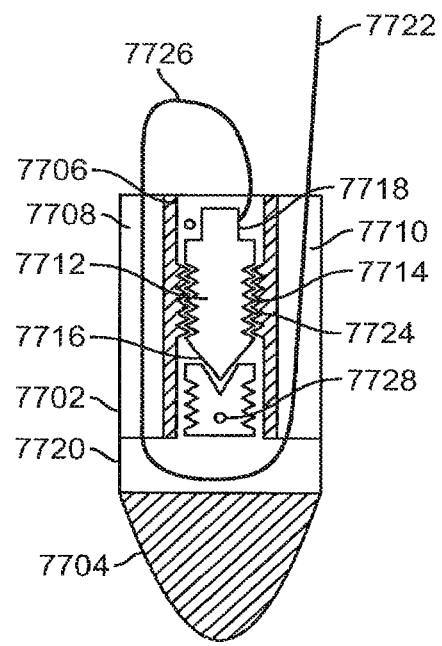

FIGS. 52A-52B illustrate still another exemplary embodiment of a knotless suture anchor system having an outer anchor 7702 and an inner tissue piercing anchor 7712. The outer anchor 7702 has a generally cylindrically shaped body with a tapered distal tip 7704, a central channel 7706 and a transverse channel 7720. Concave channels 7708, 7710 run axially along the outer surface of the outer anchor 7702 and allow suture S to seat therein without being pinched between the anchor and the bone. The outer anchor also has a floating element 7728 (seen in FIG. 52B) which slides axially along the central channel 7706. The inner tissue piercing anchor 7712 has a sharp pointed distal tip 7716 that allows the inner anchor 7712 to pass easily through tissue such as a torn labrum or rotator cuff and has ribs or threads 7714 or other surface features for engaging the corresponding surface features 7724 on the inner surface of outer anchor 7702. A length of suture S is attached with a knot 7718, crimp or other means to the inner anchor 7712. The suture then runs along an outer surface of the outer anchor 7702 in channel 7708 and passes through transverse channel 7720 and extends up along an opposite surface of the anchor 7702 in channel 7710. A free end 7722 extends proximally away from the anchors 7702, 7712. In use, damaged tissue (not illustrated) is captured by passing the piercing anchor 7712 therethrough or by looping the suture therearound to create a repair loop 7726. The inner anchor 7702 is then threaded or pushed into the central channel 7706 of the outer anchor 7702. As the inner anchor 7712 is advanced into the central channel 7706, it engages the floating element 7728 and forces the floating element downward until it pinches the suture passing through the transverse channel 7720, thereby locking the suture in position. An advantage of this type of suture anchor is that the inner anchor may be released from the outer anchor by unthreading, thereby allowing additional adjustments to suture length or tension.

Figure 53:
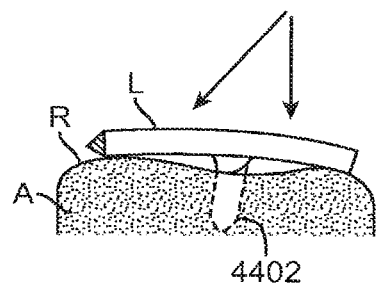
FIG. 53 illustrates obstruction of a pre-drilled hole by tissue.
Figure 54:
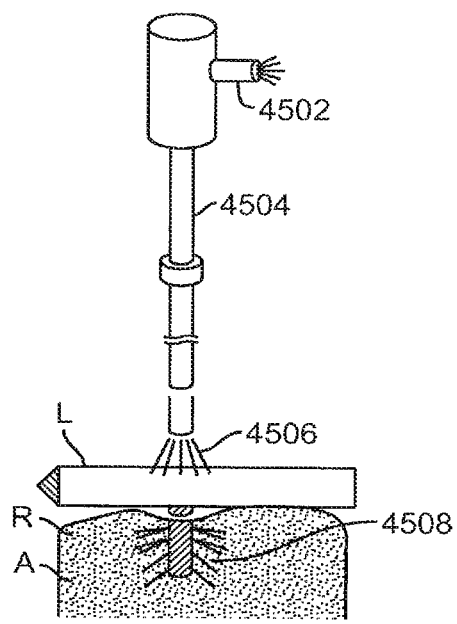
FIG. 54 illustrates an exemplary method of visualizing a pre-drilled hole.

Deployment:

Suture anchors often are placed into pre-drilled holes in the bone or other tissue substrate to which damaged tissue is to be re-attached. FIG. 53 shows a pre-drilled hole 4402 obscured by a torn labrum L that is to be re-attached to the rim R of an acetabulum A. In the case of re-attaching a torn labrum to an acetabular rim, the holes are positioned underneath the torn labrum and they may be difficult to see or locate with arthroscopic instruments after the drill or hole punch is removed since the labrum will cover the hole and obscure its location. This makes it difficult to find and position the suture anchor into the hole during the surgical procedure. This problem may become even more acute after delivering a first anchor and attempting to deliver a second anchor into the same pre-drilled hole. With the labrum captured by the suture extending between the two anchors, it becomes more difficult to move the labrum out of the way in order to locate the target hole for the second anchor. FIG. 54 illustrates a method for locating a pre-drilled hole. A suture anchor delivery instrument 4504 may include an optical coupling 4502 so that an external light source (not shown) may be optically coupled to the suture anchor delivery instrument 4504. Thus, light will be delivered from a light source through a light pipe such as a fiber optic to the area adjacent the pre-drilled hole 4508. The light 4506 illuminates the area with enough intensity and with a suitable wavelength so that the light is transmitted through the labrum L to illuminate the underlying bone and hole 4508. The light may be from an LED, laser or other suitable source. The light pipe may comprise one or more optical fibers or other suitable light transmission means and may be disposed in a lumen in the delivery instrument or in a separate member which is positioned alongside the delivery instrument or coupled to its exterior. With the location of the pre-drilled hole visible, the surgeon may deliver the suture anchor into the hole using the delivery instrument.

Figure 19:
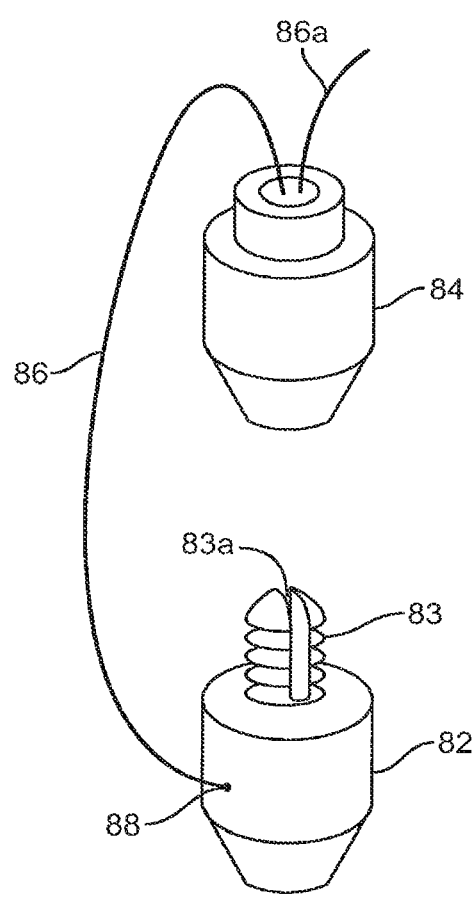
FIGS. 19-20 illustrate exemplary embodiments of suture anchor coupling mechanisms.
Figure 55:
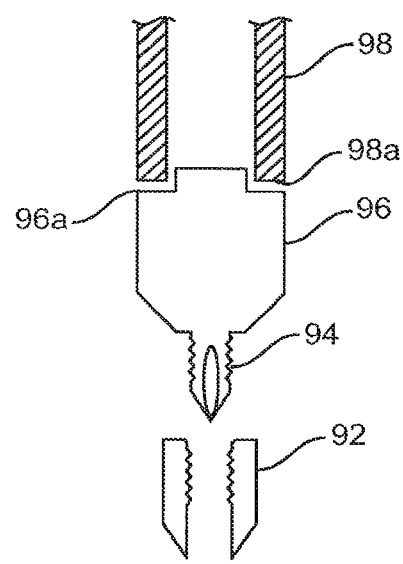
FIG. 55 illustrates a suture anchor delivery instrument.

FIG. 55 illustrates a variation of the embodiment in FIG. 19. In this exemplary embodiment, two anchors 92, 96 are placed end-to-end into engagement with one another. This variation is similar to that of FIG. 19, with the major difference being that the coupling element 94 is fixed to the top or proximal-most anchor 96 instead of on the bottom or distal-most anchor 92. The coupling element 94 may take any of forms previously described with respect to coupling element 83 in FIG. 19. Additionally, in this embodiment, a pusher tube 98 may be used to help drive anchor 96 into the bone or to help drive the two anchors into engagement with one another. A distal end 98a of the pusher tube 98 may be placed against a shoulder 96a of the upper anchor 96 and used to press the two anchors together. Alternatively, the proximal end of the pusher tube 98 may also be impacted with a hammer or similar object to help drive the two anchors into the bone and into engagement with one another. It will be understood that the distal and proximal anchors 92, 94 will be coupled to a length of suture and will include a knotless cinching mechanism in one or both anchors as described elsewhere herein.

Figure 56A:
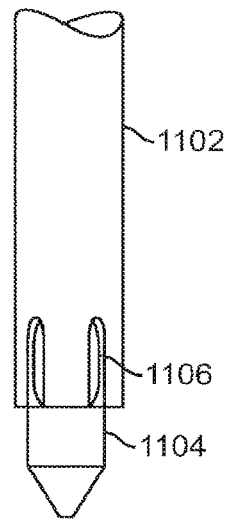
FIGS. 56A-56B illustrate an exemplary delivery instrument.
Figure 56B:
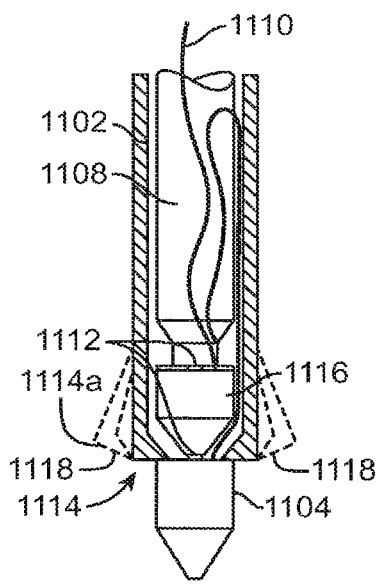

FIGS. 56A-56B illustrate an exemplary embodiment of a delivery instrument for deploying suture anchors in an end-to-end configuration. FIG. 56B is a cross-section of FIG. 56A and highlights the internal components of the delivery instrument. An outer shaft 1102 carries both anchors 1104, 1116 and a suture 1110 is coupled to each anchor. A plurality of slots 1106 near the distal end of the outer shaft 1102 form several deflectable arms 1114. Deflectable arms have inwardly extending fingers 1118 at their distal end which engage the proximal end of the distal anchor 1104. Pusher rod 1108 is slidably disposed in outer shaft 1102 and is engaged with the proximal end of suture anchor 1116. The distal end of anchor 1116 is also engaged with the proximal end of anchor 1104. Coupling mechanisms 1112 such as snap fits, threaded rods, or other joining mechanisms are used to join the two anchors 1104, 1116 together as described above. In use, pusher rod 1108 is slidably advanced within outer shaft 1102 so that the first anchor 1104 is exposed from the distal end of outer shaft 1102. As the pusher rod advances the first anchor 1104 distally, the arms 1114 deflect radially outward until the anchor 1104 is exposed distally thereof. The arms 1114 return to their radially inward position and thus the fingers 1118 at the distal end of the arms 1114a can then be used to push the first anchor into the bone or the pre-drilled hole in the bone. Shaft 1102 and pusher rod 1108 are then retracted along with proximal-most anchor 1116 to decouple it from the distal-most anchor 1104. Once the first anchor is in place, the instrument is manipulated so as to capture the target tissue with the suture 1110. Pusher rod 1108 is then advanced within shaft 1102 to push proximal-most anchor 1116 beyond fingers 1118 on deflectable arms 1114. The deflectable arms flare outwardly as the second anchor is advanced past the arms, and then the arms return to their unbiased position where they can be used to push the second anchor into the bone or the hole and also into engagement with the first anchor 1104. Once the two anchors have been coupled together (e.g. by threading them together or snap fitting or press fitting them together), the pusher rod 1108 may be released from the second anchor 1116 by unthreading, unsnapping or otherwise uncoupling the coupling mechanism 1112 between the two components.

Figure 57:
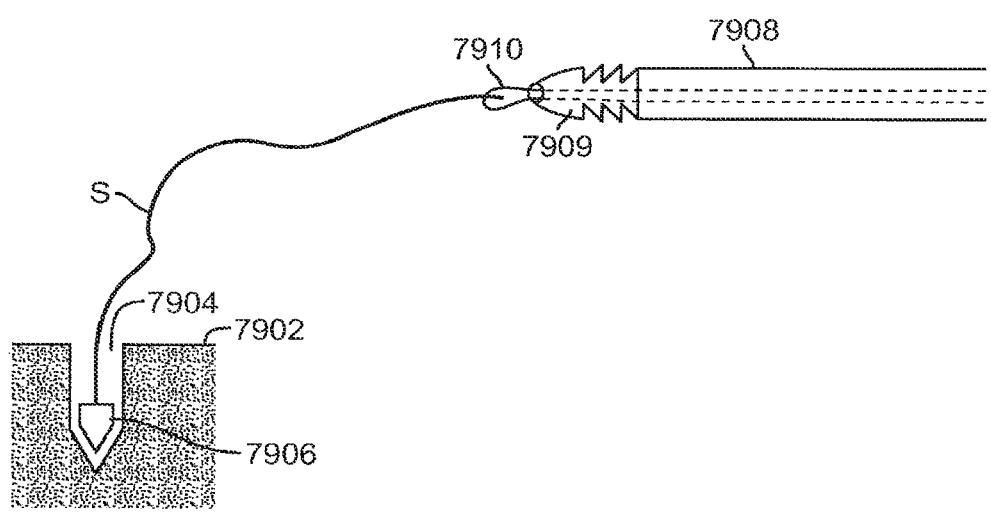
FIG. 57 illustrates an exemplary delivery instrument.

FIG. 57 illustrates another method of locating a suture anchor hole without requiring that a drill guide is kept in place. Once a hole 7904 has been pre-drilled into the bone 7902 a first anchor 7906 to which a guide filament S of wire, suture or other flexible material is coupled may be positioned into the hole 7904. Guide filament S may be used to help direct a delivery instrument 7908 carrying a second anchor 7909 through the tissue and blood, back to the hole 7904. Guide filament S may pass slidably through a loop, lasso 7910 or other coupling mechanism on the second anchor 7909 or delivery instrument 7908 over which it can be advanced back to the hole 7904. In this manner, the delivery instrument 7908 may be advanced along the guide filament S easily back to the hole 7904 to deliver additional suture, suture anchors or other materials required for the surgical repair. First anchor 7906 need not have the level of retention force that is required for the second anchor which is to be used in the surgical repair itself, needing only to hold the guide filament S while it is tensioned sufficiently to guide instruments back to hole 7904. First anchor 7906 may thus be a self expanding resilient wire coil or ball of randomly bent wire, a self-expanding stent-like structure, or a more rigid frictionally-retained structure adapted to be pressed or pounded into hole 7904. Alternatively, first anchor 7906 may have scales, barbs, wings or similar expanding structures on its outer surface to retain it within the hole. Any of the embodiments of the anchors disclosed elsewhere herein may also be used.

Figure 58A:
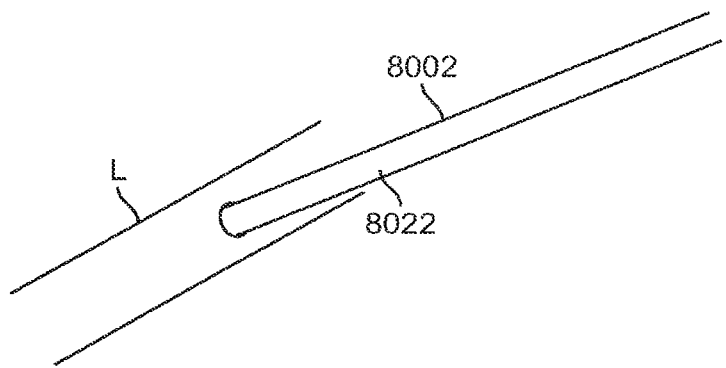
FIGS. 58A-58H illustrate an exemplary method of suture anchor delivery.
Figure 58B:
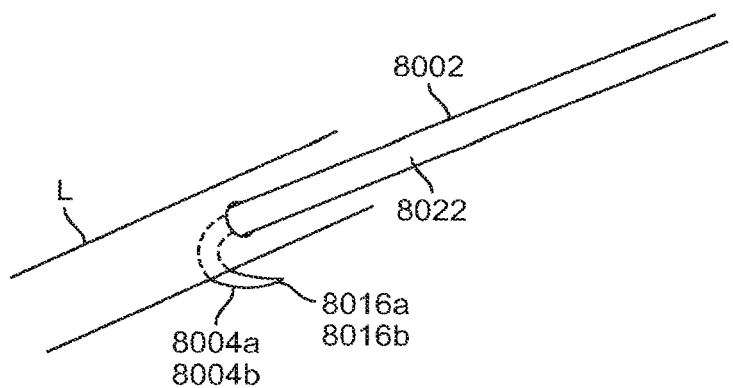
Figure 58C:
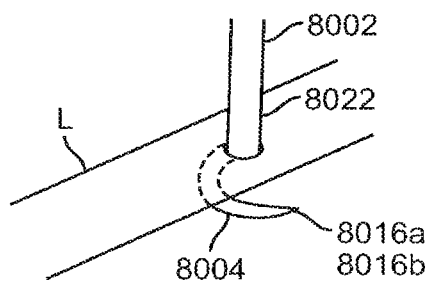
Figure 58D:
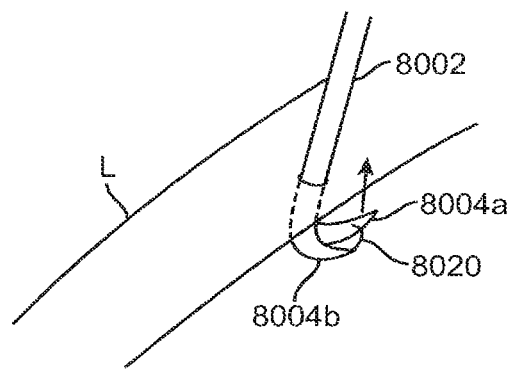
Figure 58E:
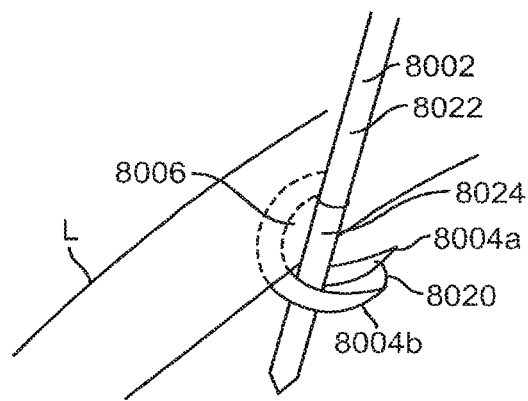
Figure 58F:
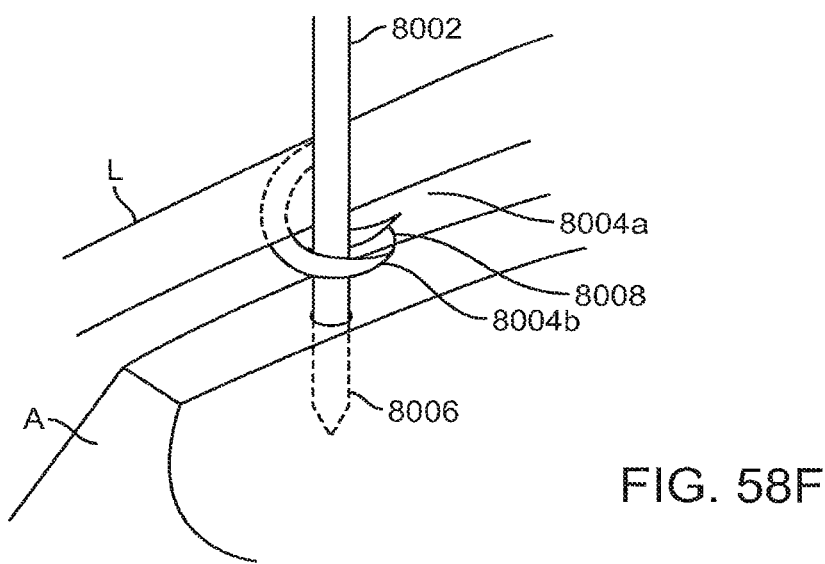
Figure 58G:
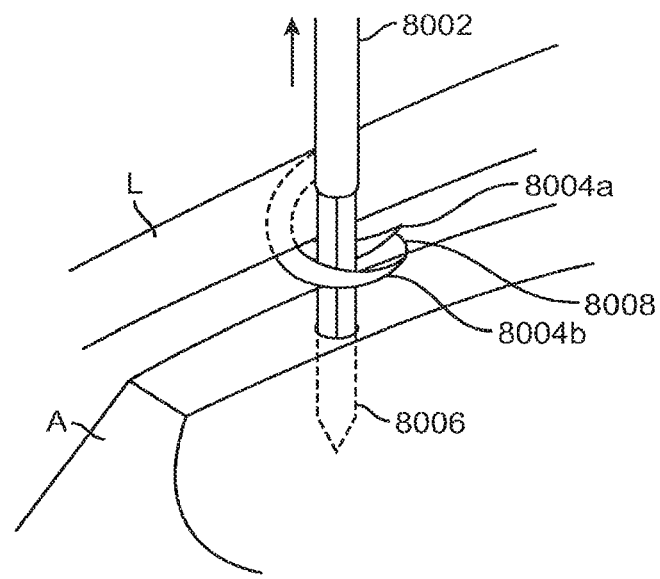
Figure 58H:
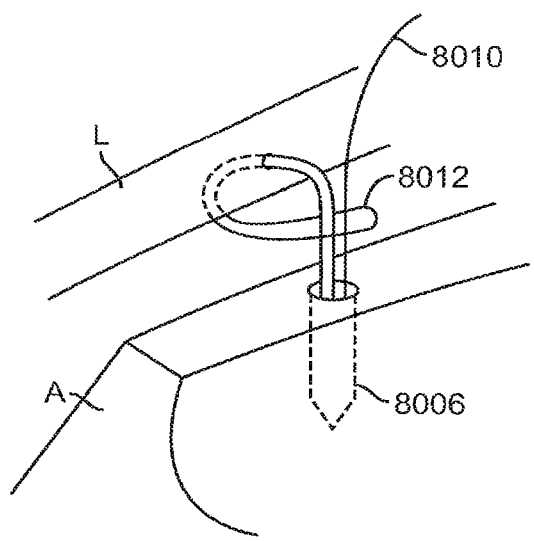

FIGS. 58A-58H illustrate another exemplary method of re-attaching damaged tissue to a substrate tissue such as bone using a single anchor with a closed loop. A suture passer and anchor delivery instrument 8402 carries an anchor 8406 (best seen in FIG. 58E), a suture S and a pair of curved grasping jaws 8404a, 8404b within the outer shaft 8422. The distal tips 8416a, 8416b of jaws 8404a, 8404b are sharpened so as to penetrate tissue. Jaws 8404a, 8404b have a discontinuous eyelet, hook, or other means (not shown) near their distal tips to releasably hold a loop of suture S between them and are rotatable about the longitudinal axis of the instrument 8402 so that the distal tips 8416a, 816b of the jaws are movable from a closed position adjacent to one another to an open position in which they are spaced apart with the suture extending between them. The instrument 8402 is advanced adjacent the damaged tissue, here a torn labrum L as seen in FIG. 58A. The grasping jaws 8404a, 8404b are then deployed from the instrument 8402 and passed through the torn labrum L in FIG. 58B in the closed position. A suture loop (not visible in the figure) is carried by the jaws and is thus passed through the labrum therewith. The instrument 8402 is then positioned so that it is substantially perpendicular to the torn tissue or in any other desired orientation, as illustrated in FIG. 58C. In FIG. 58D, the grasping jaws 8404a, 8404b are then opened after passing through the labrum so that a portion of the suture S passes between both jaws, thus opening loop 8420 in the suture. The anchor 8406 is the deployed from the instrument 8402 in FIG. 58E such that the anchor passes between the jaws 8404a, 8404b and through the loop 8420. An inner shaft 8424 carrying anchor 8406 is advanced from the outer shaft 8422 of the instrument 8402, to drive the anchor directly into the bone or into a pre-drilled hole as seen in FIG. 58F. Once the anchor 8406 is positioned in the acetabulum, inner shaft 8424 is decoupled from the anchor 8406 and the instrument 8402 may be retracted away from the bone, exposing the three segments of suture S extending from anchor 8406, as seen in FIG. 58G. The jaws are then decoupled from the suture loop and refracted back through the labrum and the instrument 8402 is removed, as illustrated in FIG. 58H. The free end 8410 of the suture S may then be pulled in order to adjust length or tension of the suture and secure the labrum with the acetabulum. The anchor may have any of the cinching mechanisms described above.

Figure 59A:
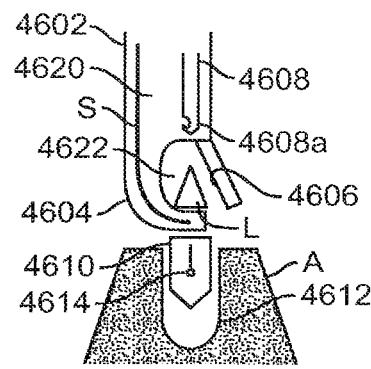
FIGS. 59A-59D illustrate an exemplary method of suture anchor delivery.

FIGS. 59A-59D illustrate an alternative embodiment of a suture anchor delivery instrument and method of use. A hole 4612 is pre-drilled in the acetabulum A as seen in FIG. 59A.

Figure 59B:
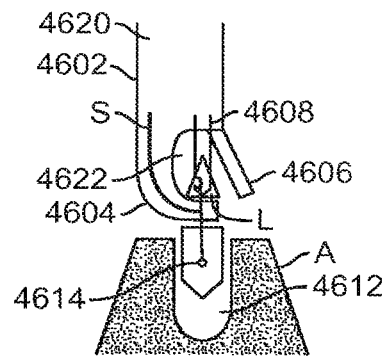
Figure 59C:
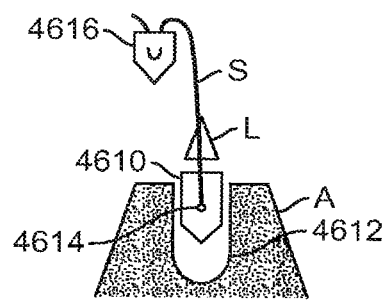
Figure 59D:
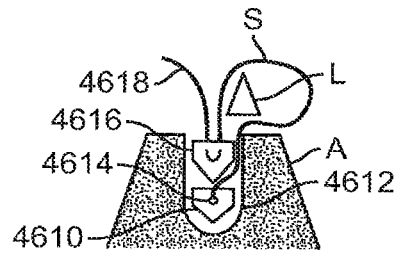

A suture anchor delivery instrument 4602 includes a tubular shaft 4620 and a grasping mechanism having a pair of opposable jaws 4604, 4606 and a penetrating needle 4608 slidably mounted within the tubular shaft 4620. The penetrating needle has a hook 4608a formed near its distal end which is adapted to grasp a suture held by fixed jaw 4604 as described below. A C-shaped fixed jaw 4604 extends from the distal end of tubular shaft 4620 and forms a channel 4622 configured to receive the target tissue to be repaired. A movable jaw 4606 is pivotably mounted to tubular shaft 4620 and is movable so as to extend across the open side of channel 4622. A suture S is coupled with a knot 4616 or by other means to a first anchor 4610 and extends through fixed jaw 4604 into tubular shaft 4620. The first anchor 4610 is releasably held at the distal end of fixed jaw 4604 to extend distally therefrom. In use, first anchor 4610 is deployed from the fixed jaw 4604 into the hole 4612 and then the torn labrum L is positioned in channel 4622 and retained therein by closing movable jaw 4606. The piercing needle 4608 is then advanced across channel 4622 and through the torn labrum L until it engages and captures the suture S held by fixed jaw 4604, as seen in FIG. 59B. The needle is retracted, pulling the suture S through the labrum. The instrument is then removed, with the suture S being slidably advanced from the tubular shaft 4620. A second anchor 4616, preferably having one of the cinching mechanisms described herein, is then coupled to the suture as illustrated in FIG. 59C. The second anchor 4616 is then positioned end-to-end or concentrically with the first anchor 4610 in hole 4612 as described elsewhere herein. Alternatively second anchor 4616 may be placed in a separate hole in the acetabulum A. The free end 4618 of the suture S may then be pulled in order to adjust length and tension in the suture as desired and to secure the torn labrum L securely to the acetabular rim substrate.

Figure 60A:
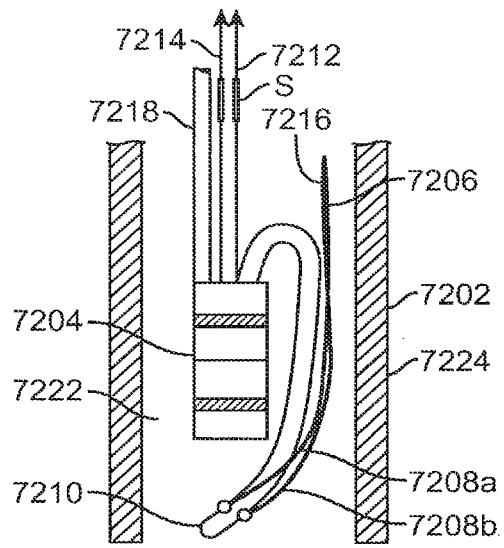
FIGS. 60A-60B illustrate an exemplary delivery instrument.
Figure 60B:
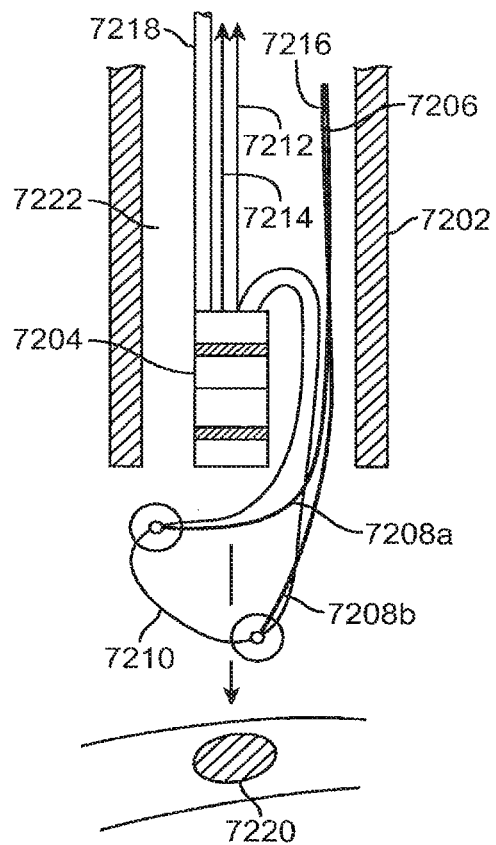

An exemplary instrument for delivering a suture anchor is schematically illustrated in 30 FIGS. 60A-60B. The delivery instrument 7202 includes an elongate outer shaft 7224 having a central channel 7222 in which the suture anchor 7204 and suture S are disposed. Suture anchor 7204 may taken the form of any suture anchor disclosed herein. An optional pusher tube 7218 is also disposed in channel 7222 along with a suture spreader 7206 having a pair of spreadable arms 7208a, 7208b coupled to an elongate shaft 7216. The free ends 7212, 7214 of the suture S extending away from the suture anchor 7204 may extend through the central channel 7222 toward a proximal end of the delivery instrument 7202 so that the ends may be manipulated by a physician outside of the patient's body, or the suture ends may only advance a short distance in the central channel 7222. In operation, the delivery instrument 7202 is advanced toward a treatment site and the suture spreader 7206 is advanced from the central channel 7222 so that the arms 7208a, 7208b are unconstrained and expand outward. The suture S is coupled to both arms 7208a, 7208b such that when the arms expand outwardly, the suture S forms a loop 7210 as seen in FIG. 60B. The suture spreader 7206 may be a superelastic or shape memory material such as Nitinol that is pre-shaped to spread to a desired configuration. The suture S may be looped around the tissue to be repaired (e.g. torn labrum, not illustrated) and then anchor 7204 is then advanced distally out of the central channel 7222 and passes through the suture loop 7210 into a hole 7220 pre-drilled in bone. The suture anchor 7204 may be advanced out of the central channel 7222 by actuating the pusher tube 7218 or other mechanisms may be employed. The free ends 7212, 7214 of the suture S can then be pulled in order to adjust length or tension in the suture S and the excess suture may be severed. In this embodiment, the suture anchor 7202 is advanced independently from the suture spreader 7206, however in alternative embodiments the two may be operatively coupled together so that they are both advanced from the delivery instrument together.

Figure 61A:
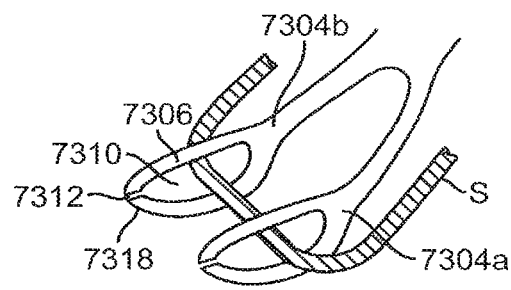
FIG. 61A-61C illustrate an exemplary delivery instrument.
Figure 61B:
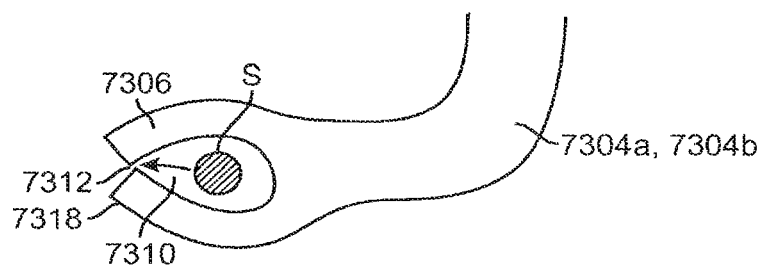
Figure 61C:
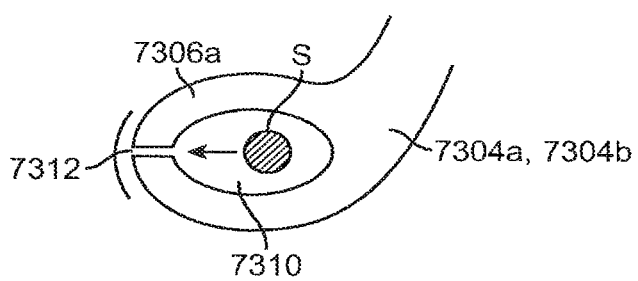

The suture spreader 7206 in FIGS. 60A-60B is formed from a wire-like material and the suture is coupled to arms 7208a, 7208b preferably by passing the suture S through eyelets (not illustrated) at the ends. This configuration is advantageous because it presents a low profile that may be easily be contained in shaft 7224. FIG. 61A illustrates the suture spreader arms 7304a, 7304b in greater detail. Each arm includes an upper finger 7306 and a lower finger 7318 that are biased to form an eyelet loop 7310 and so that the tips of the fingers close against one another forming a slit 7312. The suture S may be passed through the eyelet loop 7310 on each suture spreader arm 7304a, 7304b. The eyelet loop 7310 may be sized so that the suture S is loosely held by the fingers 7306, 7318 and thus when the spreader arms 7304a, 7304b expand outward, arms will open up forming suture loop 7305 without binding. Moreover, the slit 7312 in each spreader arm 7304a, 7304b allows the suture S to be disengaged from the spreader by pulling the suture therepast which spreads the fingers 7306, 7318 apart, opening the slit enough to release the suture S. FIG. 61B illustrates a side view of the suture spreader arm 7304a, 7304b. In an alternative embodiment shown in FIG. 61C, the fingers 7306a, 7306b are shaped to form a smooth arcuate tip 7314 that will not cause trauma to adjacent tissue as it is advanced and manipulated.

Figure 62A:
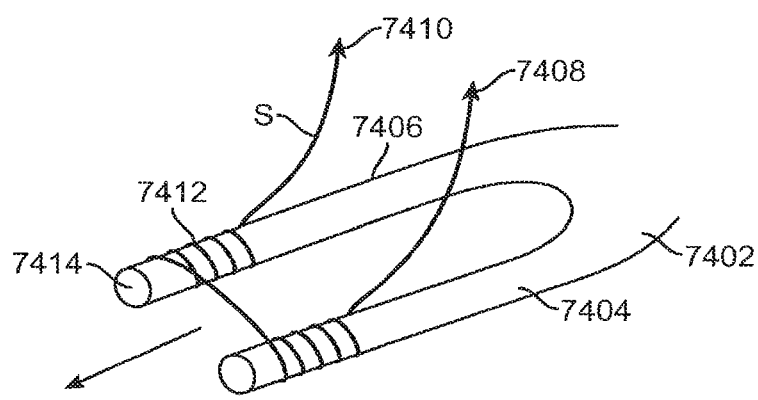
FIGS. 62A-62B illustrate an exemplary delivery instrument.
Figure 62B:
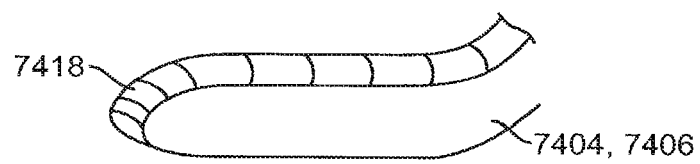

An alternative embodiment of a suture spreader is illustrated in FIGS. 62A-62B. The suture spreader 7402 includes a pair of substantially cylindrical arms 7404, 7406 that extend substantially parallel to one another. The suture S may be wrapped 7412 around each arm during deployment but may be easily slid off from each arm 7404, 7406 when the suture spreader 7402 is detached from the suture S. The arms 7404, 7406 may be fabricated from a metallic or polymer wire or pins, or they may be machined from a single integral piece and may be superelastic, shape memory or spring temper to spring outwardly upon deployment from a delivery instrument. The embodiment in FIG. 62A may include arms 7404, 7406 having a straight section for wrapping the suture S therearound and a flat cylindrical end 7414, or a rounded distal tip 7418 as seen in FIG. 62B to minimize trauma to adjacent tissue during deployment as well as to facilitate insertion into the treatment area.

Figure 63:
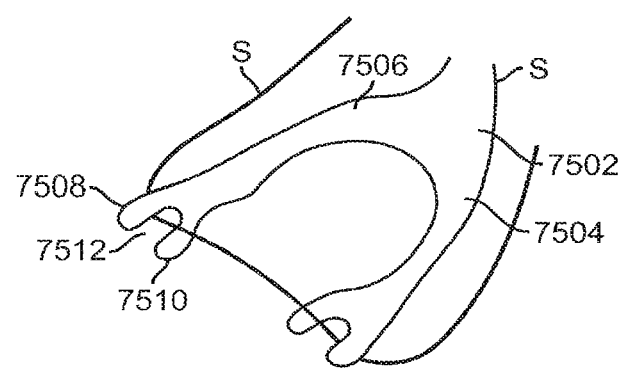
FIG. 63 illustrates an exemplary delivery instrument.

FIG. 63 illustrates another alternative embodiment of a suture spreader. The suture spreader 7502 includes a pair of substantially parallel arms 7504, 7506. Each arm includes a pair of fingers 7508, 7510 that form a receiving slot 7512 for receiving the suture S. The receiving slot 7512 may be sized to accommodate a number of different suture sizes and geometries. Similar to other suture spreaders described above, the arms 7504, 7506 will expand outwardly upon release from the delivery instrument, thereby forming a large suture loop 7305 (FIG. 61A) through which the suture anchor may pass. The arms may be fabricated from similar materials as discussed above with reference to FIGS. 61A-61C and FIGS. 62A-62B.

FIGS. 64A-64H illustrate an exemplary method of using a suture anchoring system having an anchor and a needle to reattach a torn labrum to the acetabular rim A. FIG. 64A shows the labrum L torn from the acetabular rim A. In FIG. 64B, the torn labrum L is moved to one side and a delivery instrument 6702 is used to position a suture anchor 6704 into the acetabular rim. The anchor may be driven through the cartilage into the bone of the acetabulum or the anchor may be positioned in a pre-drilled hole. The delivery instrument 6702 is then retracted away from the anchor such that suture S is metered out and partially encircles the torn labrum L, as shown in FIG. 64C. One end of the suture is attached to the anchor 6704 and the other end of the suture S is attached to a tissue piercing needle 6706 carried by the delivery instrument 6702. After partially encircling the torn labrum with the suture S, the needle 6706 is advanced from the delivery instrument so that it pierces the torn labrum L as illustrated in FIG. 64D. FIG. 64E shows a pusher rod 6708 advanced from the delivery instrument 6702 so as to push the needle 6706 through the labrum L and into a central channel of the anchor 6704. A locking mechanism (not illustrated) couples the needle and the anchor together and the delivery instrument is then retracted away from the torn labrum L, metering out additional suture, creating a free end 6710 as seen in FIG. 64F. The delivery instrument is then removed from the surgical field as shown in FIG. 64G and then the surgeon can adjust tension in the suture by pulling the free end 6710 of the suture and cutting away and excess suture. The labrum L is now re-attached to the acetabular rim A where it will heal. This process may be repeated as many times as required along the length of the torn labrum.

FIGS. 65A-65H illustrate another exemplary method of re-attaching tissue. In FIG. 65A a torn labrum L is shown separated from the acetabular rim A. A delivery instrument 6802 is used to push the labrum L aside and insert an anchor 6804 into the acetabulum A, as shown in FIG. 65B. The anchor 6804 may be inserted directly into the acetabular rim A or in a hole pre-drilled in the acetabulum A. In FIG. 65C the delivery instrument 6802 is retracted away from the labrum L and a tissue piercing needle 6806 is then deployed from the delivery instrument 6802. The delivery instrument 6802 is advanced distally so that needle 6806 pierces and passes through the labrum, pulling a portion of the suture with it as seen in FIG. 65D. A pusher rod 6808 is then advanced distally from the delivery instrument 6802 so as to push the needle 6806 into a central channel of the anchor 6804 where the two lock together, as shown in FIG. 65E. The delivery instrument 6802 is then retraced away from the labrum L. A free end 6810 of the suture S is also pulled away from the labrum L, as illustrated in FIG. 65F. In FIG. 65G, the delivery instrument 6802 is removed from the surgical field and in FIG. 65H, the free end 6810 is pulled by the surgeon in order to adjust length and tension in the suture which captures the labrum L. The excess suture is then severed and removed. This process may be repeated along the length of the torn labrum.

Figure 66:
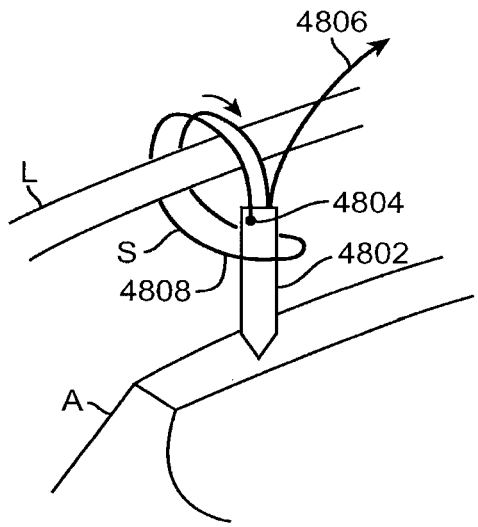
FIGS. 66-69 illustrate exemplary embodiments of suture anchor delivery.

A number of the suture anchor systems described above use two anchors placed end-to-end in the bone. In some cases it may be preferable to place only a single anchor into the bone. The exemplary embodiment of FIG. 66 illustrates a single anchor embodiment. Suture S is pre-threaded in an anchor 4802 which may include a cinching mechanism 4804, such as any of those disclosed herein. Suture S forms a loop 4808 which is first passed around the labrum L or through a penetration therein so that the end of the loop is exposed on the opposite side of the labrum. Suture anchor 4802 is then passed through the interior of the exposed end of the loop thereby completely capturing the labrum. Anchor 4802 is then inserted directly into the acetabulum A or into a hole pre-drilled into the bone. The free end 4806 of the suture exits the anchor 4802 and may be pulled to adjust the length or tension in the suture.

Figure 67:
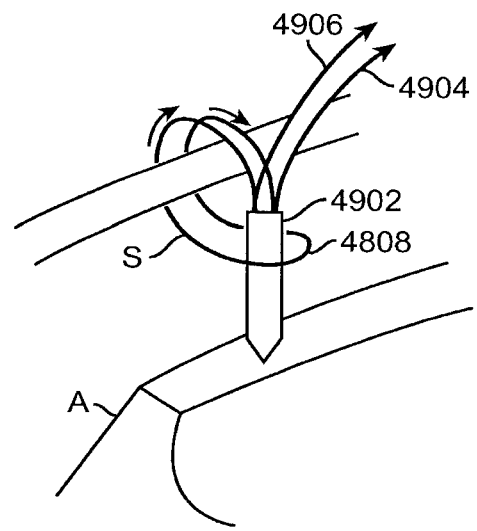

Another exemplary embodiment of a suture anchor system using only a single anchor is illustrated in FIG. 67. This embodiment is similar to that of FIG. 66 except that anchor 4902 has two one-way cinching mechanisms to allow either end 4904 or end 4906 of suture S to be adjustably tensioned. The labral tissue is captured and the anchor placed in the manner described above in connection with FIG. 66.

Figure 68:
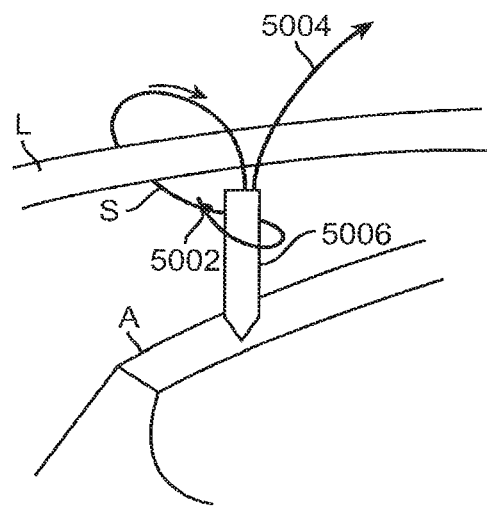

FIG. 68 shows another exemplary embodiment of a suture anchor system requiring only a single anchor. In this embodiment, one end of a suture S has a pre-formed loop 5002 that is first inserted through or passed around the labrum L. Anchor 5006 is then passed through the loop 5002 and inserted into the acetabulum by driving it into the bone or placing it in a pre-drilled hole. The suture passes through a one-way cinching mechanism (not shown) in anchor 5006 and a free end 5004 exits the anchor. The cinching mechanism may be any of those described in this specification. The free end 5004 may be pulled in order to adjust length or tension in the suture.

Figure 69:
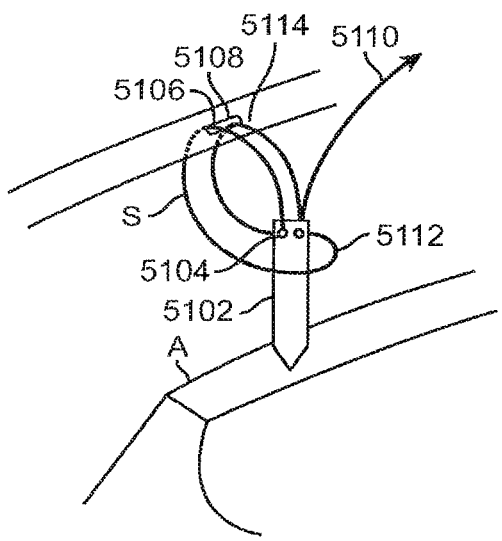
Figure 70A:
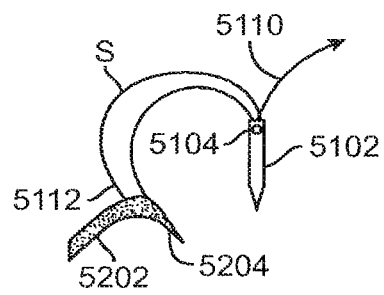
FIGS. 70A-70B illustrate exemplary embodiments of suture anchor delivery.
Figure 70B:
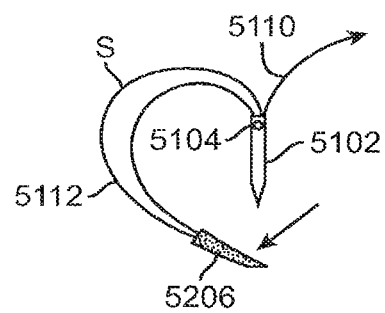

FIG. 69 illustrates still another exemplary embodiment of a suture anchor system with a single anchor. One end of a suture S is attached to the anchor 5102 with a knot 5104 or other coupling mechanism. The other end 5110 passes through a cinching mechanism in the anchor, which may be any of those disclosed herein, forming a closed loop 5112. In this embodiment, the loop 5112 may be passed through the labrum using a specialized loop passing tool, shown in FIGS. 70A-70B. In FIG. 70A, loop 5112 of the suture S may be coupled to a passing tool 5202 having a pointed tip 5204. The tool may be used to pierce the labrum with a single, or two holes 5106, 5108, and pass the loop 5112 therethrough. Loop 5112 is then released from passing tool 5202. FIG. 70B illustrates a needle 5206 coupled to loop 5112 of the suture S. The needle may be passed through the labrum along with the suture. Needle 5206 may then be removed from loop 5112. Once loop 5112 is passed through labrum L, the anchor is passed through the loop and driven into the bone or inserted in a predrilled hole in the bone. The free end 5110 may then be pulled in order to adjust suture length or tension. FIG. 69 further illustrates an alternative approach for capturing the labrum in which the suture is passed through the exposed edge 5114 of the labrum L which has been torn or cut from the acetabulum, rather than through the anterior face of the labrum. With this positioning of the suture, the labrum may be drawn directly into engagement with the acetabular rim with improved circumferential alignment between the labrum and acetabulum. Further, the sutures are exposed only on the outer side of the labrum so that there is no risk of engagement between the sutures and the femoral head as it moves.

Figure 71:
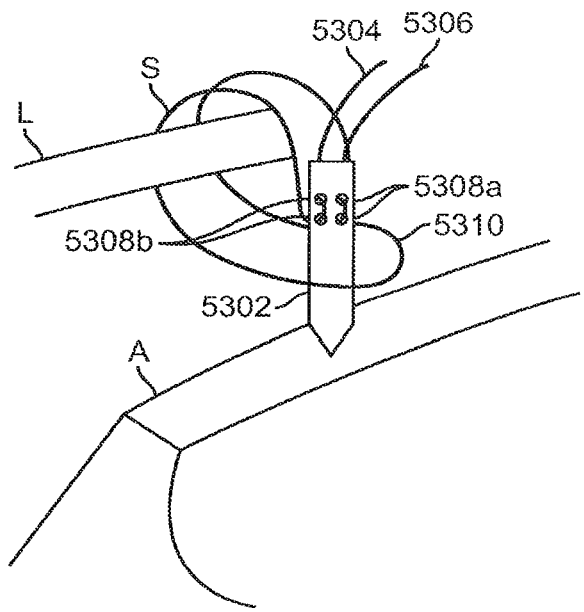
FIG. 71 illustrates an exemplary embodiment of suture anchor delivery.

FIG. 71 illustrates another exemplary embodiment of a suture anchor system utilizing only a single anchor. This embodiment is substantially similar to the embodiment illustrated in FIG. 67 above with each end 5304, 5306 of suture S in its own cinching mechanism in anchor 5302. However, in this embodiment, each cinching mechanism comprises a pair of apertures 5308a, 5308b in the outer wall of the anchor through which the suture is threaded, like that illustrated in FIG. 46. After passing the loop 5310 through the labrum L, passing the anchor through the loop, and deploying the anchor in the acetabulum, each of the free ends 5304, 5306 may be pulled in order to adjust suture length or tension.

Several exemplary methods of deploying suture anchors into tissue have been described above. However, this is not meant to be limiting. Other methods of deploying the anchor and re-attaching the damaged tissue to the substrate tissue may be used, such as those disclosed in U.S. Provisional patent applications and U.S. patent applications previously incorporated herein by references. Moreover, various other features such as anchor tip configurations, anchor coupling mechanisms, tissue capturing methods and suture cinching mechanisms have also been disclosed above and in references incorporated herein. One of skill in the art will appreciate that these features may be combined with one another or substituted for another and thus any number of combinations may be used.

While the above detailed description and figures are a complete description of the preferred embodiments of the invention, various alternatives, modifications, and equivalents may be used. The various features of the embodiments disclosed herein may be combined or substituted with one another. Therefore, the above description should not be taken as limiting in scope of the invention which is defined by the appended claims.

What is claimed is:

1. A knotless suture anchoring system, said system comprising:
    a first anchor positionable in tissue and having a longitudinal axis;
    a cinching mechanism coupled to the first anchor, the cinching mechanism comprising a body having first and second transverse apertures spaced apart along the longitudinal axis and separated by a bar; and
    a length of suture threaded through the first and second apertures so as to form a loop around the bar, the suture having first and second extremities extending respectively from the first and second apertures on the same side of the body, the first and second extremities being generally parallel to and overlying one another such that the second extremity is sandwiched between the first extremity and the body, wherein exerting tension on the first extremity compresses the second extremity against the body to prevent movement of the suture relative to the body, and wherein exerting tension on the second extremity allows the suture to move longitudinally relative to the body.

2. The system of claim 1, wherein the suture comprises a flat cross-sectional profile.

3. The system of claim 2, wherein the anchor has a proximal end, a distal end, and the longitudinal axis extends therebetween, the first and second apertures extending through the body in a direction transverse to the longitudinal axis.

4. The system of claim 1, wherein the suture comprises a round cross-sectional profile.

5. The system of claim 1, wherein the cinching mechanism is positioned in a central channel of the anchor.

6. The system of claim 5, wherein the anchor has a proximal end, a distal end, and the longitudinal axis extends therebetween, the central channel being aligned with the longitudinal axis, the channel having an opening at the proximal end, and wherein at least one of the first and second extremities extend through the opening.

7. The system of claim 1, wherein the apertures are disposed along the body in a single line substantially parallel with the longitudinal axis.

8. The system of claim 1, wherein the body comprises a plate and the first and second apertures comprise slots extending through the plate.

9. The system of claim 8, wherein the anchor has a proximal end, a distal end, and the longitudinal axis extends therebetween, the plate being oriented generally parallel to the longitudinal axis.

10. The system of claim 8, wherein the plate is disposed in a central channel of the anchor.

11. The system of claim 1, wherein the body has a face against which the second extremity is compressed, the bar being laterally offset from the face.

12. The system of claim 1, wherein the body has a face against which the second extremity is compressed, the first aperture intersecting the face so as to define a corner which engages the second extremity.

13. The system of claim 12, wherein the corner has an edge which locks the second extremity when the first extremity is tensioned.

14. The system of claim 12, wherein the corner defines an angle of no more than about 90 degrees.

15. The system of claim 12, wherein the face comprises one or more features to induce friction with the second extremity when the first extremity is tensioned.

16. The system of claim 1, wherein the body comprises a barrel disposed in an aperture in a sidewall of the anchor transverse to the longitudinal axis of the anchor.

17. The system of 16, wherein the barrel is rotatably disposed in the sidewall aperture, the rotatable barrel having a locked position and an unlocked position, the unlocked position allowing the suture to move, the locked position constraining movement of the suture.

18. The system of claim 17, wherein the apertures extend through the barrel parallel to a first axis, and in the unlocked position, the first and second extremities extend from the apertures substantially parallel to the first axis.

19. The system of claim 17, wherein the apertures extend through the barrel parallel to a first axis, and in the locked position, the first and second extremities extend from the apertures in a direction transverse to the first axis.

20. The system of claim 1, wherein the cinching mechanism is integral with the first anchor.

21. The system of claim 20, wherein the cinching mechanism and the first anchor are a single molded part.

22. The system of claim 1, wherein the cinching mechanism is on a separate member configured to be attached to the first anchor at a surgical site.

23. The system of claim 1, wherein the cinching mechanism is coupled to a second anchor adapted for being positioned in tissue and which may be coupled to the first anchor.

24. The system of claim 1, wherein the cinching mechanism requires no movement of parts relative to the first anchor to prevent the suture from moving when the first extremity is tensioned.

25. The system of claim 1, wherein the cinching mechanism is a single molded part.

26. The system of claim 1, wherein the first anchor has an outer diameter which is no more than about 3.5 mm along its entire length.

27. The system of claim 1, further comprising a second anchor positionable in the tissue.

28. The system of claim 27, wherein one of the two anchors is positioned concentrically in the other of the two anchors.

29. The system of claim 27, wherein one of the two anchors is positioned end to end with the other of the two anchors.

30. The system of claim 29, wherein the first anchor comprises a distal end and a proximal end and the second anchor comprises a distal end and a proximal end, and wherein one of the two anchors is positioned end to end with the other of the two anchors such that the proximal end of one of the two anchors is coupled to the distal end of the other of the two anchors.

31. The system of claim 27, wherein the loop is configured to be fully recessed inside a hole in bone or other tissue when the first anchor and second anchor are positioned in the hole.

32. A knotless suture anchoring system, said system comprising:
- a first anchor component having a longitudinal axis and a first cinching mechanism;
- a second anchor component initially detached from the first anchor component, at least one of the first and second anchor components being adapted for placement directly into bone or other tissue and comprising a retention feature on an exterior surface thereof for retaining the first or second anchor component in said bone or tissue;
- a coupling mechanism for coupling the second anchor component to the first anchor component; and
- a length of suture at least partially disposed in the first cinching mechanism, the suture having a first free end and a second free end, wherein the second free end is attached to the second anchor component, and wherein the first cinching mechanism allows the suture to pass through the first cinching mechanism in a first direction when the first free end is tensioned and constrains movement of the suture through the first cinching mechanism in a second direction opposite the first direction.

33. A knotless suture anchor system as in claim 32, wherein the second anchor component is received within a cavity in the first anchor component.

34. A knotless suture anchor system as in claim 32, wherein the first anchor component is received within a cavity in the second anchor component.

35. A knotless suture anchor system as in claim 32, wherein the first anchor component is coupled end-to-end with the second anchor component.

36. The system of claim 35, wherein the first anchor component comprises a distal end and a proximal end and the second anchor component comprises a distal end and a proximal end, and wherein one of the two anchor components is positioned end to end with the other of the two anchor components such that the proximal end of one of the two anchor components is coupled to the distal end of the other of the two anchor components.

37. A knotless suture anchor system as in claim 32, wherein the first cinching mechanism has no parts movable relative to the first anchor component.

38. A knotless suture anchor system as in claim 32, further comprising a second cinching mechanism coupled to the second anchor component, the suture having a second end coupled to the second cinching mechanism.

39. A knotless suture anchor system as in claim 32, wherein the second anchor component has a suture retention structure for retaining a second end of the suture therein.

40. A knotless suture anchor system as in claim 32, wherein the first anchor component and the first cinching mechanism are an integral molded construction.

41. A knotless suture anchoring system, said system comprising:
- a length of suture having a first free end and a second free end;
- a first anchor having a proximal end and a distal end, and being positionable in tissue;
- a second anchor having a proximal end and a distal end;
- a first cinching mechanism coupled to either the first anchor or the second anchor, wherein the first free end is at least partially disposed in the first cinching mechanism, and wherein the second free end is attached to the other of the first or the second anchor, and
- wherein the first cinching mechanism is adapted to allow the suture to be tensioned by pulling the first free end so that the suture passes through the first cinching mechanism in a first direction while movement of the suture through the first cinching mechanism in a second direction opposite the first direction is constrained; and
- a coupling element attached to one or both of the first and second anchors and adapted to couple the first and the second anchors together end-to-end.

42. The system of claim 41, wherein the coupling element comprises a threaded post, and wherein the first anchor is threadably engaged with the second anchor.

43. The system of claim 41, wherein the coupling element comprises a post having a plurality of barbs disposed thereon.

44. The system of claim 41, wherein the coupling element comprises a compression fitting.

45. The system of claim 41, wherein the suture is fixed to the first anchor and the cinching mechanism is on the second anchor.

46. The system of claim 45, wherein each of the first and second anchors is adapted to be placed in tissue separately from the other of the first and second anchors.

47. The system of claim 41, wherein the first and second anchor components are coupled together end-to-end such that the proximal end of first anchor is coupled to the distal end of the second anchor.

* * * * *